(12) United States Patent
Warner et al.

(10) Patent No.: US 7,169,970 B2
(45) Date of Patent: Jan. 30, 2007

(54) HERBICIDE RESISTANT PLANTS

(75) Inventors: Simon Anthony James Warner, Bracknell (GB); Timothy Robert Hawkes, Bracknell (GB); Christopher John Andrews, Bracknell (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 10/380,935

(22) PCT Filed: Sep. 14, 2001

(86) PCT No.: PCT/GB01/04131

§ 371 (c)(1),
(2), (4) Date: May 5, 2003

(87) PCT Pub. No.: WO02/26995

PCT Pub. Date: Apr. 4, 2002

(65) Prior Publication Data

US 2003/0200560 A1    Oct. 23, 2003

(30) Foreign Application Priority Data

Sep. 29, 2000 (GB) ................... 0023910.3
Sep. 29, 2000 (GB) ................... 0023911.1
Nov. 13, 2000 (GB) ................... 0027693.1

(51) Int. Cl.
*A01H 5/00* (2006.01)
*C12N 15/29* (2006.01)
*C12N 15/82* (2006.01)

(52) U.S. Cl. ............... 800/300; 435/320.1; 536/23.2; 536/23.6; 800/298

(58) Field of Classification Search ............. 800/300, 800/278, 288, 298; 536/23.2, 23.6; 435/320.1
See application file for complete search history.

(56) References Cited

U.S. PATENT DOCUMENTS 6,566,587 B1 * 5/2003 Lebrun et al. ............. 800/300

FOREIGN PATENT DOCUMENTS

FR   2736926    1/1997
WO   WO9704114  2/1997

OTHER PUBLICATIONS

Duggleby 1997, Gene vol. 190 pp. 245-249.*
1983 Genes, Benjamin Lewin editor, John Wiley & Sons, New York, ISBN 0-471-09316-5, pp. 191-192.*
Campbell et al 1990, Plant Physiology vol. 92, pp. 1-11.*
Gasser and Klee 1990, Nucleic Acids Research vol. 18, No. 9, p. 2821.*
Gasser and Klee, *Brassica napus 5-enolpyruvylshikimate-3-phosphate synthase gene* Accession No.: X51475, EMBL, Created Apr. 17, 1990.

* cited by examiner

*Primary Examiner*—David H Kruse
(74) *Attorney, Agent, or Firm*—Syngenta Limited

(57) ABSTRACT

Polynucleotide constructs encoding EPSPS enzymes are disclosed. The constructs have at least one transcriptional enhancer operably linked to a soybean or Brassica promoter and to a sequence respectively encoding the soybean or Brassica EPSPS chloroplast transit peptide and soybean or Brassica EPSPS enzyme. The EPSPS enzymes comprise a modified region that confers herbicide resistance.

29 Claims, 6 Drawing Sheets

HERBICIDE RESISTANT PLANTS

This application is a National Stage of International Application No. PCT/GB01/04131, filed Sep. 14, 2001, and published Apr. 4, 2002, as WO 02/26995, which claims the benefit of GB0023911.1, filed Sep. 29, 2000; and GB0023910.3, filed Sep. 29, 2000; and GB0027693.1, filed Nov. 13, 2000.

The present invention relates to recombinant DNA technology, and in particular to the production of transgenic plants which exhibit substantial resistance or substantial tolerance to herbicides when compared with non transgenic like plants. The invention also relates, inter alia, to the nucleotide sequences (and expression products thereof), which are used in the production of, or are produced by, the said transgenic plants.

Plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agricultural community to kill weeds in the field in which crops are to be grown for commercial purposes.

It is particularly preferred that the plants are substantially resistant or substantially tolerant to herbicides (hereinafter "glyphosate") which have 5-enol pyruvyl shikimate phosphate synthetase (hereinafter "EPSPS") as their site of action, of which N-phosphonomethylglycine (and its various salts) is the pre-eminent example.

The herbicide may be applied either pre- or post emergence in accordance with usual techniques for herbicide application to fields comprising crops which have been rendered resistant to the herbicide. The present invention provides, inter alia, nucleotide sequences useful in the production of such herbicide tolerant or resistant plants.

According to the present invention there is provided a glyphosate resistant EPSPS enzyme wherein in comparison with the wild type EPSPS the protein sequence is modified in that a first position is mutated so that the residue at this position is Ile rather than Thr and a second position is mutated so that the residue at this position is Ser rather than Pro, the mutations being introduced into EPSPS sequences which comprise the conserved region GNAGTAMRPL (SEQ ID NO: 66) in the wild type enzyme such that the modified sequence reads GNAGIAMRSL (SEQ ID NO: 67), wherein the enzyme does not comprise the sequence K(A/V)AKRAVVVGCGGKFPVE (SEQ ID NO: 68), characterised in that the enzyme is stable and possesses at least one of the following sequence motifs (i) to (viii) in which X is any amino acid and Z, $Z_1$ and $Z_2$ are any amino acid other than those specified:

(i) ALLMZAPLA, wherein Z is not S or T (SEQ ID NO: 51);
(ii) EIEIZDKL, wherein Z is not V (SEQ ID NO: 52);
(iii) FG(V/I)(K/S)ZEH, wherein Z is not V (SEQ ID NO: 53);
(iv) AL(K/R)ZLGL, wherein Z is not R (SEQ ID NO: 54);
(v) GLXVE$Z_1$DX$Z_2$XXXA(I/V)V, wherein $Z_1$ is not T and/or $Z_2$ is not E (SEQ ID NO: 55);
(vi) ITPP$Z_1$K(L/V)(K/N)$Z_2$, wherein $Z_1$ is not K and/or $Z_2$ is not T (SEQ ID NO: 56);
(vii) TIZ(D/N)PGCT, wherein Z is not N or L (SEQ ID NO: 57);
(viii) (D/N)YFXVLXZXX(K/R)H, wherein Z is not R (SEQ ID NO: 58).

A preferred embodiment of the enzyme comprises at least two of the motifs (i), (ii), (iii), (v) and (vi). In specific embodiments of the present inventive enzyme in motif (i) Z is A; in motif (ii) Z is I; in motif (iii) Z is A; in motif (iv) Z is K, T or A; in motif (v) $Z_1$ is R or A or less preferably D or E and $Z_2$ is preferably V or A or less preferably T; in sequence motif (vi) $Z_1$ is E or A and $Z_2$ is P, I or V; in motif (vii) Z is R or K; and in motif (viii) Z is T or S or less preferably Q. Particularly preferred embodiments of the said enzyme comprise one or more sequences selected from the group consiting of:

```
(i)    (IIV)VEGCGG(I/L/Q)FP(V/A/T)    (SEQ ID NO:59)
       (S/G)

(ii)   (I/V)VVGCGG(I/L/Q)FP(V/A/T)    (SEQ ID NO:60)
       E;

(iii)  (I/V)VVGCGG(I/L/Q)FP(V/A/T)    (SEQ ID NO:61)
       (S/G);

(iv)   (I/V)VVGCGGKFP(V/A/T)(S/G);    (SEQ ID NO:62)

(v)    (I/V)VEGCGGKFP(V/A/T)E;        (SEQ ID NO:63)

(vi)   (I/V)VEGCGG(I/L/Q)FP(V/A/T)    (SEQ ID NO:64)
       E;

(vii)  (I/V)VEGCGGKFP(V/A/T)(S/G).    (SEQ ID NO:65)
```

The present invention also comprises an isolated polynucleotide comprising a region which encodes the present inventive enzyme, particular such polynucleotides comprising, for example, a sequence depicted in SEQ ID Nos. 4 or 5, or a sequence obtained by hybridising an intron located in the SEQ ID 4 or 5 sequences with polynucleotides comprised in plant genomic libraries. The invention also includes an isolated polynucleotide comprising a region encoding a chloroplast transit peptide and a glyphosate resistant dicotyledenous 5-enolpyruvylshiikimate phosphate synthase (EPSPS) 3' of the peptide, the said region being under expression control of a plant operable promoter, with the provisos that the said promoter is not heterologous with respect to the said region, and the chloroplast transit peptide is not heterologous with respect to the said synthase.

By "heterologous" is meant from a different source, and correspondingly "non-heterologous" means derived from the same source—but at a gene rather than organism or tissue level. For example the CaMV35S promoter is clearly heterologous with respect to a petunia EPSPS coding sequence insofar as the promoter is derived from a virus and the sequence—the expression of which it controls—from a plant. The term "heterologous" according to the present invention has a still narrower meaning, however. For example "heterologous" as it relates to the present invention means that the petunia EPSPS coding sequence is "heterologous" with respect to, for example, a promoter also derived from petunia—other than that which controls expression of the EPSPS gene. In this sense the petunia promoter derived from the petunia EPSPS gene then used to control expression of an EPSPS coding sequence likewise-derived from petunia is "non-heterologous" with respect to the said coding sequence. "Non-heterologous" does not mean, however, that the promoter and coding sequence must necessarily have been obtained from one and the same (original or progenitor) polynucleotide. Likewise with respect to transit peptides. For example, a rubisco chloroplast transit peptide derived from sunflower is "heterologous" with respect to the coding sequence of an EPSPS gene likewise derived from sunflower (the same plant, tissue or cell). A rubisco transit peptide encoding sequence derived from sunflower is "non-heterologous" with respect to a rubisco enzyme encoding-sequence also derived from sunflower even if the origins of both sequences are different polynucleotides which may have been present in different cells, tissues or sunflower plants.

Most particularly preferred forms of the said polynucleotide include a construct which comprises the following components in the 5' to 3' direction of transcription: either (1):

(i) At least one transcriptional enhancer being that enhancing region which is upstream from the transcriptional start of the sequence from which the enhancer is obtained and which enhancer per se does not function as a promoter either in the sequence in which it is endogenously comprised or when present heterologously as part of a construct;

(ii) The promoter from the soybean EPSPS gene;

(iii) The soybean genomic sequence which encodes the soybean EPSPS chloroplast transit peptide;

(iv) The genomic sequence which encodes the soybean EPSPS;

(v) A transcriptional terminator;

wherein the soybean EPSPS coding sequence is modified in comparison with a wild type sequence in that a first position is mutated so that the residue at this position is Ile rather than Thr and a second position is mutated so that the residue at this position is Ser rather than Pro, the mutations being introduced into EPSPS sequences which comprise the conserved region GNAGTAMRPLTAAV (SEQ ID NO: 69)in the wild type enzyme such that modified sequence reads GNAGIAMRSLTAAV (SEQ ID NO: 70); or (2)

(i) At least one transcriptional enhancer being that enhancing region which is upstream from the transcriptional start of the sequence from which the enhancer is obtained and which enhancer per se does not function as a promoter either in the sequence in which it is endogenously comprised or when present heterologously as part of a construct;

(ii) The promoter from the *Brasicca napus* EPSPS gene;

(iii) The *Brasicca napus* genomic sequence which encodes the *Brasicca napus* EPSPS chloroplast transit peptide;

(iv) The genomic sequence which encodes the *Brasicca napus* EPSPS;

(v) A transcriptional terminator;

wherein the *Brasicca napus* EPSPS coding sequence is modified in comparison with a wild type sequence in that a first position is mutated so that the residue at this position is Ile rather than Thr and a second position is mutated so that the residue at this position is Ser rather than Pro, the mutations being introduced into EPSPS sequences which comprise the conserved region GNAGTAMRPLTAAV (SEQ ID NO: 69) in the wild type enzyme such that the modified sequence reads GNAGIAMRSLTAAV (SEQ ID NO: 70).

The present inventive polynucleotide, particularly the two disclosed in the immediately preceding paragraphs, may further comprise a sequence which encodes a chloroplast transit peptide/phosphoenolpyruvate synthase (CTP/PPS) or a chloroplast transit peptide/pyruvate orthophosphate dikinase (CTP/PPDK), which sequence is under expression control of a plant operable promoter. It is particularly preferred that the PPDK protein sequence is directed to the chloroplast in planta via its autologous transit peptide, and accordingly the polynucleotide of the immediately preceding sentence encodes such a non-heterologous combination. The PPDK encoding sequence can be derived from either a monocot or a dicot and the protein thus encoded is optionally not cold-labile. By "not cold labile" is meant that the enzyme retains at least 50% of its activity when incubated at 0 degrees Celsius for 5 minutes under experimental conditions similar to thosereferred to in Usami et al (1995) Plant Mol. Biol., 27, 969–980. Such a 'cold stable' enzyme is at least two-fold more stable than the like enzyme isolated from *F. bidentis*. The PPS or PPDK enzymes provide for elevated levels of PEP in the chloroplast which is the site of action of glyphosate and which contains the EPSPS enzyme.

The enhancing region of the polynucleotide preferably constitutes a sequence the 3' end of which is at least 40 nucleotides upstream of the closest transcriptional start of the sequence from which the enhancer is obtained. In a further embodiment of the polynucleotide, the enhancing region constitutes a region the 3' end of which is at least 60 nucleotides upstream of the said closest start, and in a still further embodiment of the polynucleotide the said enhancing region constitutes a sequence the 3' of which is at least 10 nucleotides upstream from the first nucleotide of the TATA consensus of the sequence from which the enhancer is obtained.

The polynucleotide according to the invention may comprise two or more transcriptional enhancers, which in a particular embodiment of the polynucleotide may be tandemly present.

In the present inventive polynucleotide the 3' end of the enhancer, or first enhancer if there is more than one present, may be between about 100 to about 1000 nucleotides upstream of the codon corresponding to the translational start of the EPSPS transit peptide or the first nucleotide of an intron or other untranslated leader sequence in the 5' untranslated region in the case that the said region contains an intron or other untranslated sequence. In a more preferred, embodiment of the polynucleotide, the 3' end of the enhancer, or first enhancer, is between about 150 to about 1000 nucleotides upstream of the codon corresponding to the translational start of the EPSPS transit peptide or the first nucleotide of in the 5' untranslated region, and in a still more preferred embodiment the 3' end of the enhancer, or first enhancer, may be between about 300 to about 950 nucleotides upstream of the codon corresponding to the translational start of the EPSPS transit peptide or the first nucleotide of an intron or other untranslated leader sequence in the 5' untranslated region. In a yet more preferred embodiment, the 3' end of the enhancer, or first enhancer, may be located between about 770 and about 790 nucleotides upstream of the codon corresponding to the translational start of the EPSPS transit peptide or the first nucleotide of an intron or other untranslated leader sequence in the 5' untranslated region.

In an alternative inventive polynucleotide, the 3' end of the enhancer, or first enhancer, may be located between about 300 to about 380 nucleotides upstream of the codon corresponding to the translational start of the EPSPS transit peptide or the first nucleotide of an intron or other untranslated leader sequence in the 5' untranslated region, and in a preferred embodiment of this alternative polynucleotide the 3' end of the enhancer, or first enhancer, is located between about 320 to about 350 nucleotides upstream of the codon corresponding to the translational start of the EPSPS transit peptide, or the first nucleotide of an intron or other untranslated leader sequence in the 5' untranslated region.

In the polynucleotide according to the invention, the region upstream of the promoter from the EPSPS gene may comprise at least one enhancer derived from a sequence which is upstream from the transcriptional start of a promoter selected from the group consisting of those of the actin, rolDFd, S-adenosyl homocysteinase, histone, tubulin, polyubiquitin and plastocyanin genes and the CaMV35S and FMV35S genes.

Accordingly the present inventive polynucleotide may comprise in the 5' to 3' direction a first enhancer comprising a transcriptional enhancing region derived from a sequence which is upstream from the transcriptional start of either the CaMV35S or FMV35S promoters, and a second enhancer comprising a transcriptional enhancing region derived from a sequence which is upstream from the transcriptional start of an actin gene.

Alternatively, the polynucleotide may comprise in the 5' to 3' direction a first enhancer comprising a transcriptional enhancing region derived from a sequence which is upstream from the transcriptional start of either the CaMV35S or FMV35S promoters, and a second enhancer comprising a transcriptional enhancing region derived from a sequence which is upstream from the transcriptional start of the rolDfd gene.

Alternatively, the polynucleotide may comprise in the 5' to 3' direction a first enhancer comprising a transcriptional enhancing region derived from a sequence which is upstream from the transcriptional start of either the CaMV35S or FMV35S promoters, and a second enhancer comprising a transcriptional enhancing region derived from a sequence which is upstream from the transcriptional start of a histone gene.

Alternatively, the polynucleotide may comprise in the 5' to 3' direction a first enhancer comprising a transcriptional enhancing region derived from a sequence which is upstream from the transcriptional start of either the CaMV35S or FMV35S promoters, and a second enhancer comprising a transcriptional enhancing region derived from a sequence which is upstream from the transcriptional start of a tubulin gene.

Alternatively, the polynucleotide may comprise in the 5' to 3' direction a first enhancer comprising a transcriptional enhancing region derived from a sequence which is upstream from the transcriptional start of the FMV35S promoter and a second enhancer comprising a transcriptional enhancing region derived from a sequence which is upstream is from the transcriptional start of the CaMV35S promoter.

Alternatively, the polynucleotide may comprise in the 5' to 3' direction a first enhancer comprising a transcriptional enhancing region derived from a sequence which is upstream from the transcriptional start of the CaMV35S promoter and a second enhancer comprising a transcriptional enhancing region derived from a sequence which is upstream from the transcriptional start of the FMV35S promoter.

Whatever the identity and juxtaposition of the various enhancers present in the polynucleotide, the nucleotides 5' of the codon which constitutes the translational start of the EPSPS chloroplast transit peptide may be Kozack preferred. What is meant by this is well known to the skilled man and will be further apparent from the examples below.

Particularly preferred embodiments of the present inventive polynucleotide comprise up stream of the sequence encoding the EPSPS chloroplast transit peptide a sequence encoding a non-translated 5' leader sequence derived from a relatively highly expressed gene, such as that of the glucanase, chalcone synthase and Rubisco genes.

The polynucleotide of the invention may also comprise a virally derived translational enhancer located within the non translated region 5' of the genomic sequence which encodes the EPSPS chloroplast transit peptide. The man skilled in the art is aware of the identity of such suitable translational enhancers—such as the Omega and Omega prime sequences derived from TMV and that derived from the tobacco etch virus, and how such translational enhancers can be introduced into the polynucleotide so as to provide for the desired result of increased protein expression.

The polynucleotide according to the invention may further comprise regions encoding proteins capable of conferring upon plant material containing it at least one of the following agronomically desirable traits: resistance to insects, fungi, viruses, bacteria, nematodes, stress, dessication, and herbicides. Whilst such a polynucleotide contemplates the herbicide resistance conferring gene being other than an EPSPS, such as glyphosate oxido-reductase (GOX) for example, the herbicide may be other than glyphosate in which case the resistance conferring genes may be selected from the group encoding the following proteins: phosphinothricin acetyl transferase (PAT), hydroxyphenyl pyruvate dioxygenase (HPPD), glutathione S transferase (GST), cytochrome P450, Acetyl-COA carboxylase (ACCase), Acetolactate synthase (ALS), protoporphyrinogen oxidase (PPO), dihydropteroate synthase, polyamine transport proteins, superoxide dismutase (SOD), bromoxynil nitrilase, phytoene desaturase (PDS), the product of the tfdA gene obtainable from *Alcaligeizes eutrophus*, and known mutagenised or otherwise modified variants of the said proteins. In the case that the polynucleotide provides for multiple herbicide resistance such herbicides may be selected from the group consisting of a dinitroaniline herbicide, triazolo-pyrimidines, a uracil, a phenylurea, a triketone, an isoxazole, an acetanilide, an oxadiazole, a triazinone, a sulfonanilide, an amide, an anilide, an isoxaflutole, a flurochloridone, a norflurazon, and a triazolinone type herbicide and the post-emergence herbicide is selected from the group consisting of glyphosate and salts thereof, glufosinate, asulam, bentazon, bialaphos, bromacil, sethoxydim or another cyclohexanedione, dicamba, fosaamine, flupoxam, phenoxy propionate, quizalofop or another aryloxy-phenoxypropanoate, picloram, fluormetron, atrazine or another triazine, metribuzin, chlorimuron, chlorsulfuron, flumetsulam, halosulffron, sulfometron, imazaquin, imazethapyr, isoxaben, imazamox, metosulam, pyrithrobac, rimsulfuron, bensulfuron, nicosulfuron, fomesafen, fluroglycofen, KIH9201, ET751, carfentrazone, mesotrione, sulcotrione, paraquat, diquat, bromoxynil and fenoxaprop.

A particular embodiment of the polynucleotide according to the invention provides for resistance to both-glyphosate and a protoporphyrinogen oxidase (PPGO) inhibitor, in particular butafenicil, for which the corresponding resistance protein is a PPGO or an inhibitor resistant variant thereof. A particularly preferred construct encoding such a herbicide resistance conferring combination comprises the EPSPS encoding sequence of the invention in combination with a sequence which encodes a PPDK or PPS in combination with a PPGO inhibitor resistant PPGO enzyme encoding sequence—such sequences being directed to the chloroplast—if desirable—by their autologous transit peptides and being under the expression control of non-heterologous promoters if the protein encoding sequences are of plant as opposed to bacterial origin.

In the case that the polynucleotide comprises sequences encoding insecticidal proteins, these proteins may be selected from the group consisting of crystal toxins derived from Bt, including secreted Bt toxins; protease inhibitors, lectins, Xenhorabdus/Photorhabdus toxins. The fungus resistance conferring genes may be selected from the group consisting of those encoding known AFPs, defensins, chitinases, glucanases, and Avr-Cf9. Particularly preferred insecticidal proteins are cry1Ac, cry1Ab, cry3A, Vip 1A, Vip 1B, Vip3A, Vip3B, cysteine protease inhibitors, and snowdrop lectin. In the case that the polynucleotide comprises bacterial resistance conferring genes these may be selected from the group consisting of those encoding cecropins and techyplesin and analogues thereof. Virus resistance conferring genes may be selected from the group consisting of those encoding virus coat proteins, movement proteins, viral replicases, and anti-sense and ribozyme sequences which are known to provide for virus resistance; whereas the stress, salt, and drought resistance conferring genes may be selected from those that encode Glutathione-S-transferase and peroxidase, the sequence which constitutes the known CBF1 regulatory sequence and genes which are known to provide for accumulation of trehalose.

The polynucleotide according to the invention may be modified to enhance expression of the protein encoding sequences comprised by it, in that mRNA instability motifs and/or fortuitous splice regions may be removed, or crop preferred codons may be used so that expression of the thus modified polynucleotide in a plant yields substantially similar protein having a substantially similar activity/function to that obtained by expression of the protein encoding regions of the unmodified polynucleotide in the organism in which such regions of the unmodified polynucleotide are endogenous. The degree of identity between the modified polynucleotide and a polynucleotide endogenously contained within the said plant and encoding substantially the same protein may be such as to prevent co-suppression between the modified and endogenous sequences. In this case the degree of identity between the sequences should preferably be less than about 70%.

The invention still further includes a biological or transformation vector comprising the present inventive polynucleotide. Accordingly, by "vector" is meant, inter alia, one of the following: a plasmid, virus, cosmid or a bacterium transformed or transfected so as to contain the polynucleotide.

The invention still further includes plant material which has been transformed with the said polynucleotide or vector, as well as such transformed plant material which has been, or is, further transformed with a polynucleotide comprising regions encoding proteins capable of conferring upon plant material containing it at least one of the following agronomically desirable traits: resistance to insects, fungi, viruses, bacteria, nematodes, stress, dessication, and herbicides.

The invention still further includes morphologically normal fertile whole plants which result from the crossing of plants which have been regenerated from material which has been transformed with the polynucleotide of the invention and plants which result from regeneration of material transformed with a polynucleotide which comprises a sequence which encodes a protein, such as a phosphoenolpyruvate synthase (PPS) or pyruvate orthophosphate di-kinase (PPDK) which proteins are capable of providing for elevated levels of phosphoenolpyruvate in the chloroplast. Such proteins are directed to the chloroplast by a suitable transit peptide—in the case of the PPDK enzyme preferably by the autologous peptide.

The invention still further includes morphologically normal fertile whole plants which contain the present inventive polynucleotide and which result from the crossing of plants which have been regenerated from material transformed with the present inventive polynucleotide or vector, and plants which have been transformed with a polynucleotide comprising regions encoding a CTP/PPS or CTP/PPDK, and/or regions encoding proteins capable of conferring upon plant material containing it at least one of the following agronomically desirable traits: resistance to insects, fungi, viruses, bacteria, nematodes, stress, dessication, and herbicides. The invention also includes progeny of the resultant plants, their seeds and parts.

Plants of the invention may be selected from the group consisting of field crops, fruits and vegetables such as canola, sunflower, tobacco, sugar beet, cotton, maize, wheat, barley, rice, sorghum, mangel worzels, tomato, mango, peach, apple, pear, strawberry, banana, melon, potato, carrot, lettuce, cabbage, onion, soya spp, sugar cane, pea, field beans, poplar, grape, citrus, alfalfa, rye, oats, turf and forage grasses, flax and oilseed rape, and nut producing plants insofar as they are not already specifically mentioned, their progeny, seeds and parts.

Particularly preferred such plants include soybean, canola, brassica, cotton, sugar beet, sunflower, peas, potatoes, and mangel wurzels.

The invention still further comprises a method of selectively controlling weeds in a field, the field comprising weeds and plants of the invention or the herbicide resistant progeny thereof, the method comprising application to the field of a glyphosate type herbicide in an amount sufficient to control the weeds without substantially affecting the plants. According to this method, one or more of a herbicide, insecticide, fungicide, nematicide, bacteriocide and an antiviral may be applied to the field (and thus the plants contained within it) either before or after application of the glyphosate herbicide.

The invention still further provides a method of producing plants which are substantially tolerant or substantially resistant to glyphosate herbicide, comprising the steps of:

(i) transforming plant material with the polynucleotide or vector of the invention;

(ii) selecting the thus transformed material; and (iii) regenerating the thus selected material into morphologically normal fertile whole plants.

The transformation may involve the introduction of the polynucleotide into the material by any known means, but in particular by: (i) biolistic bombardment of the material with particles coated with the polynucleotide; (ii) by impalement of the material on silicon carbide fibres which are coated with a solution comprising the polynucleotide; or (iii) by introduction of the polynucleotide or vector into *Agrobacterium* and co-cultivation of the thus transformed *Agrobacterium* with plant material which is thereby transformed and is subsequently regenerated. Plant transformation, selection and regeneration techniques, which may require routine modification in respect of a particular plant species, are well known to the skilled man. The thus transformed plant material may be selected by its resistance to glyphosate.

The invention still further provides the use of the present inventive polynucleotide or vector in the production of plant tissues and/or morphologically normal fertile whole plants which are substantially tolerant or substantially resistant to glyphosate herbicide.

The invention still farther includes a method of selecting biological material transformed so as to express a gene of interest, wherein the transformed material comprises the polynucleotide or vector of the invention, and wherein the selection comprises exposing the transformed material to glyphosate or a salt thereof, and selecting surviving material. The said material may be of plant origin, and may in particular be derived from a dicot selected from the group consisting of soybean, sugar beet, cotton and the *Brassicas*.

The invention still further includes a method for regenerating a fertile transformed plant to contain foreign DNA comprising the steps of:

(a) producing regenerable tissue from said plant to be transformed;

(b) transforming said regenerable tissue with said foreign DNA, wherein said foreign DNA comprises a selectable DNA sequence, wherein said sequence functions in a regenerable tissue as a selection device;

(c) between about one day to about 60 days after step (b), placing said regenerable tissue from step (b) in a medium capable of producing shoots from said tissue, wherein said medium may further contain a compound used to select regenerable tissue containing said selectable DNA sequence to allow identification or selection of the transformed regenerated tissue;

(d) after at least one shoot has formed from the selected tissue of step (c) transferring said shoot to a second medium capable of producing roots from said shoot to produce a plantlet, wherein the second medium optionally contains the said compound; and (e) growing said plantlet into a fertile transgenic plant wherein the foreign DNA is transmitted to progeny plants in Mendelian fashion, characterised in that the foreign DNA is, or the selectable DNA sequence comprised by the foreign DNA comprises, the polynucleotide according to the invention, and the said compound is glyphosate or a salt thereof. The plant may be a dicot as indicated above—more preferably selected from soybean, canola, brassica, cotton, sugar beet, sunflower, peas, potatoes and mangel worzel, and the said regenerable tissue may consist of embryogenic calli, somatic embryos, immature embryos etc.

The present invention also includes a diagnostic kit comprising means for detecting the present inventive enzyme or polynucleotide or enzymes encoded by it, and therefore suitable for identifing tissues or samples which contain these. The polynucleotides can be detected by PCR amplification as is known to the skilled man—based on primers which he can easily derive from the enzyme encoding sequences which are disclosed in this application. The enzymes per se can be detected by, for example, the use of antibodies which have been raised against them for diagnostically distinguishing the antigenic regions which they contain.

The present invention will be further apparent from the following description taken in conjunction with the associated drawings and sequence listings.

Of the Sequences:

| SEQ ID No. | | |
|---|---|---|
| 1 | depicts Brassicia napus genomic DNA. | |
| 2 | Bn EPSPS5 | (PCR primer) |
| 3 | Bn EPSPS3 | (PCR primer) |
| 4 | BnF1 | (PCR primer) |
| 5 | BnF2 | (PCR primer) |
| 6 | BnF3 | (PCR primer) |
| 7 | BnF4 | (PCR primer) |
| 8 | BnF5 | (PCR primer) |
| 9 | BnF6 | (PCR primer) |
| 10 | BnF7 | (PCR primer) |
| 11 | BnF8 | (PCR primer) |
| 12 | BnF9 | (PCR primer) |
| 13 | BnF10 | (PCR primer) |
| 14 | BnF11 | (PCR primer) |
| 15 | BnF12 | (PCR primer) |
| 16 | BnXho | (PCR primer) |
| 17 | BnMUTBot | (PCR primer) |
| 18 | BnMUTTop | (PCR primer) |
| 19 | BnNde | (PRC primer) |
| 20 | BnRBSEP | (PCR primer) |
| 21 | Brasr 12 | (PCR primer) |
| 22 | Brasr 11 | (PCR Primer) |
| 23 | Bnapus start rev | |
| 24 | Genome walker 1 | |
| 25 | Genome walker 2 | |
| 26 | CaMV343 | (PCR primer) |
| 27 | CaMV46C | (PCR primer) |
| 28 | BnGUSXMa | (PCR primer) |
| 29 | FMV enhancer | |
| 30 | CaMV35S enhancer | |
| 31 | Soybean Genomic EPSPS Sequence clone 1/14 | |
| 32 | Soybean Genomic EPSPS Sequence clone 1/12 | |
| 33 | EPSPS 10 reverse | (PCR primer) |
| 34 | EPSPS 4 forward | (PCR primer) |
| 35 | SEQ ID No. 31 containing double mutation | |
| 36 | SEQ ID No. 32 containing double mutation | |
| 37 | FMV35S90 enhancer | |
| 38 | FMV35S46 enhancer | |
| 39 | Gm Term Bam | (PCR primer) |
| 40 | Gm Term Eco | (PCR primer) |
| 41 | BnMUT2PST | (PCR primer) |
| 42 | BnMUTKPN | (PCR primer) |
| 43 | GmRubPac | (PCR primer) |
| 44 | GmRubbot | (PCR primer) |
| 45 | GmRubtop | (PCR primer) |
| 46 | GmRubKpn | (PCR primer) |
| 47 | ZMPPDK1 | (PCR primer) |
| 48 | ZMPPDK2 | (PCR primer) |
| 49 | ECPPS1 | (PCR primer) |
| 50 | ECPPS2 | (PCR primer) |
| 51–65 | Motifs present in the stable EPSPS proteins of the invention | |

EXAMPLES

Figure 1:
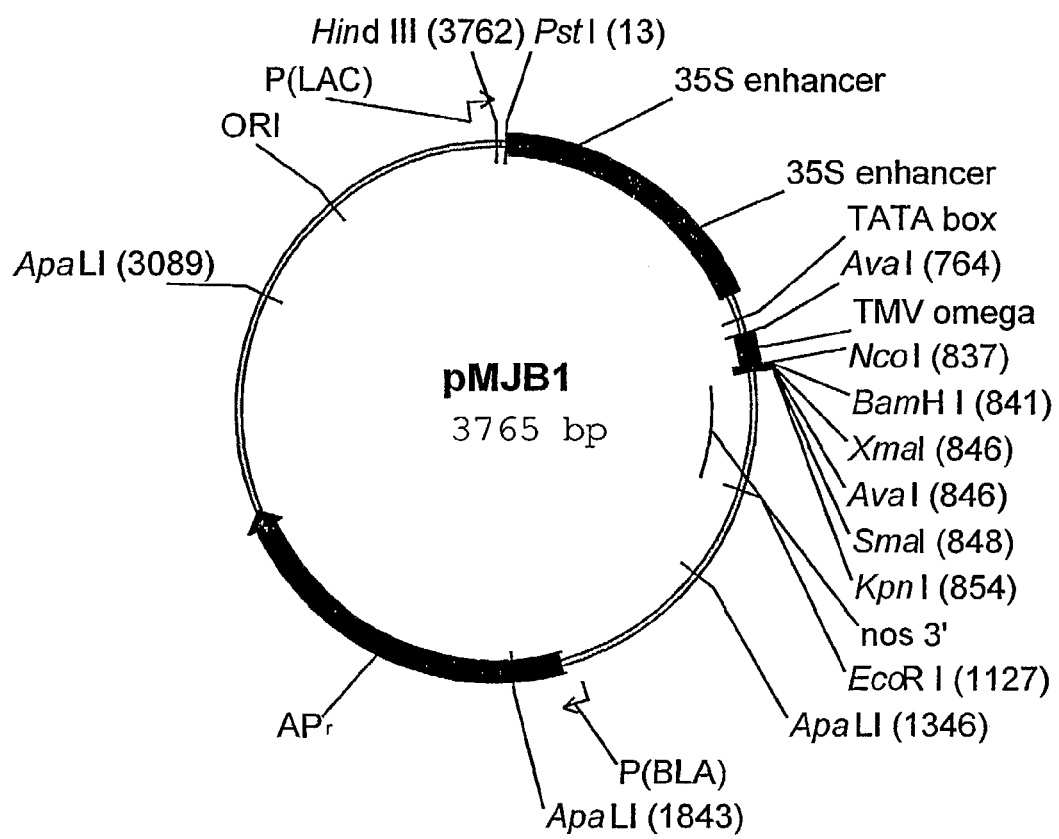
FIG. 1 shows a schematic representation of vector pMJB1.

Methods useful for cloning, expressing and characterising the stable glyphosate-resistant EPSP synthases of the current invention are described herein Stable glyphosate-resistant EPSPSs of the current invention are characterised as being stable (retaining >~80% of their catalytic activity) after being incubated in a suitable buffer at 37 C for at least 4 hours. As exemplified below, enzyme stability experiments can suitably be carried out using substantially purified, part purified or crude preparations of enzyme extracts (for example the latter are readily obtained as extracts of transgenic plants engineered to express the glyphosate-resistant EPSPS or, similarly, extracts of microbes engineered to express a transgene encoding the glyphosate-resistant EPSPS). Ideally, glyphosate-resistant enzymes are tested for stability both in a purified form and then as purified protein spiked back into a crude plant extract so as to test them under more realistic in planta-like conditions. In such extracts, the enzyme activity due to glyphosate-resistant EPSPS can easily be discriminated from background susceptible endogenous EPSPS by testing activity over a range of glyphosate concentrations. At a discriminating concentration of glyphosate (e.g. 0.1 mM glyphosate in the presence of 0.1 mM PEP) virtually all of the measured activity will originate from the resistant enzyme Example 1

Method for Identification of Stable Glyphosate-resistant EPSP Synthases

In order to test the stability of a glyphosate-resistant EPSPS, a test solution of the enzyme (prepared as described below in buffer at pH ~7.0–7.5 and in purified or part purified form) is heated to 37 C for 4–5 h. The glyphosate-resistant activity of the heated enzyme is then compared with the activity of a) a sample similarly prepared but kept at ice temperature and b) a similar sample but freshly prepared.

Stable glyphosate resistant enzymes of the current invention are characterised by the fact that, following incubation for 5 h at 37 C, they lose little, if any, of their original glyphosate-resistant catalytic activity (<20%, preferably <15% and more preferably <10%) relative to suitable controls when assayed as described below. Preferably the stability experiment is carried out using substantially pure enzyme although a very similar result will normally be obtained using crude preparations, or when pure protein is spiked back into crude extract. Methods suitably used for assay and preparation of enzyme extracts are further detailed below. The stability of the glyphosate-resistant EPSPS can suitably be assessed in a variety of other, essentially equivalent ways (for example by heating the enzyme at a slightly higher temperature for a shorter time or a lower temperature for a longer period . . . e.g at 25 C for 3 d).

Example 2

Method for assaying EPSPS Activity and Determination of Kinetic Constants.

Assays are carried out generally according to the radiochemical method of Padgette et al 1987 (Archives of Biochemistry and Biophysics, 258(2) 564–573) with K+ions as the major species of cationic counterion. Assays in a total volume of 50 μl, in 50 mM Hepes(KOH) pH 7.0 at 25° C., contain purified enzyme or plant extract (see below) diluted appropriately in Hepes pH 7.0 containing 10% glycerol, and 5 mM DTT, $^{14}C$ PEP either as variable-substrate (for kinetic determinations) or fixed at 100 or 250 μM and shikimate 3 Phosphate (K+ salt) at 0.75 or 2 mM as indicated. Optionally, for assays of crude plant extracts, assays also contain 5 mM KF and/or 0.1 mM ammonium molybdate. Assays are started with the addition of $^{14}C$ phosphoenolpyruvate (cyclohexylammonium+salt) and stopped after 2–10 minutes (2 minutes is preferable) with the addition of 50 μl of a solution of 1 part 1M acetic acid and 9 parts ethanol. After stopping, 20 μl is loaded onto a synchropak AX100 (25 cm×4.6 mm) column and chromatographed using isocratic elution with a 0.28M potassium phosphate pH 6.5 mobile phase flowing at 0.5 ml/min over 35 minutes. Under these conditions the retention times for PEP and EPSP are, depending on the individual columns, ~19 and 25 minutes respectively. A CP 525TR scintillation counter is connected to the end of the AX 100 column. It is fitted with a 0.5 ml flow cell, and the flow rate of scintillant (Ultima Flo AP) is set at 1 ml/min. Relative peak areas of PEP and EPSP are integrated to determine the percentage conversion of labelled PEP to EPSP. Apparent $K_m$ and Vmax values are determined by least squares fit to a hyperbola with simple weighting using the Grafit 3.09b from Erithacus Software Ltd. Km values are generally ascertained using 8–9 concentrations of variable substrate ranging from $K_m/2$–10 $K_m$ and triplicate points. Except where specifically noted, data points are only included in the analysis where there is <30% conversion of substrate to EPSP.

Shikimate-3-Pi (S3P) is prepared as follows, To 7 mls of 0.3M TAPS pH 8.5 containing 0.05M Shikimate, 0.0665M ATP (Na salt), 10 mM KF, 5 mM DTT, and 0.05M $MgCl_2.6H_2O$, 75 μl of a 77 unit (μmol $min^{-1}$) $ml^{-1}$ solution of shikimate kinase is added. After 24 hrs at room temperature, the reaction is stopped by brief heating to 95° C. The reaction solution is diluted 50 fold in 0.01M Tris HCl pH 9, and chromatographed by anion exchange on Dowex 1 X 8–400, using a 0–0.34M $LiCl_2$ gradient. The S3P fractions are combined, freeze dried, and then redissolved in 7 mls distilled $H_2O$. 28 mls of 0.1M $Ba(CH_3COOH)_2$ and 189 mls of absolute ethanol are then added. This solution is left to stir overnight at 4° C. The resulting precipitate of tri-Barium S3P is collected and washed in 30 mls of 67% ethanol. The washed precipitate is then dissolved in ~30 mls distilled $H_2O$. By adding $K_2SO_4$ the $K^+$ salt of S3P is produced as required. Great care is taken to add a minimal excess of sulphate. The $BaSO_4$ precipitate is removed and the supernatant containing the required salt of S3P freeze dried. Each salt is weighed and analysed by proton NMR. S3P preparations so-prepared are >90% pure according to proton NMR and, according to their weights and integration of 31P NMR, contain only low residues of potassium sulphate.

Example 3

Preparation of Extracts of Plant Material Suitable for EPSPS Assay

Callus or plantlet material (0.5–1.0 g) is ground to a fine frozen powder in a liquid nitrogen-chilled mortar and pestle. This powder is taken up in an equal volume of a suitable chilled extraction buffer (for example, 50 mM Hepes/KOH buffer at pH 7.5 containing 1 mM EDTA, 3 mM DTT, 1.7 mM ‘pefabloc’ (serine protease inhibitor), 1.5 mM leupeptin, 1.5 mM pepstatin A, 10% v/v glycerol and 1% polyvinylpyrolidone), resuspended, mixed and centrifuged in a chilled centrifuge to bring down debris. The supernatant is exchanged down a chilled PD10 column of Sephadex G25 into 25 mM Hepes/KOH buffer at pH 7.5 containing 1 mM EDTA, 3 mM DTT and 10% v/v glycerol. Protein is estimated by the Bradford method standardised using bovine serum albumen. A portion of the extract is frozen in liquid nitrogen; a portion is assayed immediately.

Example 4

Method for Assaying EPSPS Activities in Crude Plant Materials and Discriminating the Proportion of the Total which is Resistant to Glyphosate EPSPS assays of plant extracts are carried out, as described above, with 0.1 mM $^{14}$C-PEP and 0.75 mM shikimate-3-Pi either in the absence or the presence of 0.1 mM N-(phosphonomethyl)glycine. Under these assay conditions, the resistant forms of EPSPS of the current invention are estimated to be inhibited by <8.5% whilst the sensitive w/t form is essentially fully inhibited (>98%). Thus, the level of activity observed in the presence of glyphosate (A) is taken to represent ~92% of the level of resistant enzyme derived from expression of the transgene whilst the level of susceptible w/t EPSPS is taken to be the total level of EPSPS activity observed in the absence of glyphosate minus the value of A x~1.08. Because the Vmax of the mutant enzymes of the current invention are estimated to be, for example, only about a third of the Vmax of the w/t enzyme (and because the Km values for PEP of both w/t and mutant forms are estimated to be about 20 µM or less), the level of expression of the mutant enzyme polypeptide relative to the level of expression of the endogenous w/t EPSPS is taken, to be about three fold higher than the ratio calculated on the basis of the ratio of their relative observed activities. The total level of EPSPS polypeptide expression (mutant+w/t) is also estimated by Western blotting.

Example 5

Cloning and Expression of w/t cDNA Encoding Mature *Brassica napus* EPSPS in *E.coli*

*Brassica napus* EPSPS cDNA is amplified using RT-PCR from RNA isolated from glass-house grown *Brassica napus* plants using Superscript RT from BRL according to the recommendation supplied by the manufacturer. PCR is performed using Pfu turbo polymerase from Stratagene according to the methods supplied by the manufacturer. Suitably designed oligonucleotide primers based on the known nucleotide sequence (EMBL accession X51475) are used in the amplification reaction and the reverse transcription steps. The PCR product is cloned into pCRBlunt II using Invitrogens Zero Blunt TOPO kit. The sequence of the insert is confirmed by sequencing and it is verified that the predicted open reading frame corresponds to that of the predicted mature chloroplastic *Brassica napus* EPSPS protein with the exception of the presence of an initiating Met. The cloned and verified EPSPS sequence is excised using suitable restriction enzymes as known in the art and the purified fragment is cloned into pET24a (Novagen) digested similarly. The recombinant clones are introduced into BL21 (DE3) a codon-optimised RP strain of *E.coli* supplied by Stratagene. The EPSPS protein is expressed in this strain following addition of 1 mM IPTG to the fermenter medium (LB supplemented with 100 ug/ml Kanamycin). The recombinant protein of the correct predicted mass is identified (i) on the basis of Coomassie staining of SDS gels of cell extracts and side by side comparison with Coomassie-stained gels of extracts of similar *E.coli* cells transformed with an empty pET24a vector and ii) by western analysis using a polyclonal antibody raised to previously-purified plant EPSPS protein.

Example 6

Cloning and Expression in *E.coli* of Glyphosate-resistant Mutant *Brassica napus* EPSPS The *Brassica napus* EPSPS cDNA in pCRBlunt is used as a template for two further PCR using primer pairs designed to introduce specific changes such that the resulting reaction product encodes a modified EPSPS protein wherein a first position is mutated so that the residue at this position is Ile rather than Thr and a second position is mutated so that the residue at this position is Ser rather than Pro, the mutations being introduced into EPSPS sequences which comprise the conserved region GNAGTAMRPLTAAV (SEQ ID NO: 69) in the wild type enzyme such that the modified sequence reads GNAGIAMRSLTAAV (SEQ ID NO: 70). The sequence of *Brassica napus* EPSPS gene is known and methods for designing primers to effect this mutagenesis are well-known in the art.

The resultant PCR product is gel purified and cloned into pCRBlunt II using Invitrogens Zero Blunt TOPO kit. It is confirmed that the DNA sequence of the insert and its predicted open reading frame correspond to that of the predicted mature chloroplastic *Brassica napus* EPSPS protein (with the exception of the presence of an initiating Met) and also that the desired changes (the specific mutation of T to I and P to S at specific positions in the EPSPS sequence) are encoded. The thus cloned and verified *B.napus* EPSPS sequence is excised using suitable restriction enzymes and the purified fragment cloned into pET24a (Novagen) digested similarly. The recombinant clones are introduced into BL21 (DE3), a codon optimised RP strain of *E.coli* supplied by Stratagene. The EPSPS protein is expressed in this strain following addition of 1 mM IPTG to the fermenter medium (LB supplemented with 100 ug/ml Kanamycin). The recombinant protein of the correct predicted mass is identified i) on the basis of Coomassie staining of SDS gels of cell extracts and side by side comparison with Coomassie-stained gels of extracts of similar *E.coli* cells transformed with an empty pET24a vector and ii) by Western analysis using a polyclonal antibody raised to previously-purified plant EPSPS protein. This mutant form of *Brassica napus* EPSPS is purified and characterised as described herein.

Example 7

Purification and Characterisation of Mutant *Brassica napus* EPSPS

The mature mutant *Brassica napus* EPSPS protein is purified at ~4 C as follows. 25 g wet weight of cells are washed in 50 ml of 0.1M Hepes/KOH buffer at pH 7.5 containing 5 mM DTT, 2 mM EDTA and 20% v/v glycerol. Following low-speed centrifugation, the cell pellet is resuspended in 50 ml of the same buffer but also containing 2 mM of 'Pefabloc' a serine protease inhibitor. Cells are evenly suspended using a glass homogenizer and then disrupted at 10000 psi using a Constant Systems (Budbrooke Rd, Warwick, U.K.) Basic Z cell disrupter. The crude extract is centrifuged at ~30,000 g for 1 h and the pellet discarded. Protamine sulphate (salmine) is added to a final concentration of 0.2%, mixed and the solution left to stand for 30 min. Precipitated material is removed by centrifugation for 30 min at ~30,000 g. Aristar grade ammonium sulfate is added to a final concentration of 40% of saturation, stirred for 30 min and then centrifuged at ~27,000 g for 30 min. The pellet is resuspended in ~10 ml of the same buffer as used for cell disruption, further ammonium sulfate is added to bring the solution to ~70% of saturation, the solution is stirred for 30 min and centrifuged again to yield a pellet which is resuspended in ~15 ml of S200 buffer (10 mM Hepes/KOH (pH 7.8) containing 1 mM DTT, 1 mM EDTA and 20% v/v glycerol). This is filtered (0.45 micron) loaded and chromatographed down a K26/60 column containing Superdex 200 equilibrated with S200 buffer. EPSPS-containing fractions detected on the basis of EPSPS enzyme activity are combined and loaded onto an xk16 column containing 20 ml of HP Q-Sepharose equilibrated with S200 buffer. The column is washed with S200 buffer and then EPSPS eluted within a linear gradient developed from 0.0M to 0.2M KCl in the same buffer. EPSPS elutes within a single peak corresponding to a salt concentration at or below approximately 0.1 M. EPSPS-containing fractions detected on the basis of EPSPS enzyme activity are combined and loaded onto a HiLoad xk26/60 column of Superdex 75 equilibrated with Superdex 75 buffer (25 mM Hepes/KOH (pH 7.5) containing 2 mM DTT, 1 mM EDTA and 10% v/v glycerol. EPSPS-containing fractions identified on the basis of enzyme activity are combined and loaded onto a 1 ml column of MonoQ equilibrated with the same, Superdex 75 buffer. The column is washed with starting buffer and EPSPS eluted as a single peak over the course of a 15 ml linear gradient developed between 0.0 and 0.2M KCl. EPSPS is obtained near (>90%) pure at this stage in the purification. Optionally, EPSPS is further purified by exchange into Superdex 75 buffer containing 1.0 M (Aristar) ammonium sulphate and loading onto a 10 ml column of phenyl sepharose equilibrated in the same buffer. EPSPS is eluted as a single peak early during the course of a linear gradient of declining ammonium sulphate developed between 1.0 and 0.0 M ammonium sulphate.

The purified mutant form of *Brassica napus* EPSPS, obtained by these or by similar methods and assayed as described above in the presence of 2 mM shikimate-3-Pi, has an apparent Vmax of ~5 µmol/min/mg and a Km for PEP of ~25 µM. At 40 µM PEP, the IC50 value for the potassium salt of glyphosate is ~0.6 mM. The estimated Ki value for potassium glyphosate of the mutant EPSPS is ~0.45 mM.

Example 8

Cloning of Genomic DNA Encoding *Brassica napus* EPSPS

A *Brassica napus* genomic DNA fragment (SEQ ID No.1), encoding EPSPS is known in the art (Gasser and Klee, 1990). PCR primers BnEPSPS5 (SEQ ID No.2) and BnEPSPS3 (SEQ ID No.3) are used to amplify the EPSPS gene from genomic DNA isolated from *Brassica napus* var. Westar.
Pfu polymerase is used to perform the PCR using the following conditions:
94° C. 5 min
94° C. 1 min
55° C. 30 s
72° C. 12 min The resulting 3.8 Kb product is cloned into pCR4Blunt-Topo and sequenced using the following primers: M13Forward, M13Reverse (Invitrogen), BnF1 (SEQ ID No.4), BnF2 (SEQ ID No.5), BnF3 (SEQ ID No.6), BnF4 (SEQ ID No.7), BnF5 (SEQ ID No.8), BnF6 (SEQ ID No.9), BnF7 (SEQ ID No.10), BnF8 (SEQ ID No.11), BnF9 (SEQ ID No.12), BnF10 (SEQ ID No.13), BnF11 (SEQ ID No.14) and BnF12 (SEQ ID No.15).

Example 9

Introduction of Mutations into Genomic DNA Encoding BnEPSPS

The desired Thr-Ile and Pro-Ser mutations are introduced into the *B. napus* EPSPS gene by PCR using oligonucleotide primers containing codon changes so as to introduce the desired amino acid changes. Primers BnXho (SEQ ID No.16) and BnMUTBot (SEQ ID No.17) are used to amplify a desired region of EPSPS from Westar genomic DNA. Likewise, primers BnMutTop (SEQ ID No.18) and BnNde (SEQ ID No.19) are used to amplify an additional region from Westar genonic DNA. 1 ul of each of the PCR products is mixed and overlapping complementary sequences allowed to anneal. The products are then joined by PCR using primers BXho and BnNde. The resulting PCR product is cloned and sequenced to check for the inclusion of the double mutation. The Xho1/Nde1 fragment in the BnEPSPS clone is excised and replace with the cloned Xho1/Nde1 fragment containing the double mutant.

Example 10

Construct for Expression of Mutant *B. napus* EPSPS in Plants Having the Rubisco Leader Sequence Upstream of the Gene Encoding Mutant *Brassica napus* EPSPS The tobacco rubisco leader is introduced into the construct by PCR. Primers BnRBSEP (SEQ ID No.20) and Brasr12 (SEQ ID No.21) are used to amplify a product from 50 ng wildtype *B. napus* genomic DNA as template using Pfu-Turbo polymerase. The resulting PCR product is cloned into pCR4 blunt TOPO and clones are identified by restrictions digest that are orientated such as it may be excised as Not1 (from vector) and Xho1. The rubisco leader is then introduced into the mutated BnEPSPS clone as Not1/Xho1.

Example 11

Identification of the *Brassica napus* EPSPS Promoter (Useful for Expression of EPSPS in Plants) by Genome Walking Increased lengths of upstream or downstream sequence of any plant gene may be obtained using the genome walking kit as supplied and directed by Clontech. The primers depicted in SEQ ID Nos 22 and 23 (Bras r11 and Bnapus start rev) are used to obtain upstream sequence of the *Brasicca napus* EPSPS gene using *Brasicca napus* genomic DNA according to the methods described in the protocol accompanying the genome walker kit.

The Bras r11 (SEQ ID No.22) primer is used in conjunction with the AP1 primer supplied in the genome walker kit and the Bnapus start rev primer is used with the AP2 primer supplied with the genome walker kit. Products are cloned into pCR-TOPO using a TOPO TA Cloning kit from Invitrogen according to the manufacturers instructions. PCR using M13 forward and reverse primers is performed using Ready to Go Beads from Pharmacia to ascertain which clones contain inserts of the correct size. A number of these clones are used to make DNA preps and these DNAs are then used to determine the nucleotide sequence of the inserts.

A second set of primers (SEQ ID Nos.24 and 25 respectively) is used for a further walk as shown below:
Genome walker 1 (SEQ ID No.24) with the AP1 primer
Genome walker 2 (SEQ ID No.25) with the AP2 primer Additional genomic digests are performed in addition to those recommended by Clontech's protocols. These digests include Alu I, Hae III, Hinc II and Rsa I. These digested DNAs are then treated identically to the other digests performed as described by the protocols accompanying the Genome walking kit. This is done to increase the chance of getting a correct and long PCR product. Again the PCR products are cloned into pCR-TOPO using a TOPO TA Cloning kit from Invitrogen according to the manufactures instructions and sequence determination is performed on random clones obtained from each cloned product that contain inserts of the correct size. The sequence of the inserts are determined. Approximately 1 kb of sequence upstream form the translational start site of the *Brasicca napus* EPSPS is obtained that is contiguous with the published sequence.

Example 12

Constructs for Expression of Mutant *Brassica napus* EPSPS in Plants

The 35S enhancer is amplified from vector pMJB1 (FIG. 1) by PCR using primers CaMV343 and CaMV46C (SEQ ID Nos.26 and 27 respectively)

The PCR product is cloned into vector pCR4Blunt-TOPO and sequenced. The desired promoter, obtained as described in the previous example is amplified from *B. napus* Westar genomic DNA using a 5' primer containing a Sph1 site and BnGUSXma (SEQ ID No.28)

Figure 2:
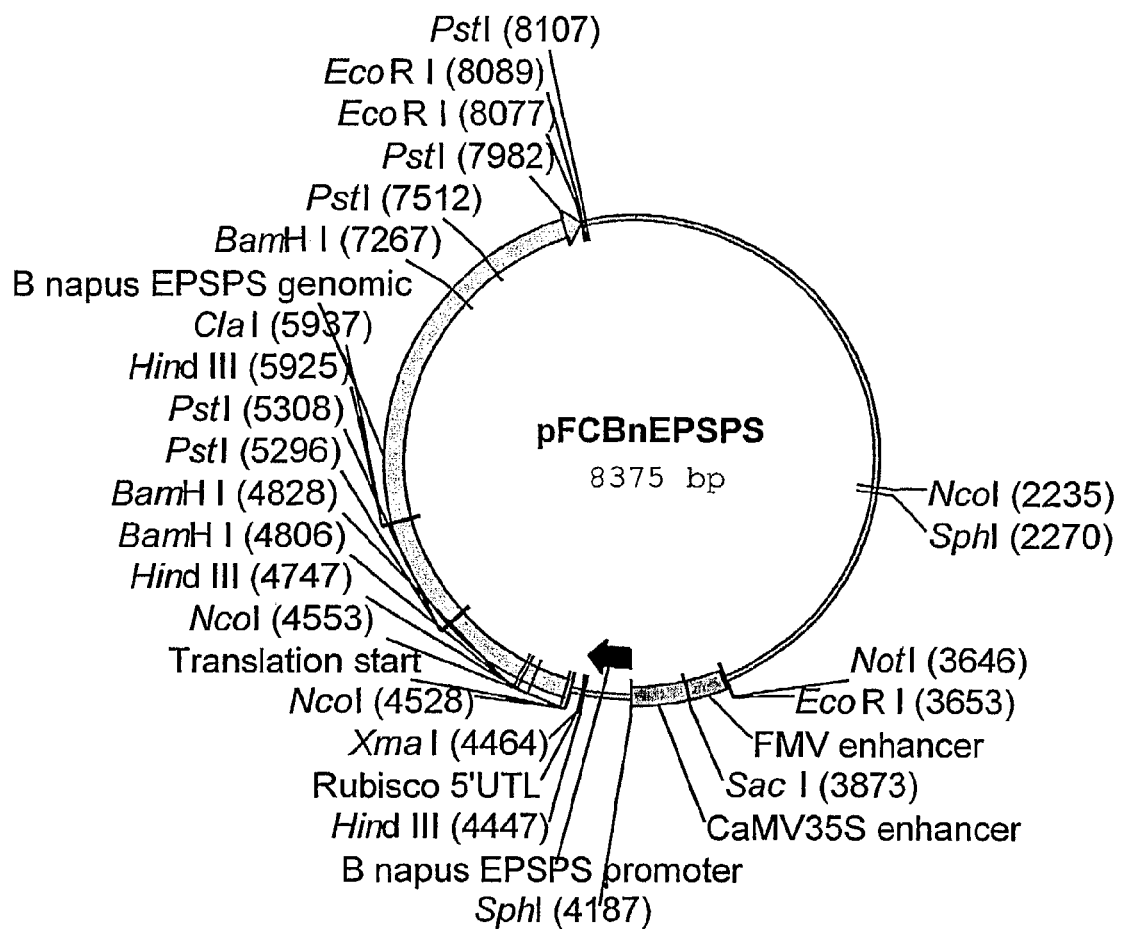
FIG. 2 shows a schematic representation of vector pFCB-nEPSPS.

The PCR product is digested directly with Sph1 and Xma1 and ligated into the pCR4Blunt-TOPO vector containing the 35S enhancer as Sph1/Xma1 (partial digest with Sph 1). The CaMV35S enhancer fused to the BnEPSPS promoter is then excised from pCR4-Blunt using Not1 (from vector) and Xma 1 and cloned into the PCR4Blunt vector containing the tobacco rubisco leader and mutated *B. napus* EPSPS gene. The FMV enhancer (SEQ ID No.29) or the CaMV35S enhancer (SEQ ID No.30) is synthesised chemically and subcloned into vector pCR4 Blunt TOPO. The FMV enhancer is excised from PCR4-Blunt as Not1/Sac1 and ligated into the CaMV35S enhancer/*B. napus* promoter/rubisco leader/*B. napus* EPSPS as Not1/Sac1. The final construct is shown in FIG. 2. The whole expression cassette may be excised using EcoR1 and ligated into a suitable vector for plant transformation.

Example 13

Plant Transformation and Regeneration

The expression cassette is excised from the pFCBnEPSPS vector using EcoR1 and ligated into, for example, a binary vector pBin19 at the unique EcoR1 restriction site. The binary vector, containing the desired expression cassette transformed into *Agrobacterium tumefaciens* strain LBA 4404 using the freeze thaw method of transformation provided by Holsters et al., 1978. Tobacco transformation and whole plant regeneration is performed using *Nicotiana tabacum* var. Samsun according to protocols in Draper et al (Plant Genetic Transformation, Blackwell Sci. Pub. 1989). Transformation events are selected on MS-media containing kanamycin. Alternatively pFCBnEPSPS, or other constructs capable of delivering glyphosate resistance in plants by the expression of a glyphosate resistant EPSPS gene from soybean may be introduced into plants directly without using *Agrobacterium* mediated techniques as described for Soybean.

Constructs are transformed into regenerable embryogenic soyabean tissues using either biolistic type approaches (e.g Santarem E R, Finer, J. J (1999) 'Transformation of soyabean (*Glycine max* (L.) Merrill) using proliferative embryogenic tissue maintained on a semi-solid medium' In vitro Cellular and Developmental Biology-Plant 35, 451–455; U.S. Pat. Nos. 5,503,998, 5,830,728) or via infection with *Agrobacterium* (e.g. U.S. Pat. Nos. 5,024,944, 5,959,179). Regenerable embryogenic soyabean tissues are derived, for example, from the cotyledons of immature embryos or other suitable tissues.

Proliferative embryogenic tissue can, for example, be maintained on a semi-solid medium. Such tissue, is, for example obtained in the following way. Immature zygotic embryos which are 3–4 mm long are isolated from pods of, for example, *Glycine max* (L.) Merrill, 2–3 weeks after flower formation. Pods can be checked for the presence of embryos of the correct length and maturity by 'backlighting'. Pods are then sterilized. Immature embryos are removed and the axis removed from each. Immature embryos are then plated on 'D40-Lite' semi-solid (0.2% gelrite) MS salts medium at pH 7.0 containing B5 vitamins, 3% sucrose and 40 mg/l 2,4-D for 3–4 weeks. For proliferation of embryos the material is then transferred to 'D20' MS salts medium at pH 5.7 containing B5 vitamins, 3% sucrose, 20 mg/l 2,4-D and 0.2% Gelrite. Material with bright green globular proliferative embryos is selected and subcultured every 2–3 weeks.

For bombardment, 20–25 clumps/plate of tissue are selected (subcultured 4–5 days prior to bombardment) and arranged in the centre of the dish containing D20 medium. The tissue is dried for 15 min by uncovering for 15 minutes under a sterile hood. Gold particles coated in DNA construct (coated, for example, using methods described in the references above) are twice bombarded into the tissue on D20 medium using any one of a large number of commercially available guns. By way of further example a PDS1000 particle gun is used. Particles may be prepared and coated with DNA in a similar manner to that described by Klein et al 1987, Nature, 327, 70–73. Alternatively, for example, 60 mg of gold or tungsten particles (~1.0 μm) in a microcentriftge tube are washed repeatedly in HPLC-grade ethanol and then, repeatedly, in sterile water. The particles are resuspended in 1 ml of sterile water and dispensed into 50 μl aliquots in microcentrifuge tubes. Gold particles are stored at 4 C, tungsten particles at −20 C. 3 mg of DNA are added to each aliquot of (defrosted) particles and the tubes are vortexed at top speed. Whilst maintaining near continuous vortexing, 50 μl of 2.5M $CaCl_2$ and 20 μl of 0.1M spermidine is added. After 10 minutes of further vortexing, samples are centrifuged for 5 seconds in an eppendorf microcentrifuge, the supernatant is drawn off and the particles washed in successive additions of HPLC-grade ethanol. The particles are thoroughly resuspended in 60 μl of ethanol and then dispensed in 10 μl aliquots onto the surface of each macrocarrier to be used in the PDS1000 particle gun. Components of the PDS1000 particle gun are surface sterilised by immersion in 70% ethanol and air-drying. Target plates prepared, as described above, with tissue arranged into an ~2.5 cm disc are placed 6 cm from the stopping screen. Suitably chosen rupture discs are then used for bombardment.

One week after bombardment, all tissue clumps are transferred onto D20 medium, buffered to pH 5.7, containing a suitable selective concentration of glyphosate between 0.05 and 5 mM. After an additional 3–4 weeks all tissue is transferred to fresh D20 medium containing an increased concentration of glyphosate within this concentration range. After a further 3–4 weeks, living tissue is selected and subcultured on every 3–4 weeks in similar D20 medium containing glyphosate. Alternatively, in the case that some other selectable marker than glyphosate is also present then selections may be made as appropriate (e.g using increasing concentrations of hygromycin). Growing sections are thus maintained and, given enough tissue, may be analysed by PCR to confirm that they are transgenic for the desired DNA.

In order to develop and mature embryos, tissue clumps are placed onto M6 medium which comprises MS salts at pH 5.7 containing B5 vitamins, 6% maltose and 0.2% gelrite. 6–9 clumps are placed in a tall dish at 23° C. After 3–4 weeks, embryos elongate and can be separated and transferred to another round of incubation on M6 medium. After 4–6 weeks, embryos are cream-coloured and ready for desiccation. 9 such cream-coloured embryos are placed in a dry Petri dish, sealed with parafilm and placed onto a shelf for 2–3 days. Embryos should be somewhat flaccid and not "crispy-crunchy".

Dessicated embryos can be germinated by plating onto OMS (growth regulator-free MS medium). Following germination which normally occurs within a week plants are transferred to larger boxes and, once there is sufficient root and shoot formation, thence to soil. To prevent fungal contamination it is advisable to wash OMS from the roots with is distilled water. Plants may be kept and grown under high humidity and, initially, under 24 hour lighting. Plants may be grown until about 2 feet tall under 24 hour lighting and then encouraged to flower and form pods through a shift to a 16 hour lighting regime. Seeds are collected and progeny grown on, crossed and backcrossed into order to move the transgenes into the desired plant background using the normal methods of plant breeding. Plants are routinely analysed for the presence and expression of transgenes using the normal methods of molecular biology including analysis by PCR, Southern, Western, ELISA and enzyme assay techniques.

Example 14

Methods of Obtaining, Genes Encoding Stable Glyphosate Resistant EPSPs

In one embodiment of the current invention, glyphosate resistant EPSPS genes suitable for expression in *E.coli* are constructed, as for example, described herein where, in the coding sequence a first position is mutated so that the residue at this position is Ile rather than Thr and a second position is mutated so that the residue at this position is Ser rather than Pro, the mutations being introduced into EPSPS sequences which comprise the following conserved region GNAGTAMRPL (SEQ ID NO: 66) in the wild type enzyme such that the modified sequence reads GNAGIAMRSL (SEQ ID NO: 67).

Stable glyphosate-resistant EPSP synthases of the current invention and genes encoding these are then obtained by generating a wide range of variants by a process of random or partially random mutagenesis (for example using chemical or UV mutagenesis, by using a non-proof reading DNA polymerase (e.g. in a strain such as XL1 red) or by using any one of a number of 'directed evolution' approaches (e.g as reviewed by Kuchner and Arnold, 1997 in TIBTECH, 15, 523–530 or described by Stemmer (1994) in PNAS, 91, 10747–10751) and selecting genes expressing EPSPSs which are stable and which remain glyphosate resistant.

Suitable means of selection include, for example, expression of mutated genes (e.g from a weak constitutive promoter) in an Aro A– strain of *E.coli* grown at elevated temperatures (e.g 37–42 C) and selecting those transformants most capable of growth in minimal medium (optionally also containing glyphosate). Alternatively, a non-aro A host strain might be used (preferably e.g. rec A) provided that the medium contains a selective concentration of glyphosate. The skilled man will recognise that many methods of mutagenesis and selection could be used within the ambit of the current invention.

Example 15

Stable Glyphosate-resistant EPSPSs and Genes Encoding them

The stable double mutant form of *Brassica napus* EPSPS is one example of the current invention. The skilled man will recognise that other examples of such EPSPSs of the current invention and genes encoding them can be cloned, isolated and characterised using methods the same or similar to those described above.

In EPSPSs and the EPSPS gene sequences of the current invention, the coding sequence at a first position is mutated so that the residue at this position is Ile rather than Thr and a second position is mutated so that the residue at this position is Ser rather than Pro, the mutations being introduced into EPSPS sequences which comprise the following conserved region GNAGTAMRPL (SEQ ID NO: 66) in the wild type enzyme such that the modified sequence reads GNAGIAMRSL (SEQ ID NO: 67).

EPSPS protein sequences of the current invention are further characterised in that they DO NOT comprise a region having the sequence K(A/V)AKRAVVVGCGGKFPVE (SEQ ID NO: 68)

EPSPS protein sequences of the current invention are furter characterised in that they comprise at least one of the amino acid sequence motifs listed below in (i)→(viii).

| | | | |
|---|---|---|---|
| (i) | ALLMZAPLA | (SEQ ID NO:51) where Z is NOT S or T |
| (ii) | EIEIZDKL | (SEQ ID NO:52) where Z is NOT V |
| (iii) | FG(V/I)(K/S)ZEH | (SEQ ID NO:53) where Z is NOT V |
| (iv) | AL(K/R)ZLGL | (SEQ ID NO:54) where Z is NOT R |
| (v) | GLXVEZ$_1$DXZ$_2$XXXA(I/V)V | (SEQ ID NO:55) where Z$_1$ is NOT T and/ or Z$_2$ is NOT E |
| (vi) | ITPPZ$_1$K(L/V)(K/N)Z$_2$ | (SEQ ID NO:56) where Z$_1$ is NOT K and/ or Z$_2$ is NOT T |
| (vii) | TIZ(D/N)PGCT | (SEQ ID NO:57) where Z is NOT N or L |
| (viii) | (D/N)YFXVLXZXX(K/R)H | (SEQ ID NO:58) where Z is NOT R | wherein X is any amino acid and Z, Z1, and Z2 are any amino acid other than those indicated.

Furthermore it is preferred, for EPSPS genes and proteins of the current invention, that the protein sequence comprise at least one of the sequence motifs i), ii) iii), v) and vi), preferably, at least two of these.

Furthermore, in amino acid sequence motif i) Z is preferably A, in sequence motif ii) Z is preferably I, in sequence motif iii) Z is preferably A, in sequence motif iv) Z is preferably K, T or A, in sequence v) $Z_1$ is preferably R or A and less preferably D or E whilst $Z_2$ is preferably V or A and less preferably T, in sequence motif vi) $Z_1$ is preferably E or A whilst $Z_2$ is preferably P, I or V, in sequence motif vii) Z is preferably R or K and in sequence motif viii) Z is preferably T or S and less preferably is Q.

Furthermore, some of the EPSPS protein sequences of the current invention are characterised in that they comprise at least one of the following sequences:

```
(I/V) VEGCGG(I/L/Q)FP(V/AIT)(S/G) (SEQ ID NO:59)
or (I/V) VVGCGG(I/L/Q)FP(V/A/T)E or    (SEQ ID NO:60)

(I/V) VVGCGG(I/L/Q)FP(V/A/T)(S/G)   (SEQ ID NO:61)
or (L/V) VVGCGGKFP(V/A/T)(S/G)or       (SEQ ID NO:62)

(I/V) VEGCGGKFP(V/A/T)E or          (SEQ ID NO:63)

(I/V) VEGCGG(I/L/Q)FP(V/A/T)E or    (SEQ ID NO:64)

(I/V) VEGCGGKFP(V/A/T)(S/G)         (SEQ ID NO:65)
```

Furthermore EPSPS sequences of the current invention are preferably derived from dicotyledenous plants.

Example 16

Stable Glyphosate-resistant EPSPSs Derived from Soyabean

Preferred examples of the current invention are the EPSPS protein sequences and the DNA sequences which encode these which are derived from soyabean (see for example EPSPS gene SEQ ID Nos 31 and 32) and which are then optionally modified according to Example 15 to yield a stable glyphosate resistant EPSP synthase.

Particularly preferred examples are EPSP synthase genes derived from soyabean in which:

(a) the coding sequence at a first position is mutated so that the residue at this position is Ile rather than Thr and a second position is mutated so that the residue at this position is Ser rather than Pro, the mutations being introduced into EPSPS sequences which comprise the following conserved region GNAGTAMRPL (SEQ ID NO: 66) in the wild type enzyme such that the modified sequence reads GNAGIAMRSL (SEQ ID NO: 67), And (b) the DNA coding sequence may be further modified in accord with Example 15 so that the encoded protein comprises at least one and preferably two or more of the amino acid sequence motifs ii), iii), v) and viii).

Example 17

Cloning of a Soybean Partial Length cDNA Encoding EPSPS

Soybean RNA is isolated using Trizol™ reagent as described by Gibco BRL and first-strand cDNA synthesised using Superscript II (Gibco BRL) using protocols provided by the manufacturer with the degenerate primer EPSPS 10 reverse (SEQ ID No.33). PCR is performed using ready to go PCR beads supplied by AmershamPharmacia™ according to the protocol supplied by the manufacturer using the reverse transcribed soybean first-strand cDNA product as a template and the primers EPSPS 4 forward (SEQ ID No.34) and EPSPS 10 reverse (SEQ ID No.33).

The following PCR conditions are used:
1. 94° C. 3 minutes for 1 cycle
2. 94° C. 45 seconds
   50° C. 30 seconds
   72° C. 1 minute for 25 cycles
3. 72° C. 10 minutes for 1 cycle.

The product obtained of approximately 1 kb is cloned into pCR2.1 using a TOPO TA cloning Kit (Invitrogen) according to the manufacturer's recommendations. Colonies are picked at random and are selected for further work via plasmid preparation with the QIAprep Mini-Prep Kit (Qiagen), followed by digestion with Eco RI to show the size of the insert in these clones. Clones containing the expected 1 kb insert are progressed. The polynucleotide sequence of selected clones is determined using an ABI 377 automated sequencer. Database searching is performed using the Blast algorithm (Altschul et al., 1990) and indicates that the majority of sequenced clones contain partial length cDNAs exhibiting high homology toward known plant EPSPS sequences.

Example 18

Isolation of a Genomic Polynucleotide Sequence Encoding Soybean EPSPS

A soybean genomic library constructed in Lambda Fix II is purchased from Stratagene and 1,000,000 clones are plated out according to the suppliers protocols. Hybond N+ filters are used to make lifts from the library plates and these were processed according to the protocols supplied by AmershamPharmacia and Molecular Cloning—a laboratory manual (Sambrook et al., 1989). UV cross linking of the DNA to the membrane is carried out using a UV Stratalinker (Stratagene). The soybean EPSPS cDNA probe is prepared by digesting the clone containing the soybean EPSPS partial length cDNA sequence with Eco RI and purifying the 1 kb product by agarose gel electrophoresis. The probe is labelled with $^{32}P$ dCTP using a Ready-To-Go™ DNA labelling kit (AmershamPharmacia). The filters are prehybridised and hybridised in Rapid-Hyb Buffer (Amersham Pharmacia). Washes are performed using 0.1×SSPE, 0.5% SDS at 65° C. The filters are then wrapped in Saran wrap and exposed to film in a cassette containing an intensifying screen as described in Molecular Cloning—a laboratory manual (Sambrook et al., 1989).

Figure 3:
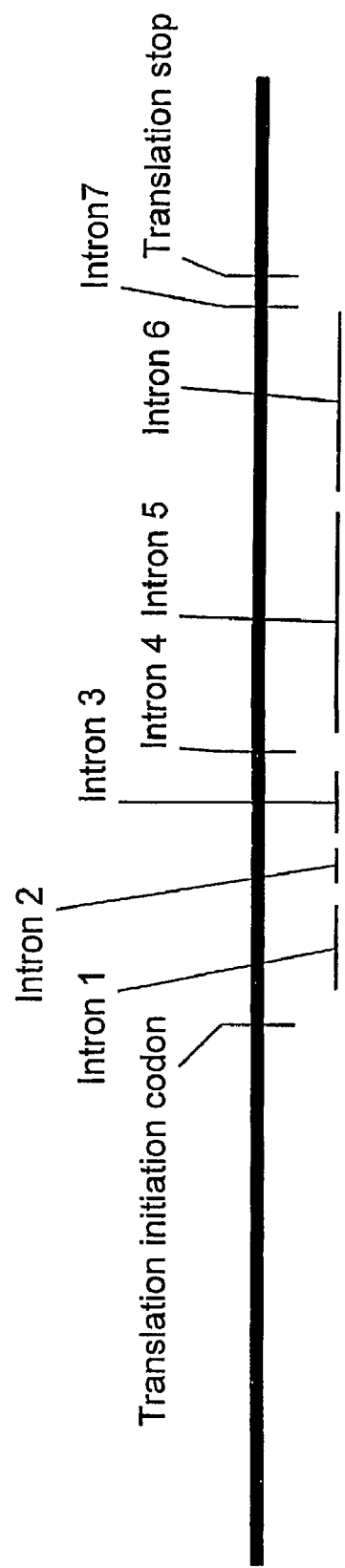
FIG. 3 shows a schematic representation of GmEPSPS 12.
Figure 4:
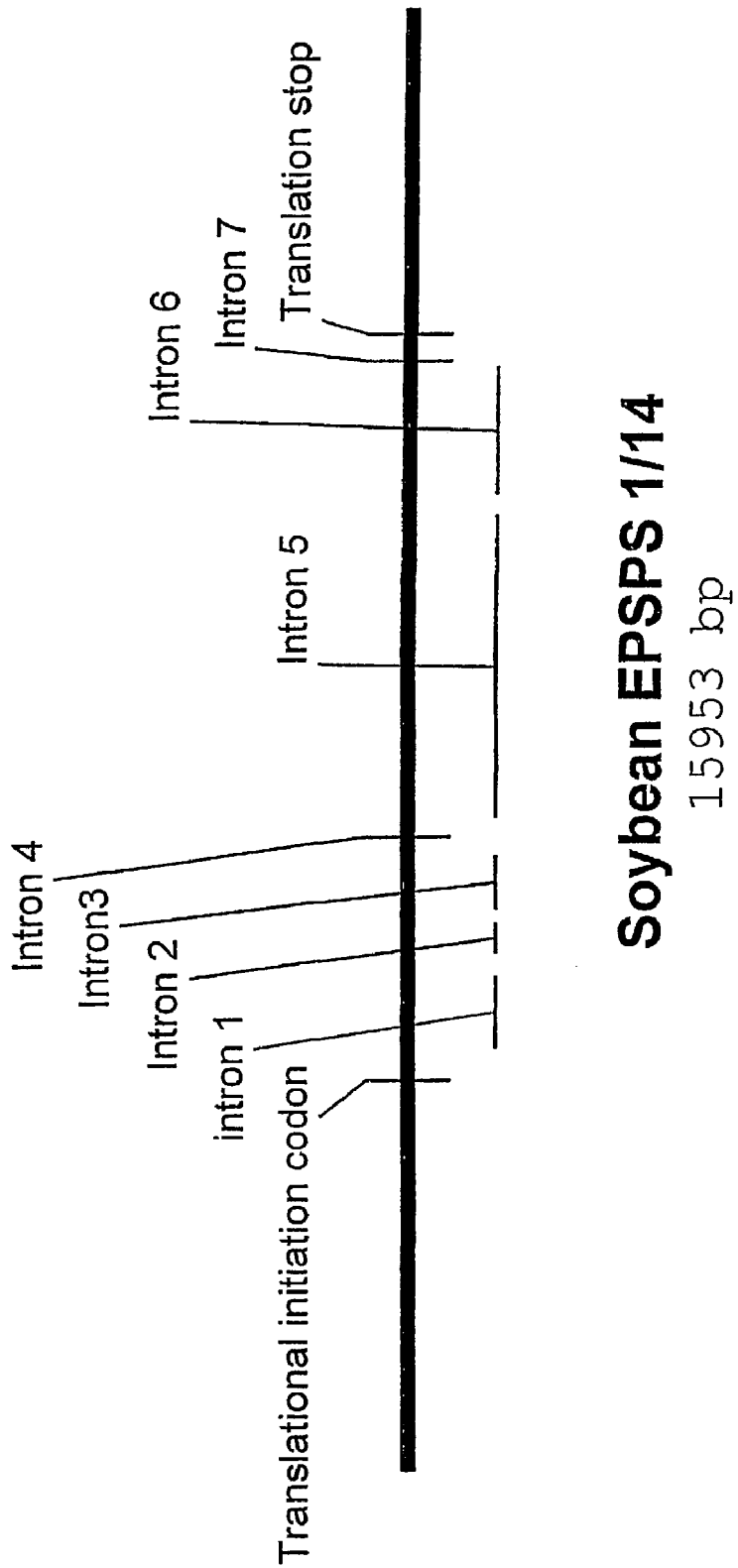
FIG. 4 shows a schematic representation of GmEPSPS 1/14.

Hybridising plaques are picked into SM buffer, replated at lower density and rescreened through 2 further rounds of purification. Phage DNA is recovered from plaque pure phage stocks using methods well known in the art (Sambrooke et al. 1989). The recovered phage DNA is digested with Not 1 and the genomic DNA subcloned into pBluescript. The resulting vector is transformed into TOP 10 E.coli. The resulting clones are sequenced using the Genome Priming System (NEB) using protocols provided by the manufacturer. Briefly, sufficient batches of 96 GPS events are selected and DNA prepared using a Qiagen™ Biorobot. The DNA was sequenced with the GPS-S and GPS-N primers as supplied by NEB using an ABI 377 automated sequencer. Sequence data are analysed using Seqman (DNASTAR Inc). The gene encoding EPSPS is identified by homology to known EPSPS genes using the Blast algorithm. The sequence of two contigs containing sequences showing high homology to known EPSPS are given in SEQ ID No.31 and SEQ ID No.32 and are termed GmEPSPS12 and GmEPSPS1/14 respectively. A schematic representation of these genes is given in FIG. 3 and FIG. 4.

The person skilled in the art will know that there could be other EPSPS genes present in soybean and that these may be isolated and the nucleotide sequence determined using similar methodologies as described in this example.

Example 19

Production of Plant Transformation Vector Harbouring the Soybean EPSPS Gene.

Figure 5:
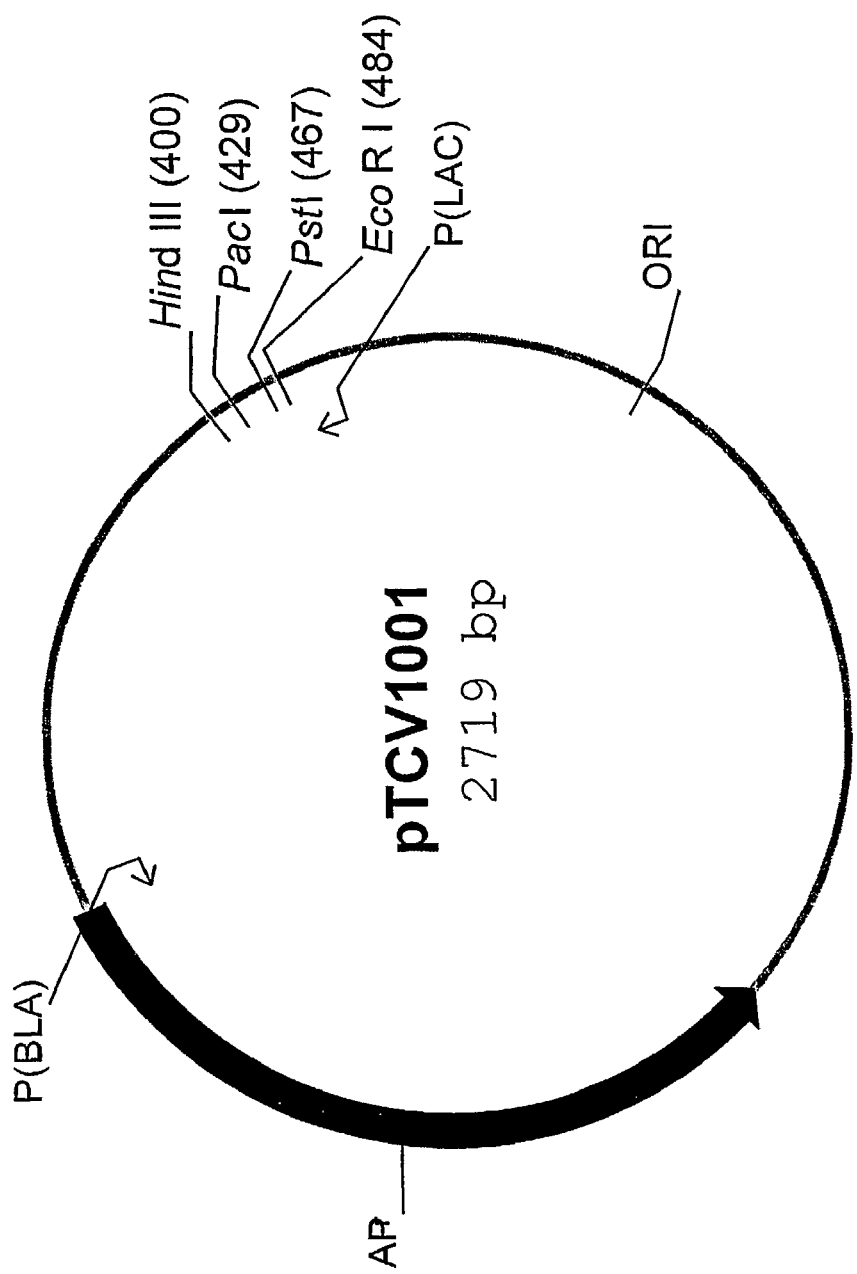
FIG. 5 shows a schematic representation of vector pTCV1001.

The two enhancer combinations FMV35S90 (SEQ ID No.37 and FMV35S46 (SEQ ID No.38) are synthesised chemically and subcloned into vector pTCV1001 (FIG. 5) using Hind III/Pac 1. The soybean EPSPS terminator, and a small region of the coding sequence, are obtained by PCR using the primers GmTermBam (SEQ ID No.39) and GmTermEco (SEQ ID No.40) using clone GmEPSPS 1/14 as template. The PCR product is cloned into pCR4-Blunt-TOPO, sequenced, and excised using Pst1 and EcoR1 and ligated into the pTCV1001 vector containing the FMV/CaMV35S enhancers. Finally, the Pac1:BamH1 DNA fragment containing the majority of the soybean EPSPS gene in either GmEPSPS 1/14 is excised and cloned into the pTCV1001 vector comprising both the enhancers and terminator.

Example 20

Introduction of Mutation into EPSPS Gene

The desired Thr to Ile and Pro to Ser mutations required to increase tolerance to glyphosate are inserted into the construct in the following manner. Primer BnMUT2PST (SEQ ID No.41), which contains the nucleotide changes that give rise to the desired amino-acid mutation, is used in conjunction with primer BnMUTKPN (SEQ ID No.42) in PCR with pfu-TURBO polymerase (Stratagene) with GmEPSPS 1/14 as template. The PCR product, now containing the desired mutation, is cloned into pCR4-Blunt-TOPO and sequenced. It is then excised as Kpn 1 Pst 1 and used to replace the corresponding fragment in the construct in pTCV1001 containing WT sequence. The final vector is termed pTCVGMEPSPS (FIG. 6).

Example 21

Introduction of 5' UTL

An additional 5' UTL, such as that from the small subunit of ribulose biphosphate carboxylase/oxygenase (Rubisco) or tobacco glucanase can be inserted into the construct by PCR. In addition the context surrounding the AUG translation initiation codon is optimised to give the consensus Kozak sequence ACC<u>AUG</u>G. With regard the SSU rubisco leader, primers GmRubPac (SEQ ID No.43) and GmRubbot (SEQ ID No.44) are used to introduce the soybean rubisco 5' UTL into 5' UTL of the soybean EPSPS gene. GmRubTop (SEQ ID No.45) and GmRubKpn (SEQ ID No.46) are then used to introduce the soybean rubisco 5' UTL into the first exon of the soybean EPSPS gene. The two PCR products are then joined, by PCR using primers GmubPac and GmRubKpn and the resulting product cloned into pCR4Blunt-TOPO and sequenced. Once the authenticity of the PCR product is confirmed it is excised from the PCR4 vector as Pac1:Kpn1 and used to replace the Pac1/Kpn1 restriction fragment in vector pTCVGMEPSPS.

These examples outline the construction of a DNA sequence comprising two enhancers fused to a soybean EPSPS gene containing specific mutations in the coding sequence that is capable of producing a glyphosate resistant EPSPS enzyme in plants. The person skilled in the art will know that enhancers may be introduced at various distances up stream from the promoter and transcriptional start site to act to enhance the rate and/or amount of transcription of the double mutant EPSPS soybean gene in plant cells. The distance may have to be determined empirically for each individual gene. This involves making a number of constructs where the enhancers are fused at different distances from the transcriptional start of the double mutant EPSPS soybean gene and introducing these constructs into plant material and assaying the material for resistance to selecting concentrations of glyphosate. The person skilled in the art will also know that enhancer choices are not restricted to CaMV 35S and FMV enhancers, but may also include enhancers from any gene that is highly expressed in plants including inter alia, enhancers from actin genes, ubiquitin genes, mannopine, nopaline and octopine synthase genes, genes from commelina yellow virus and other plant viruses expressed in plants such as potato virus Y and X coat proteins. The choice of 5' UTR may not be restricted to soybean small subunit rubisco and leader from other genes may be used.

Example 22

Plant Transformation and Regeneration

The expression cassette is excised from the pTCVGMEPSPS vector using Xma 1 and ligated into a binary vector pBin19 at the unique Xma 1 restriction site. The binary vector, containing the desired expression cassette transformed into *Agrobacterium tumefaciens* strain LBA 4404 using the freeze thaw method of transformation provided by Holsters et al., 1978. Tobacco transformation and whole plant regeneration are performed using *Nicotiana tabacum* var. Samusun according to protocols in Draper et al (Plant Genetic Transformation, Blackwell Sci. Pub. 1989). Transformation events are selected on MS-media containing kanamycin.

Alternatively PTCGMEPSPS, or other constructs capable of delivering glyphosate resistance in plants by the expression of a glyphosate resistant EPSPS gene from soybean may be introduced into plants directly without using *Agrobacterium* mediated techniques as described for Soybean in a number of references including the following: Physiol. Plant. (1990), 79(1), 210–12; U.S. Pat. No. 5,968,830; WO-0042207; and U.S. Pat. No. 5,959,179 and as described in Example 13.

Example 23

Analysis of Transgenic Plants

PCR Analysis of Transformants

Leaf samples were taken from transformed lines and DNA extracted according to known methods. Oligonucleotide primers are designed to specific regions within the transgene to enable its detection in the plant material tested.

RNA Analysis

The presence of mRNA encoding the transgene is detected within the plant using Northern Blot hybridisation. Total RNA is extracted from leaf tissue using Tri-reagent and protocols provided by the manufacturer (Sigma™). Blots are prepared using existing procedures and probed using radio-labelled soybean EPSPS cDNA.

Protein Analysis

The presence of recombinant protein in the transgenic plant is determined using Western blotting procedures with antibodies raised to recombinant soybean EPSPS using standard protocols.

Enzyme Assays

Resistant EPSPS activity is detected in plants using $^{14}C$ radiolabelled substrates and detection of products by HPLC.

Herbicide Tolerance Tests

Following tissue culture, transgenic plants are transferred to 5 inch pots containing John Innes potting compost no. 3. The plants are allowed to acclimatise (approx. 2 weeks) in the greenhouse and formulated glyphosate applied at various concentrations to the aerial tissue using a track spayer. Visual assessment of the transformed plants to identify those that are resistant to glyphosate is performed 21 days post application.

Example 24

Introduction of Plastid Targeted Pyruvate Orthophosphate Di-kinase (PPDK) or Phosphoenolpyruvate Synthase (PPS) Constructs.

Figure 6:
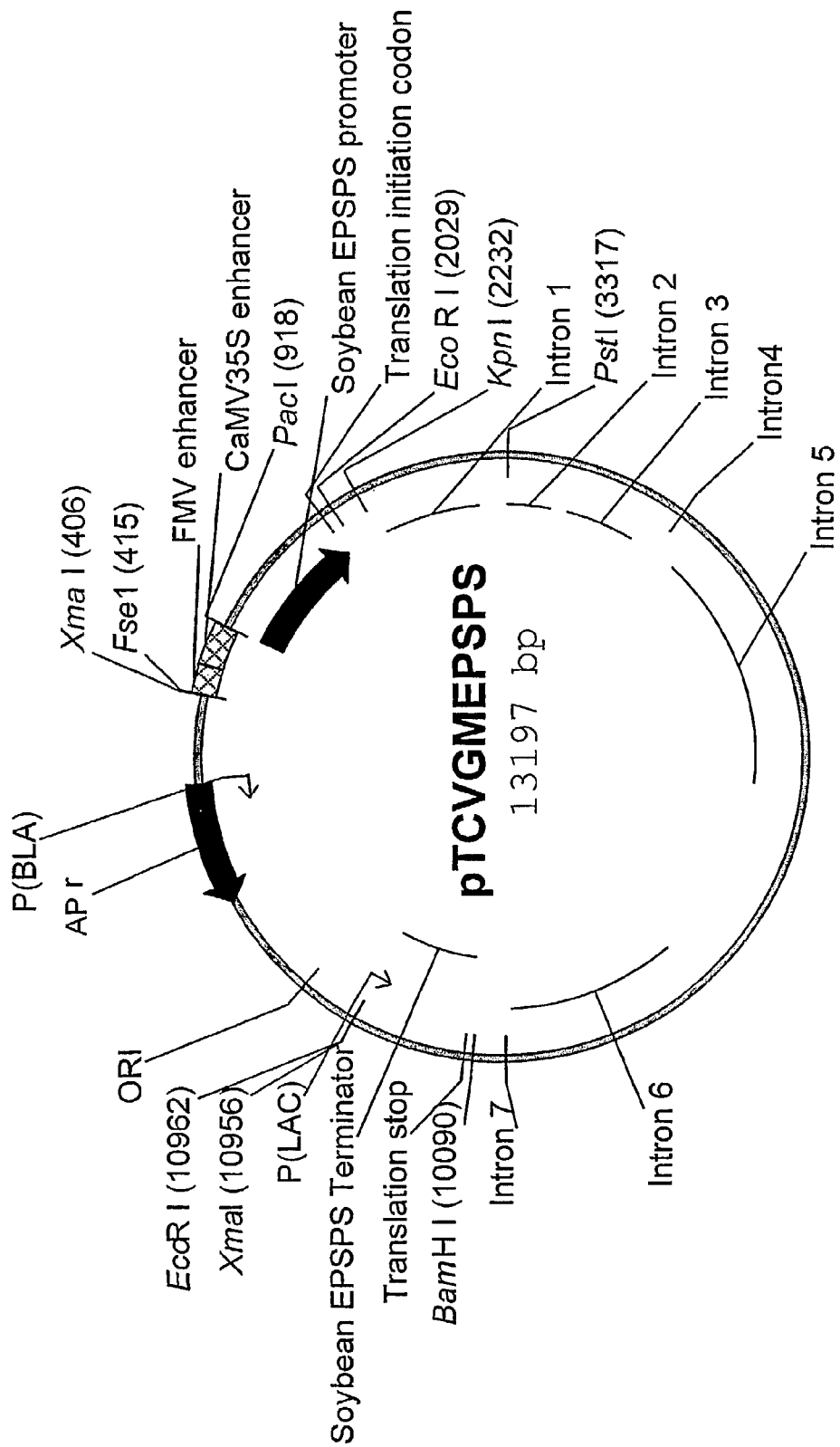
FIG. 6 shows a schematic representation of vector pTCVGMEPSPS.

The cDNA encoding PPDK from maize (EMBL Accession J03901), containing its autologous transit peptide sequence, is amplified by RT-PCR from maize tissue using primers ZMPPDK1 (SEQ ID No. 47) and ZMPPDK2 (SEQ ID no. 48). The RT-PCR product is cloned into the vector pCR2.1 TOPO and sequenced to check for authenticity. The maize PPDK gene is excised from the pCR2.1 vector, as a Nco 1/Kpn 1 fragment and ligated into similarly digested pMJB1 (FIG. 1). The plant expression cassetee is then subcloned into the pTCVGMEPSPS cassette (FIG. 6) prior to further plant transformation. Other PPDK genes, such as that encoding a cold-stable PPDK from *Flayeria brownii* (EMBL accession AAQ94645) or form rice can be engineered using a similar strategy. Likewise, the gene encoding PPS in *E. coli* (EMBL Accession X59381) is amplified by PCR using oligos ECPPS 1 (SEQ Id No. 49) and ECPPS2 (SEQ ID No. 50). The PCR product is cloned into plant expression cassette containing a plant operable promoter (such as the cauliflower mosaic virus 35S promoter), a chloroplast transit signal sequence (such as that from the small subunit of rubisco) and a terminator (such as NOS).

Sequence Listing

*Brassica napus* Genomic DNA Encoding an EPSPS (SEQ ID No.1)

```
Brassica napus genomic DNA encoding an EPSPS                                            (SEQ ID No.1)
gcatgcagatcttaaaggctcttttccagtctcacctaccaaaactataagaaaatccacttgctgtctgaaatagccgacggataaag tacttaagacgtggcacattattattgactactagaaaaaaaactcatacaccatcgtaggagttgggggtgaagaatttgatgggtg cctctccccccccactcaccaaactcatgttctgtaaagccgtcactacaacaacaaaggagacagacagttctatagaaaagctttc aaattcaatcaatggcgcaatctagcagaatctgccatggcgtgcagaacccatgtgttatcatctccaatctctccaaatccaaccaaa acaaatcacctttctccgtctccttgaagacgcatcagcctcgagcttcttcgtggggattgaagaagagtggaacgatgctaaacggtt ctgtaattcgccggttaaggtaacagcttctgtttccacgtccgagaaagcttcagagattgtgcttcaaccaatcagagaaatctcgg gtctcattaagctacccggatccaaatctctctccaatcggatcctccttcttgccgctctatctgaggtacatatacttgcttagtgttaggc ctttgctgtgagattttgggaactatagacaatttagtaagaatttatatataatttttttaaaaaaaatcagaagcctatatatatttaaattttc caaaattttggaggttataggcttatgttacaccattctagtctgcatctttcggtttgagactgaagaatttatttttaaaaaattattatag ggaactactgtagtggacaacttgttgaacagtgatgacatcaactacatgcttgatgcgltgaagaagctggggcttaacgtggaacg tgacagtgtaaacaaccgtgcggttgttgaaggatgcggtggaatattcccagcttccttagattccaagagtgatattgagttgtaccttt gggaatgcaggaacagccatgcgtccactcaccgctgcagttacagctgcaggtggcaacgcgaggtaaggttaacgagtttttttgtt attgtcaagaaattgatcttgtgtttgatgcttttagtttggtttgttttctagttatgtacttgatggggtgcctagaatgagggaaagacctat aggagatttggttgttggtcttaagcagcttggtgctgatgttgagtgtactcttggcactaactgtcctcctgttcgtgtcaatgctaatggt ggccttcccggtggaaaggtgatcttcacatttactctatgaattgtttgcagcagtctttgttcatcacagcctttgcttcacattatttcatct tttagtttgttgttatattacttgatggatctttaaaaaggaatttgggtctggtgtgaaagtgattagcaatctttctcgattccttgcagggcc gtgggcattactaagtgaaacattagcctattaaccccaaaattttttgaaaaaaatttagtatatggccccaaaatagttttaaaaaatta gaaaaactttaataaatcgtctacagtcccaaaaatcttagagccggccctgcttgtatggtttctcgattgatatattagactatgttttga attttcaggtgaagctttctggatcgatcagtagtcagtacttgactgccctcctcatggcagctcctttagctcttggagacgtggagatt gagatcattgataaactgatatctgttccatatttgaaatgacattgaagttgatggagcgttttggtgttagtgccgagcatagtgatag ctgggatcgtttctttgtcaagggcggtcagaaatacaagtaatgagttcttttaagttgagagttagattgaagaatgaatgactgattaa ccaaatggcaaaactgattcaggtcgcctggtaatgcttatgtagaaggtgatgcttctagtgctagctacttcttggctggtgctgccatt
```

-continued

```
actggtgaaactgttactgtcgaaggttgtggaacaactagcctccaggtagtttatccactctgaatcatcaaatattatactccctccgtt attaattagcaaaatcaaacaaaaattatattaaataatgtaaaattcgtaatttgtgtgcaaataccttaaaccttatgaaacggaaaccttaa tgaaacagagggagtactaattttataataaaatttgattagttcaaagttgtgtataacatgttttgtaagaatctaagctcattctcttttatt ttttgtgatgaatcccaaagggagatgtgaaattcgcagaggttcttgagaaaatgggatgtaaagtgtcatggacagagaacagtgtg actgtgactggaccatcaagagatgcttttggaatgaggcacttgcgtgctgttgatgtcaacatgaacaaaatgcctgatgtagccatg actctagccgttgttgctctctttgccgatggtccaaccaccatcagagatggtaaagcaaaaccctctctttgaatcagcgtgttttaaaa gattcatggttgcttaaactctatttggtcaatgtagtggctagctggagagttaaggagacagagaggatgattgccatttgcacagag cttagaaaggtaagtttcctttctctcatgctctctcattcgaagttaatcgttgcataacttttttgcggtttttttttttgcgttcagcttggagc tacagtggaagaaggttcagattattgtgtgataactccaccagcaaaggtgaaaccggcggagattgatacgtatgatgatcatagaa tggcgatggcgttctcgcttgcagcttgtgctgatgttccagtcaccatcaaggatcctggctgcaccaggaagactttccctgactactt ccaagtccttgaaagtatcacaaagcattaaaagacccttcctctgatccaaatgtgagaatctgttgctttctctttgttgccactgtaaca tttattagaagaacaaagtgtgtgtgttaagagtgtgtttgcttgtaatgaactgagtgagatgcaatcgttgaatcagttttgggccttaat aaagggtttaggaagctgcagcgagatgattgttttggtcgatcatctttgaaaatgtgtttgtttgagtaattttctagggttgagttgatt acactaagaaacacttttgattttctattacacctatagacacttcttacatgtgacacactttgttgttggcaagcaacagattgtggacaa ttttgcctttaatggaaaggacacagtgtggatgggtgatttgtggacgattcatgtgtggttaggtgatttgtggacggatgatgtgtag atgagtgatgagtaatgtgtgaatatgtgatgttaatgtgtttatagtagataagtggacaaactctctgttttgattccataaaactatacaa caatacgtggacatggactcatgttactaaaattataccgtaaaacgtggacacggactctgtatctccaatacaaacacttggcttcttca gctcaattgataaattatctgcagttaaacttcaatcaagatgagaaagagatgatattgtgaatatgarscggagagagaaatcgaaga agcgtttaccttttgtcggagagtaatgaattc
```

BnEPSPS5 (SEQ ID No.2)
gcatgcagatcttaaaggctcttttccagtc

BnFPSPS3 (SEQ ID No.3)
gaattcattactctccgacaaaaggtaaacgc

BnF1 (SEQ ID No.4)
gcgcaatctagcagaatctg

BnF2 (SEQ ID No.5)
tccttcttgccgctctatct

BnF3 (SEQ ID No.6)
gcgttgaagaagctggggct

BnF4 (SEQ ID No.7)
acctataggagatttggttg

BnF5 (SEQ ID No.8)
actaagtgaaacattagcct

BnF6 (SEQ ID No.9)
gttccatatgttgaaatgac

BnF7 (SEQ ID No.10)
tccactctgaatcatcaaat

BnF8 (SEQ ID No.11)
gtaagaatctaagctcattc

BnF9 (SEQ ID No.12)
tcatggttgcttaaactcta

BnF10 (SEQ ID No.13)
cagcttgtgctgatgttcca

BnF11 (SEQ ID No.14)
cgatcatctttgaaaatgtg

BnF12 (SEQ ID No.15)
ctctctgttttgattccata

-continued

BnXho (SEQ ID No.16)
cgcatcagcctcgagcttcttcgtg

BnMUTBot (SEQ ID No.17)
ggtgagtgaacgcatggctattcctgcat

BnMutTop (SEQ ID No.18)
atgcaggaatagccatgcgttcactcacc

BnNde (SEQ ID No.19)
catttcaacatatggaacagatatc

BnRB SEP (SEQ ID No.20)
cccgggatattggaagttaaaggaaaagagagaaagagaaatctttctgtctaagtgtaattaaccatggcgcaatctagcagaatctgc Brasr12 (SEQ ID No.21)
ggacgtggaaacagaagctg Bras r11 (SEQ ID No.22)
tctcaaaccgaaagatgcag Bnapus start rev (SEQ ID No.23)
ggttgaagcacaatctctgaagcttccatgg Genome walker 1 (SEQ ID No.24)
gatcttgggtcattttaatgggccttctaac with the AP1 primer
Genome walker 2 (SEQ ID No.25)
aaataaacccattaaccactaatgaaaaagggat with the AP2 primer
caMV343 (SEQ ID No.26)
gcggagctcgagactttcaacaaggg caMY46c (SEQ ID No.27)
atcccgggaagcatgcgaaggatagtgggattgtg BnGUSXma (SEQ ID No.28)
cgcccgggattgaatttbaaagc FMV enhancer (SEQ ID No.29)
tctagagcagctggcttgtggggaccagacaaaaaaggaatggtgcagaattgttaggcgcacctaccaaaagcatctttgcctttatt gcaaagataaagcagattcctctagtacaagtggggaacaaaataacgtggaaaagagctgtcctgacagcccactcactaatgcgta tgacgaacgcagtgacgaccacaaaagagctc caMV35S enhancer (SEQ ID No.30)
tgagacttttcaacaaagggtaatatccggaaacctcctcggattccattgcccagctatctgtcactttattgtgaagatagtggaaaag gaaggtggctcctacaaatgccatcattgcgataaaggaaaggccatcgttgaagatgcctctgccgacagtggtcccaaagatgga cccccacccacgaggagcatcgtggaaaaagaagacgttccaaccacgtcilcaaagcaagtggattgatgtgatatctccactgacg taagggatgacgcacaatcccactatccttcgcaagacccttc Soyabean genomic DNA encoding an EPSPS (SEQ ID No. 31)
aaaaaatacctttagtaaaataagagcgtragatcaatcagacgttttctctttgggacttctcattcttaattgaattgacaataactaaagt gaaactaaggctaaaatcaactcgcctagtcaagctcgtccacaaaaataggttttgaaagtttaccatgtcagtttcttactaagtaaaa aaggatcatttgtaaggtccaacgccttaaaatgatcacccttcaaagtaaaagaatcacttgtttcacgcataagtaagaactacgtagg tctgatttcctctccaaaggagggtacgtaggagcaaaagccccgcttttgtcgaccttaaaaaataaaaagaaacaaaagttaaggta acacaatttccacaattctagaaataaggttgttgtctttcgagacaaacgtaagaggtgctaataccttcctcaaacgtaaatacaactcc cgaacttagaattttcattttgaccggttttccttcggttttcccgacgttttccacaaataaacgttggtggcgactccgcgcatctttcctcct ttggaaagcgcacccatgagcctcgccctcgctcgcccgcgaagggcacgttgcgacactaggttaataagaagtttagtccacatat ctatggacctcttaaggtgattatcaaagtggaagtggtgacctacatgttggccctaccagcttattcgtatatuaccccccatcaaccat gtatctcagctgaaacatgctatcaatccaaatgttatcagaggaacatgagctgcatgttcaaccagaagtagttctagtcttaatacaa atgtcaaatggcacaagtgagattttgaatttctgatgttgtaaaaatctcaggacatgaatactattgggaagcaattattcatacttcacc aatccaaactgacccaaaattctcaaatcacatgaaagcaaaaatgcatataacacgaagaataagaagaagaggaactaaccctggg -continued

```
gtttcgatgattaaagcgttgttgttgatgatgaaaacgatgattatggagagaaattgttgttgaatggtgaaattgttatagaaagagaa
cgaagatagagaaaagatatatagatttttcaaggctcaaaccctaaaatcaccatgagagagaacaaagattgagaaacctacaac
cactatgagagagaatgagcagaacagaagcgtgagatagagaacgagagttaaggtgcgagaggacacgaagaacaaaaggtg
tgagagaaagaacaaaggagcctacggtgtgagatgagagaatttgaaattcttaccatttaggtggaatttcaattctacaattttattct
attaaaattatttttaaaaaatgatgtcattttaaattctttaaaatctcatatccaacaactgaattatgatagaggtatttcaaattcacttaaaa
aaattatcttatttaaataccccatccaaacatagcgaaatgttcatgagaaggatcaagtggtttggaaacatagtactaatggtgtttata
cagttcatggaatccttgatagataatttaaaggttgctggaaattggatgaaggtgtggagattaaatattcttccaaaaataaagcgtttt
atttggagagtgttgtgtggttgtctccctgtaggcaaaagcttcgatgtaaaggagttcaatgtccaataacctatgctttctatccctcg
attattgaaaatgaatgacacatttatttggttgaaatcaagaaataagcatgtggcaagcaacgggtatttgacaattcatagaacaaaa
ggtgaatgcagcaaaagaattaatgaactccttttcgatctacttggatcactacatggagatattatcaacaaatttgatgttactttatgg
agcagttggaattcttggaatgacaagatatgaaatgaacataccaaccctcctcttgtttctgtcggtttctatgcagtattttgttga[]tg
gcaaagtgcaaggtaatatgctcctcaacatcaattaacaaatgttcatgacatctcttaccagctccaacttggggacgtttgacaaaca
ccaccgtcaagtttccttaaatgcaacattaatgttgctcatttcaaggaggagaatagttttggtgtcggcatgatactccatcaaggaag
attcgtcaaagctcactcacgttttcgacatgggtcgacatgggltacctgacccaaaggctgaggcttaggcttgggtttgcttcaagta
ttgatctgggcccagactattggtttacataatatcattttttgaaaacctaacatctaaaactcaaggttgtttagaggtgcgccattccaaa
ataagattatcctatttgtgcatgaatgcgaccaactatctcctgtttcagcattataaagtataaacaacaaacttctttaatcaagggacta
aaagatattggacatacaagctaaaagtgatagaatttgagaaaacaaatattgacaacaatattcaagaggacactaaaacataattct
caaatttttttgtttatttaaaataaagtggttcattaggtagctcttgaaaaaaaaagtgattaacatgctagtacatgttaaaaaaagtga
ataatattctattataagtaaagaggaataatttatcgatgtctcattttgagatagttcaccgaagccaatttttttactttttttctcttcaatca
tgttactaaatataaatttcatggtatactcaggacggttataacggaaatcaaataaataataaaatagaataatatattaatttgcagtaaaa
tacagattttctctattaactaattaattaaaaattatccttattttaaggaaattaaaaattatcatatatatataagttttaaattaattatcttata
tatgtaccaaaaagttttaaagcaattattataaaaattaataaatttatcatataaaataatttataattaaattttaaattatcaattcattaaatt
aaattatttaaaattttttgaatgataatataataattttatcctctactaagtcccaacgtttcctattttattccadtttagcaataaattttgtcat
aaacacttataacaaaaaaagtaagtaaaaaataaaaaaaagttttttcaataaagtataaactaatttgtataaacttttagaaaaaataaag
aacaatgatttgcaattagatgataatataaaattattttacacactacatgtattaaactcaaacttttatatattagtttttctaaaaactaatttt
taactcaaaaaaatgttacttataattttcttatcttctttttttataagtatttttaagaaatttattgaaacatgaccatgcttgggtcaataat
actactctcttagacaccaaacaacccttcccaaactataatctaatccaaaagccatcattcattttccttggtaggtaaagttccaagacc
ttcaccaactttttcactcaattgttttggtgtaagcaattcgacatgtgttagtgttagttggcaaccaaaaatcccttttatgtgactcaatcc
aacaaccactcacaccaccaaccccataaccatttctcacaataccttcatttacacattatcatcaccaaaaataaataaaaaaaacc
taactcaaaaaaatgttacttataattttcttatcttctttttttataagtatttttaagaaatttattgaaacatgaccatgcttgggtcaataat
actactctcttagacaccaaacaacccttcccaaactataatctaatccaaaagccatcattcattttccttggtaggtaaagttccaagacc
caagtgagcagagtgcacaatcttgctcaaagcactcaattttttggccattcttccaactccaacaaactcaaatcggtgaattcggtttc
attgaggccacgcctttgggggcctcaaaatctcgcatcccgatgcataaaaatggaagctttatgggaaattttaatgtgggaagg
gaaattccggcgtgtttaaggtttctgcatcggtcgccgccgcagagaagccgtcaacgtcgccggagatcgtgttggaacccatcaa
agacttctcgggtaccatcacattgccagggtccaagtctctgtccaatcgaattttgcttcttgctgctctctctgaggtgaagtttatttatt
aagcatcatgtcccatgaaagaaatggacacgaattaagtggcttatgatgtgaaatgaggatagaaatgtgtagggttt1ttaatgg
gtagcaataagcatattcaatatctggattgatttggacgtttctgtataaaggagtatgctagcaatgtgttaatgtatggcttgctaaaata
ctcctaaaaatcaagtgggagtagtatacatatctacagcaaatgtattaggtgaggcatttggcttctctattgtaaggaacaaataatat
cagttaatgtgaaaatcaatggttgatattccaatacattcatgatgtgttatttatatgtacctaatattgactgttgttttttctccgcaatgacc
aagattatttatttttatcctctaaagtgactaattgagttgcttactttagagaagttggacccattaggtgagagcgtgggggggaactaate
```

-continued

```
ttgaatatacaatctgagtcttgattatccaagtatggttgtatgaacaatgttagctctagaagataaaccctcccccaaaacacatlatta
tctgtttttttttagggaacaactgttgtagacaacttgttgtatagtgaggatattcattacatgcttggtgcattaaggacccttggactgc
gtgtggaagatgacaaaacaaccaaacaagcaattgttgaaggctgtggggggattgtttcccactagtaaggaatctaaagatgaaatc
aatttattccttggaaatgctggtactgcaatgcgtcctttgacagcagctgtggttgctgcaggtggaaatgcaaggtctgttttttttttttt
gttcagcataatctttgaattgttcctcgtataactaatcacaacagagtacgtgttcttcttcctgttataatctaaaaatctcatccagattag
ctgagaaatgcacctgagggtgttcctcatgatctacttcaacctctgttattattagattttctatcatgattactggtttgagtctctaagtag
accatcttgatgttcaaaatatttcagctacgtacttgatggggtgccccgaatgagagagaggccaattggggatttggttgctggtctt
aagcaacttggtgcagatgttgattgctttcttggcacaaactgtccacctgttcgtgtaaatgggaagggaggacttcctggcggaaag
gtatggtttggattcatttagaataaggtggagtaactttcctggatcaaaattctaatttaagaagcctccctgttttcctctctttagaataa
gactaagggtaggtttaggagttgggttttggagagaaatggaagggagagcaattttttttcttcttctaataaatattcttttaatttgataca
aatatttgtcctccattccctttcccttcaaaacctcagttccaaatataccgtagttgaattatattttggaaggcctattggttggagactttt
cctttcagagattatccctcacctttattatagcctttctattttaaacttcatatagacgccattcttgttttaaaaaacactaagttttctttta
gttataccttcccctccttattctctccaaagtaaatattgtagcaagtgttggttgatccattgtgaatcttattatcctatttaacatgcaggt
gaaactgtctggatcagttagcagtcaatacttgactgctttgcttatggcagctcctttagctcttggtgatgtggaaattgagattgttgat
aaactgatttctgttccatatgttgaaatgactctgaagttgatggagcgttttggagtttctgtggaacacagtggtaattgggataggttc
tggtccatggaggtcaaaagtacaagtaggtttctatgttttagtgttacatcacttttagtatccaaaatgcaatgaatltttaaaactcatgtt
tcctattaggtctcctggcaatgcttttgttgaaggtgatgcttcaagtgccagttatttactagctggtgcagcaattactggtgggactat
cactgttaatggctgtggcacaagcagtttacaggtattcatgaatgacactatcttctattatcttttattttatagcttacactatcattcctaa
ttcaaccccttcttttctctttccctcactcccaaaatagagcttatcattgtatccttaatagctcttttatgtgctgtttcatctcttgagcag
atttcattaagagtgataaaattacattgtcaagtaaagcaagttagcgtatcagataatgatgcttcgattgcagaattggtgaaagcttg
cacaattcattagcttagtgacaattgtgatgtagatagccataatcttccatgcaacttattatgcttttttgtctaaaacttcttttgcacttaaa
catgaattagagagttaggatgaacaatagtaacagacacaaagcttatttctagaccacccagtggtgaagacgaagcagcatgagt
gagattaatggcagcatctgattgaagcttcttttggtattattggagatgaaatcttgagccaaattagggcttttgcctcctcaatagcca
ttggttcaaaattgctttcaataaaatgattacagaatcaaattcttaagaaagaccttcaagaacaacatcaagatgtttcctgtgcaaaac
aggctcacctacaaaagagtgtctacaagcacctttacacttgcaaaaaattccttaactgaacaattgccaagagtcatgttgcaaactt
gagattggagttgattagatttggtgtgtgtgagattctggaaatgagcatgaagttttttgcaaagctcataaaatgaatgcagccaaga
atcctagataggattgaatttgagagagaggcttgaagtcaagataaccgcaactgatcttgctgttcccatgctgcataggactcgttg
attctaccaagataacaatcttctgtggtgagaatatgagtgggaattgtcaggcaacaaagaaaatgaaggctatgagcctttgttaag
gtgcagagagaaaacagaaaatgaagaacttgtgtattgaaggaattgaaaagccaattacaattgtgttgcagagagatatttatagtt
ctgaagtgtataactaactaaacagaatgctaccaacctagaggcagttgagaattgctcccttattacaatactctcacagccttgatgat
aggcttgatttgctgccaccgaagaagaacattattgttggagttttttcagtgattgcatcagagaaagttacaagtgtgattggagat
gaaggacttgcggtcgtcgaaggttaagtgttaagtggtggaatgtgtatcggaggtggttgcctagcccaagaagctggttgcagtg
gaagcggatgcggcagaagccatgggttcagatcagaactatgttctagataccatattagggttagctttcaagagaaaacttatgaa
actgaactgtaaactgttgtattattgattagctgatctagtagtgatggaagcttgcttgcgaagcttctatggaggctggatcattgagct
tcaatgaggtccttcaatggtgattttttcaccatggagatgcagcggaagataaatgaagaggtgagaggaggcgtcatccactagga
aataaactatggaagaaggagcttcaccaccaagagagtgtcttggataagaagcttagagaggaagcttcaatggaggaatagaaa
gagagaggggaacaaaaaattgaaggaggaaaagagggagagaagttgaactttgaagtgtgtctcacaagactcattcattaaag
ttacaacaagtgttacacatgcttctatttatagtctaggtaacttccttgagaagctagaacttaactacacacacctctctaataactaaga
taacctccttgagaaatttccttgagaagcttccttaagaagattcctagagaagctaaagcttagttacacacacctctctaataactaagt
tcacctccttgagatgagaagctagagccttagctacacacaccccttataatagctaaactcactctattccaaaatacatgaaaatacaa
```

-continued aaaagttcctactacaaagattactcaaaatgtcctgaaatacaagactaaaactctatactactagaatggtcaaaatacaaggtccaaa agaaggaaaaacctattctaatatttacaaagagagtggacccaaccttagtccatgggctcagaaatctaccctgaggttcatgggaat cctagggtcttctttagtagctctagtccaattttcttggagtcttctatccaatatccttgggggtaggattgcatcatgtagtacaagagag gggaatatatatacagttgtaagttgtaactacctaatcaaacccaactgactcaccatacacagaaaaacaatgtacaaaggataaatag aaaaactgaaactgagatatactcattacatagaagaattacatgatgaatctgaaaattttaattgggaaactgaggac[]taacaagg ctttcagagttcattttgacaataggtaaattatggacttcaacttagacctcaagggtatgcttgggagtgggg ttttagaggaaaaggg gaaggagggaaattttttaattctagtaaatattctctattttgattaatttttaaaataaaacaaataaacttatagattagcattcacttaatgt cctgatcttttatttgtttcatgaagttttttatagcctttctgtttctgttaaagaaattggagggtgttcataatctatatgcccatatatatgta ttttttttacctgtactataactttccaaacaaatagtagaaaatgtttcaaatattccccagaactgtttcagtgaacaaagttcaagccagaa aaaaagcaagcagaggctaaagaagtatatcttattgtgaagagtaatctcaattggttaattatcgaattgtatcattttacaatagaaaat tagaagtgggttgattagtttatacgaacaattatttaaatagggttgatggtgtggttaattactgatcatatgttaagactatgagtcgatg accagcctcagtgcagtcattttaagttccattatttttttaattgtgcttatgtttaactttgtccttcttttaaagggagatgtaaaatttgctgaa gttcttgaaaagatgggagctaaggttacatggtcagagaacagtgtcactgtttctggaccaccacgagattttctggtcgaatl.agtct tgcgaggcattgatgtcaatatgaacaagatgccagatgttgccatgacacttgctgttgttgcactatttgctaatggtcccactgctata agagatggtatggtttagctgtttgttttgctcaagagcttgttttcacatatttgtggtcaagagcggtttagctgttttttttttttaaattgtgg ttaatgaaattattataattatactaatattgaaattggatcactaaccatgtgaaatgcttgaattttagcttgaaaacttettttgtggatgatt tttcttttatctatgtagtgtggggcatctatgttgttcctttaagctttgtgtcatagttgtacaacctggtctgtgggctggtccagtt cit act catgactgtcttttgcagcaaactggttaaacttgggtgacctgttgacccacccagattggcctgttctttttttaaataaaactccaaaagg ctacttataagatttcaacatgatacttgaatgaccaccccttacttt aaaggtcattatgccatcagaccccttgattctctgttcagttatgttc ttattcttattattttttaatttatattattatccaacgatctgatctttgtacatgatgctggacaatcatcaaagctagtttggttacatcatataa aatactatttcaatgactgggccttattattttctggtttgggttatacaactgtcctttgatgtacttttgaatgcttcaatagtattttttcataatc atggaaggcactagagtgcagtgcatattgcacaaggttctttaatggcatcttgaatttgttagaacatggagttatgatatacaaccatt cctatgtcttcatctaatagctaaagcttttggcgtagttggttaacatggtattggaatcttatttttaaaggtccatcttattcgcaagtacaa ggcaggtggacctgcgcattattcacgtgccaggctcaaagggattttgtatgagggggaattttttggaatataatatatagaatcattca tgtggttcacctatcatgtgtcaactcaagttttttgtcctagttgtattattgcagtgtctaaactaggcatgatcttctgtggaaggaaattta acctaaggaacttgaatgcttcttgttctgagatctttattttttttctccaatcttttttaatacttgaaaggttttagttgtatctataaagggtgc agaattaggggg tcagcttttctgttgtaagcgtgaattaagtgcattttatgttgttccctattttatacatttgaactatcaa.ccatatcattta gcaaacttcttttgttgctcagattcccatttattcttgtttcctctattttttagtggcaagttggagagttaaagagactgagaggatgatagc aatctgcacagaactcagaaaggtcttgctaattcctttatggtttctatattactggacttttacatctcactgacctactactgtcttggtat ttcagctaggagcaacagttgaagaaggtcctgattactgtgtgattactccacctgagaaattgaatgtcacagctatagacacatatga tgaccacagaatggccatggcattctctcttgctgcttgtggggatgttccagtaaccatcaaggatcctggttgcaccaggaagacatt tcctgactactttgaagtccttgagaggttaacaaagcactaagcattttgtacattgagtagggaagagagagagatatatataaatact cacaaagcagtgagtatatggcttgcttttgtttctaaacattccttt ataaggacttgagataatttgtattgtttaaaagagccattggttct gttgtatcaaagtaatttaattttcagtaccgacttggctctactcatatgtggtggtgtacattgcatcttttgcatttgattccatatctattgg gatgggaccatacattttttgtttattatttaagtcaaacatatcagataatatgtggtgaccagaaaagtgtctagcaatcaaatgggtctgt gattgcatgtttgagttcaggacatttattaatgagtgacagaattttaaaaagctcgccaataggagttgccacatctgatcgagtcttctg taaacactaactgtaacttgagtttgataatcagattccccgttggtaggtaatatgtaaatttcactatagattcttactgaggatgatgg tcttgacttcgaagtggtgagtgtaattctctaatctaaactttatatatatataaaaaaagaatgttaaaaaacttgagtgacatacagcaaat agcaatgaaagcatgaccatggccttgggggccaaatggccatgtaccacttttccacctacttgagagccatggtcctgaatgaggt ccttttgtttcattttttttacaataaagaaagttcatattcttggcaatagcaaggcaaatcatttgtggaagtcacatgaaattcaccatagg -continued

```
cttcattgttcaaatcctttagtcactaaggcagggcctatgtaagaattttgactactcttgtaaatgctgtgcggtaaagactacgggaa
aatataaattattgcatatotagaggtgaggttcatctccgatccatttctccaagtaataaaaatatatataaattattaatatggtatgata
tggttatttgtcctttaaatatgcgattataggttcaatctttggttaatctatcaaatgcatctcaatattttgagagaatagttttttagctcttga
ctgagagatacttgagttaaaaaatgtatttataaactattgtctattgaatttttttattttttttgtaacaccacatgtgagtattttactaaatcc
atgttacaatgtactgaatgttttacaatacagtctggtttgataataaaatatgcacaaagtccagcttatgtaactctttcaattcatggaaa
atgatgatatgcgaattgaaagaaagaaaaccataatgtaagtgtatttttttttttctttctcttctttaatattactcaatatcagattgcacatg
ggaagggtactggctcatgtgggatattaattttatcccttacctaaaaagagagaaagagaaaataactatttaaaaagagtaccacc
accacctttttcgcttttaagttttgttctgttttcactactctttcatgcgttgtttgttggcttccgatagtgacgaatatgataatgattttacgt
tgagaaaaaaatgtgccatgtaaattccagagattgaaattttagcttcaaattaatatttattttattatcttttcaaattggttgcatgtgaa
agaatttgaagttcttcaacaaggaaataaacacttcaatgctcaatccttagagtcagtcactagatcccaaaagaatgtgatgtttacac
acattagtatatatatatataaacacagcttatattatattaatgagtgatgcgcgaggacggtggtgacactacatggccaaaacaag
aaatgtaatttaatttttttttctttaagtattactctatccttgaatattagtcttaaatcttcaaagaccttgcgaacgaagcaatcttgtcctga
tcctgtgattgttctacactagtccttacgtgtacctaagcacatgatactttgctgccctaacataaattgtaccataaggattcttgggga
gatgcttttgccttcatttcaagtttgtttacactttcaagtcgttttttcaatgcattctctttcctttctgggaccccttgtctttaacacgcgc
gcacacaaaaactagtagacaataattagtactacttgggttccattaaattgtaactacatatacatgtgtttttttttttcttggatcaactgc
atatacatgttttatgagtttcattgaatttatatttacacaaacagttattaaaacataatgtagagccttgtcattaacctgatgttaggatt
ccgttcaaaagagagacgacaaggataatactaatactagtagattccacgcattcaaccctagttagtttagctatgacaaattaagcat
ggtaagaaaaggggaggagaaaagtaagaatgaaaacatataacaaattgtgattgaacttttccatgacgtaatgaaaacattaattttt
aagataagcttcaactcctaagaagagatatgtcaaagaaacttaggattttttctctatttataacggtaaattactcatccttttaaatgatt
aatttgcgttgttgaattcgttgtaaagggaaaatcaagaagtctcttcacgggaaagttatatcaaagtatcatatactagacttcatggct
agcttttactttgattataagtaatgcatgcaattaatgggcaaataaattatttgaaaccaactaaagtacaaataattttcctccaaaacct
ctcaagttcgcattgaaattaaataaaccaatgcatattaaggcgtaaatctaaaccatgtttgtttcatcttgtattgtatatcatagtattaat
aaggtactttgaatttagttgttattgaccgttaaatttaggggtgagttgttttactatctcttactcaattgcttttattcaacgcaaattctagt
aggattttcagcccaaattaaaagaagttttacggtttgattctctacaaacttgaattgagatttctaatttcagaaatcaataattgcggtct
taattaactctataatcaaacctttttaacccaatcttttttctcaattctctgaattaagacaatcaaaatttaaactcacacgaatctcacacgc
cttcccacggtagagaaatataggagtccccttaatagcaaaagcctcaaaattcagaaaatctcatccattgcatttgcacattcaacaa
accacccattattatgttcccttaataaatctcacacttaaaaaccctcctcacccataattaacccaaaaggaagtttcctccacacaaaa
aatatccttaaacaaagagcctctataaatctattttaaaaaaaccccccaaatttaagga
```

Soyabean geriomic DNA encoding an EPSPS (SEQ ID No. 32)
```
aaaagtctgaatgaagtgaagttgttgtgttaggggatgctgaatttgattttaatttaatttaaataaattacctgtgtaaaggattttttgta
ccgccttttaatcacaaattgtcgtgtatcgaaagtttgttgaatttttatagtaactatcttggaggttatacctagtaggatttctgattagtta
accatgtaaatttttttaatgggtttgtgtttgttttaactgatgttgttttttgatatgtacgtggtaagtgtgatgagtttgtgcatatcttgatca
aagactgaagtgaagttgttgtgtttgggggggttgactcttttaggaagaggatttgagggaatttcgccaatggggagcagaactcc
gggacaccctgagaattttgagactccgggaattgaagttacaacaggtttgatatgagttagagtttgtataatagaatagtaattcttttt
attttttatttttattgtttatttatccattattgctatttttgtaggtcctcttggtcaggggattgccaatgctgttggtttggccttgcagagaa
gcacttggctgcaagatacaacaagcctgacaatgagattgttgaccattacacgtaaaaaataactaaatcatacacaacttgcaagact
ttagttgttggtgttttgctaatggcgttttgttttatgcaggtatgctattctgggtgatggttgtcaaatggagggaattgcaatgaagcat
gctcacttgctggccactgggactggggaagctgatagcattttatgatgacaatcatatttctattgatggtaacacagagattgcgtt
caccgagagtgttgatagtcgttttgagggacttgggtggcatgttatttgggtaaagaatggaaataatggctatgatgatattcgtgct
gccattaaggaagcaaaagctgtcaaagacaaacccacattaatcaaggttagtttactaattgtggcaatgatatgcatagatttctggc
```

-continued

```
ttgtagttaccataacaatcataatctgtcatgatttataggattctttttaaactaaggttataaacatgatatgttactaaagactgcattgc
attgtagtacctcatttgagaaactggaagttataggtgggaaatcaaaatagtaaattatgggtcagtttattaagtgtagctggtttgtctt
ttgctaactctatcatttcacaggtcacaacaaccattggttatggttctcctaacaaggetaactcctacagtgtgcatggaagtgcactg
ggtgccaaagaagttgatgccaccaggcagaaccttggatggtcacatgagccattccacgtgcctgaggatgtcaaaaagtatggat
gatgggtttagagatttctttttttcctgtgacactgctgatgtttataatgatactgaataagaattgcttgtctgtccccaggcattggagtc
gccacacccctgagggtgctgcacttgaagctgagtggaatgctaagtttgctgagtatgaaaagaaatacaaggaggaagctgcag
aattgaaatctattatcaatggtgaattccctgctggttgggagaaagcacttccggtgagtaaattctaaactcacaggttttttcttacatgt
ttgtaacttttcaaggtttggattacatactatccaaagttgatcatgatttcagtttgatttggtagtatgggcttcaaaaagttattccaaat
attaaaacctggcttccaatttgatttcagacatacactccagagagcccagcggatgccaccagaaacctgtctcaaacaaaccttaat
gcccttgcaaaggttcttcccggtctgcttggtggcagtgcagatcttgcttcttccaacatgaccttgctcaaaatgttcggggacttcca
aaggatactccagcagagcgtaatgttagattcggtgttagagaacacggaatgggagctatctgcaacggcattgctcttcacagcc
ctggactgattccatattgtgcaaccttctttgtattcactgactacatgagaggtgccataaggctttctgcgctgtctgaggctggggtta
tttatgtcatgacccatgattcaataggacttggagaagatgggccaacccaccagcctattgagcacctagcaagcttccgggcaatg
ccaaacattttgatgcttcgtcctgccgacggtaacSgaaacagccSgagcatacaaagtggccgtgctcaacaggaaagagaccct
ccattcttgccctatccaggcaaaaactgccccagcttcccggaactthcattgaaggagttgaaaagggtggttacaccatttcggga
caactccactggcaacaagcctgatgtcattttgatcggaactggttcggaattggaaatcgctgccaaagctgctgatgacctaagga
aggaagggaaggctgttagagttgtttcccttgtttcttggggaactttttgatgagcaatcagaagcStacaaggagagtgtt[]ccctg
ctgctgtttcagccagagttagcattgaggcaggatcaacatttgggtgggagaaaattgttggagcaaagggaaaagcaataggcat
tgatcgttttggagctagtgotccagctggaagaatatacaaagaatttggtatcactaaggaagctgttgttgctgcagctaaagagctt
atctagaacttttgattttttttgccttciggttttggttgagagcattccatgtcatgaataagaaaaaggttaaatatccttcgattgggaat
ttgggattctaagtgaagaagcaacatagatcaaagaattttgtgaacttgtaataactatttgacaatttagttttgcactgccacatggtta
aattcaatgtttgatcatateaaccatagatgctagtttatactacttgtataatttgtttcacttgcagattcactcttagcatttgagtgtttgg
atggccgtgttttgttcattaagaaatgttgacatggatagtttgttgcatggtaaattggtgattaatacctttttaagcttcttttggcaagtt
gttaaaaagtgttttgttttaatctctagttaatctaaaaatgcctacttattttattttgactttcaaaacttgtctatatgccgagtataaaaaa
actctatataagttccttatggaaaaaggacctacaaataatttaaaaatgctgaatttgttaggaagtttgacaactttagacattaat
aattgtttttttttcatatatataattgactttcaaaacttgtctatatattataaattcgttatggaaagggcgaccacacgtaaaacgtaacat
gccaatctctccctagtgaactgttattctcattcagttttttgtaagttcaccttcaaattttcaatttttttttgacaaaaatatctttgatggaac
acgttaggggtgtaaattcaccattcatcatttcattcattatacacaatagtctttcataatccaatgaaaacttgttttttgttgttatttttttctg
aaaaatcttttataaaataaataaaaacatttttttgttataaatttcagttgaaatacataaccattaattctacagagtgttaatgttgatgtaaa
ataaaaaaatattggatatcaaacttaatgaacagaacaaaaattacaaaattgtacaatttaaatgataaaaaaccaaattcacaaaaata
aaaattaaggacgaaatttgagaaatgataattaaaaacgattaaaaatataattaaactaaaatttattatgtaattctttaatatatatatata
tatatatatatatatatatatatatataataaaagttttacattataattttgaaatgaagtatttgataaacgaacaacccaccccttggg
gttggtgagagtgaaacggagaacagtgtctccctcacttggtcttctgagtcgagtcctattcatcaccaacccactcgtcaaaattgtt
gtatgctatgtaaccatttttgttttttaataaataaaagtgttttgttctgctatgcactccccatcaaataccatttacttttttttttgtcttctatca
attctatttagttcctagttgctacaacttccagctggtgaaaatagtcaacagagactacaatattctaataaaatagaataacaaatc
aaaaatttctacaattatagaaaagtttagttttgtagattgttaacataaagattttcctattaactaattaattaaagtcatcttatatataa
gttttaaagtaattatcttatatatgtacccaaaagttttaaagcaattattataaaaaagtaaaatttttatcatatacaataatctataattacat
attttattccacttttttaccaataaatttcctcataaacacttataagaaaaaaagtaagtaaagaataaaataagctttttctataaactataaac
ttttttaagaaatttgttcaaacatatttttatgacatgtcaatgcttgagagatataaggtgagttaaatcataaatgattaaagaaaaataaa
agaagaaaaagataattaatttaattttttattaacattctaacaaattaacattatataaataaaaataatatttcaataattggatcaataatac
```

```
tattgttcttaaacaccaaaccaaccttcctaaagtcctaatctaatccaaaagccatcattcattttccttggtaggtaaagttccaaaacct
ttaccaaccttttcactcaattattttggtgtaagcaattcgacatgtgttagtgttagttggcaaccaaaaaccccctttatgtgactcactcaa
tccaacaacctctcacaccaccaaccccccatactcataaggccaaaaccatttctcacaaaaccottcattacacacattattatcatt
atcacacacacaaaaaacctctcatttcaaagagagagagagatttcacagaccaaattgcagaggacgacaaagttcacaacttcaa
ggaaaatcgaaatggcccaagtgagcagagtgcacaatcttgctcaaagcactcaaattttyggycattcttccaayyccaacaaacy
caaatcggygaattcggtttcattgaggccacgcctttggggksoctcaaaatctcgcatcyygrtgrnayaaaamtggaagcyttat
gggaaattttaatgyggggaagggaaattccggcrtgtttaaggtttctgcatcsgtcgccgccgccgcagagaagccgtcaacgtcg
ccggagatcgtgttggaacccatcatlagacttctcgggtaccatcacattgccagggtcgaagtctctgtccaatcgaattttgcttcttg
ctgctctctctgaggtaaagtttatttatttatttatttctgtatccaaaaatgtaaattgttagtttgttaattttgttagcagtgagagtcgaact
acttggcttcttcttagtcatccaaccaaccttatatctccaaaatttatttattggtttttttgggtatgtggtaggaataggagtttgatg
cgtggagtggattttgaatatttgatttttttttttttgtattattcagtgaaaatgaagcatcttgtcccatgaaagaaatggacacgaatta
agtggcgtatgatttagaatgatgatagaaatgtgtataggtggttttaatgtgtagcaataagcatattcaatatctggattgatttggacg
tttctgtataaaggagtatgctagcaatgtgttaataatgtcttgttaaaagtatggatggctaaaataatcataaaaatcgagtgggagta
gtatacatatctacaggaaatgtattaggtgaggcatttggcttctctattgcgagtaaggaacaagtaatctcagttaatgtgaaaatcaa
tggttgatattccaatacattcatgatgtgttatttacgggaacgcaatattgactgttgattttatctgcagctgagattatatactatatcctt
ccaaagaaatctttgactcttgattatccaagtatggttgtattaccaattttagctctaga.agataatccctccccaaaacacaaattaga
ttttattcttatttagggaacaactgttgtagacaacttgytgtagagggaggatattcattacatgcttggtgcattaaggacccttggact
gcgtgtggaagaygacmaaacaaccaaacaagcaattgtkgaaggctgtggggggattgtttcccactaktaargaatctaaagatga
aatcaatttattccttggaaatgctggtactgcratgcgtcccttgacagcagctgtrgttgctgcaggtggaaatgcaaggtctgtttttttgt
tttgtttgttcatcatgatctctgaattgttcctcgtataactaatcacatcagactatgtgttcttcctccatcctgttataatctaaaaatctcat
ccagattagtcatccttctttaaatgaacctttaattatatctatgtatttatttaacatgtaaattagcttgtcaagtcaaagtctagcatataga
tatactgattacactctgaggaatgcacctgagggtcttaatcatgatctatttcaaccttgccactttcttcttttattattagatcacctatcat
gattactggtttgagtctctaaatagaccatcttgatgttcaaaatatttcagctacgtacttgatggrgtgccccgaatgagagagaggcc
aattggggatttggttgctggtcttaagcatctyggtgcagatgttgattgctttcttggcacaaactgtccacctgttcgtgtaaatggga
agggaggacttcctggcggaaaggtatggtttggatttccattagaataaggtggactaactttcctggagcaaaattctaatttataccct
gtttcccoctctttagaataagacactaagggtatgtttaggagttgggttttggcgagaaagggaagggagggcaattttttttctaataa
cctctatttaaaaacaagatattttteetccattcccttteoctttaaaacctcagttccaaatataccgtacttgaattatattttggaagtgta
ttggttggagacctttccttttcagaggttatccctcacctttattatagcctttctactctcttaatgagttcattgtgcattgagtcattgaactt
cctgtgaaaagaaattgtttacttttcttatttgttacctacatccttattcctgttttaaaaaatactaagttttcttttagttatgccttcccctcc
ttattctctccaaagaaaatataatagcagaatgttggtttatccattgtgaatcttattatcctatttcacatgcaggtgaaactgtctggatca
gttagcagtcaatactgactgctttgcttatggcagctccttagctcttggygatgtgaaattgagattgttgataaactgatttctgttc
catatgttgaaatgactctgaagttgatggagcgttttggagtttctgtggaacacagtggtaattgggatargttcttggtccatggaggt
caaaagtacaagtaggtttctatgttttagcattacatcacttttttagtatccaaaatgcaatgaaatcaaaactcatgttttctatcaggtctc
ctggcaatgcttttgttgaaggtgatgcttcaagtgccagttagttmctagctggtgcagcarttactggtgggactatcactgttaatgg
ctgtggcacaagcagtttacaggtattcatgcttgacactatttctattatcttttattttatggtctatactgtatcattcctaattoaaccccct
tcttttctcttccoctcacttccaaaaaaatagagcttatcattgtattcttaatagctcttgtatgtccttttcgtctcttgagcagattctacc
tatttcattaacagtgataaagataaaaataaattgtcaagtaaagcaagttagcatgtcagataatgatgcttcaattgcaaaattggtgaa
agcttgcacagtacattagctttggtgacaattgtgatgtagatagccataacctcccatgcaacttattatgttgtttgcttaaacttcttttg
cacttaaacacggattagagagagtgaggatgaacaataataacagacacaaagcttagttttataccaccccggcacccagtggtgaa
gaccaagcagtatgagtgagatcaatggcagcatctgattgaagcttcttgtggtattttggagatgaaatccgaggcgaattagggca
```

```
tctggctcaacaatagccattggttcaaacttgcttttaataaaattgattacagaatcaaattcttgaggaagccttcaagaactacatcat
gatgttccctgtgcaaaacaggttcaccgacaaaagagaacatctacaagttccttt acacatgccaaaaattcctcaactgaacaattg
ccaagagtcatgttgcgaacttcaggttggagttgacgaaatttggtgcatgtatgattctggaaatgagcatgaagttttttcctaagctc
ataaaagtgaatgcagccaagaaccctagataggattgaatcggagagaggcttgaagccaagataacagcaactgatcttgctgttc
ccatgctgcgtaggactcattgattctaccaagatcacaatcttctgtggtgagaaaatgagggtgaattgtcaaccaataaagaaatg
gtgaaggctgagtcttgatgataggcttgatttgcttgcgctgaagaagaacgttattgttgtagagtttctcagtgattgtatgagagtaa
gttacaggtgcgattggagatgacggacttgtggtgggaggagggtaagtgttaagtggtggaatgcgtatcagaggtggttgccca
gccaaagaagctggttgcggtggaggaggtggtggtgcagtggaagccatgggttttgatgcttttgagagaaaacatacgaaactg
aactgtaaacttttgtattattgattagctgatttggtagtacaagagaggaatatatatacagttttaatgtaactacctaaccaaacatgag
gaactctccatacacagaaagacgtatacaaaggataacagacaaacagaaacttagatatactcatacagagaagaattacaggatg
aatctgagaattttaattgggaaactgaggaaaatagcaagggtttcagaattcattttgacgataggcaaatcatggacttaacttagac
ctcaagggtacgcttgggagtgggggtttttagagggaaaagggaaggagggcaaacttttaattcctaataaatattctctttttttgatttt
ctatagtatgtataactattcaaataaatagtagaaaatgtttcaaatattccccagaactgtttcagtgaacaaagttcaagccagaaaaa
agaagtatatcttcttgtgaagagtagtctcaagtggttaattgtcaaattgtatcattttagaatacaaaattagaagtggtttgattagtttat
acgaacgattatttaaatagggttgatgatgtggttaattactgatcatatgtgaagactgtgagtcgatgaccagcccagtgcagtcattt
taaattccattattttttaatttgtgcttatgttaaactttgtccttctttcaaagggagatgtaaaatttgctgaagttcttgaaaagatgggagc
taaggttacatggtcagagaacagtgtcacygttwctggaccrccacragattyttctggtcraaaagtcttgcraggcattgatgtcaat
atgaacaagatgccagatgttgccatgacwcttgcygttgtgcactatttgctaatggtcmmactrcyatmagagatggtatgttt
agctgtttgtttgtgttcaagagcttgttttaacaaattgttttttttaattatggttaatgaaattattataattacactaatattgaaattggatca
ctaaccatgtgaaatgcttgaattttttagcttgaaaacttcttttgtggacaattttttcttttatctatggattgtgggcatctatgttgttccttt
aagcttcgtacaacctggtctgtgggctggtccagtccttcttactcatgacagtcttttgcagtaaactggttaaacttgggtgacctgttg
acccacccagattggcctgttctttttaaataaaacttggctacttataagatttcaacatgatacttgaatgatcacccttactctaaaggcc
gtttcgttttttcctggcttgaatgctatttcaatgactgggccttattattttctggtttaggttatacaactgtcctccaattgacttttgaatg
cttcaatagttttcttcttaatcatggaaggcactagagtgcatattgaatatgttagaacatggaaggcttaaatatcttttagtctttgcaat
ttaacgttttttgcttttagtccttgcaaaattataattttttttagtcctgactaattatgtttgttttgttttgagggcgagccctggtgcagc
ggtaaagttgtgccttggtgacttgttggtcatgggttcgaatcggaaacagcctctttgcatatgcaagggtaaggctgcgtacaatat
cccctcccccataccttcgcatagcgaagagcctctgggcaatggggtagaaaagaagaatgctttagataacacttttttttgttactgtt
caaagcactatctaaagtgctttgaggactaaacacaaaacaaacataatttgcaaggactgaaaaacaaaaaaataattttgcaagga
caaaaaaacaaaaaaaaaaacaaattgcaaggaccaaaaatatatttaaaccaacatgaaattatggtataaaaccattcatatgtctt
catctaatagcttaagcttttgggatagttggttaacaatatggtattagagtcttatgattttaggtggtctttgagttcaatccttgctgctc
ccagttctagttaatttcttttttggtccacttcaaataaaagttgaatttaagggtaaggcagctggacctgcgcattaatcatgtgtcagg
ctcaaagggcttttgtatgggggcatgtttggaatataatatagaatcattcatgtggtttcacctatcaaggacaactctagttttgtcat
acttgtattattacagtgtctaaactagacatgatctttttccggaaggaaatttaaacttaaaaggaacttagatgcttcttgttctgtgatcttt
tttgctgctcagattctcctttggactatctaccatatcatttagcaaacctgttcactgctcagattctcatttattctttgtttcctctattttttca
gtggcaagttggagagttaaagagactgagaggatgatagcaatctgcacagaactcagaaaggtgagtgtcttgctaattccttt atg
gtttcgatattactggactttttacatctcactgacctactctgtcttggtatttcagctaggagcaacagttgaagaaggtcctgattactgt
gtgattactccacctgagaaattgaatgtcacagctatagacacatatgatgaccacagaatggccatggcattctctcttgctgcugtg
gggatgttccagtaaccatcaaggatcctggttgcaccaggaagacatttccygactactttgaagtccttgagaggttmacaaagca
ctaagcatttgtacattgagtaggaagagagagagagataaatactcacaaaacagtgagtatatgcatggcttgcttttgtttcttaaca
ttcccttgtaagaacttgagataatttgtattgttggaaagagctattgattctgttgtatcaaagtaatttaatttccagtacagacttggctct
```

-continued

```
attcctcatatgtggtggtgtacattgcatctttgcatttgatcccatttctattgggataggaccatacctttttttgtttattattcaagtcaaac ttagcagataatatgtggtgaccagaaaatagtctagctagcaaatagacctgtgattgcatgttlgaattcaggacttcaggacatttaat taatgagtgacaatgttaaaaagctcgccaacaggagttgacacatctgattgagtcttctattaacactaactgtaacttgagtttgattat cagattcctcctgttggtaggtaatatgtaaatttcactatatatttaccgaggttggtggtcttacttgactttgaagaggtgagtgtaattta aactttatatcaaaaaaagattgctaaaagcttgagtggcatgcaacaaatagcaatgaaagaatgactatggccttgggaaccaaatg gccacgtaccacttttccaccaacttgagagccctggtcctggatgatgccccttttttttttttcatttctttgacaataaagaaagttcttattc ttggcaattgcaagtcgtttgtggaagtcacatgaaattcaccataggcttcattgttcaaatcctttagtcactaactaaaggctggaccta tgcaagaattttggctactcttataaatgctgtgcggcaaagactacggaaaaatataaattattgcatatctagaggtgaggttcattgct cccatccattttccaagaactaaatatatataaattattaatatgatattacattgaaaaataatattttcttttaaatatgtgatcataagttta attttaagtctattcatacgaaaaaaatatttattagaaaagattaatttattaaatggatctcaatattttaagaaattaacttttagctctcaac caacagatgatttgagttaaataaaatgtatatataaactattgcatatctgctgattttttgtttgtaacaccaataagtgggcattttactaaat ccatgtgacaatgtactgaatgttttagaatacagtctggtttgataataaaacgtgcataaagtccagcttatgttaactcttaattcatgga aaatgatgatatgcgaattgaaagaaagaaaaccataatgtaagtgcagttttctctctcttttttaatattattcaatatcagattgcacatg ggaagggtattggctcatgtgggatattagttttttgtcccttacctaaaaagagagaaagagaaaaataacaatttaaaaagagtacca ccgctaccacctttttcgcttttaaattttttgttctgttttcactactctttcatgcgttgtttgttggcttctgatagtgacgaatatgatataatga ttttatgttgggaaaaaagtgccatgtaaattctagagattgaaattttagcatcaaattatttattttatcaccttttaaaatttgttgcatgtga agaatttgaagctctccaacaaggaaataacacttcaatccttagagtcatcctctagatcccaaaagaatgtgatgtttatacacattag ggtggtgacactatatggccaaaacaagtgtaatataattattttttttttctcaagtattactctatccttgaatattattagtcttaaatcttcaa gcaccttgtgaacgaagcaatcttgtcc EPSPS 10 reverse                                                                    (SEQ ID No.33)
gcacarcgigcaagigaraaigccatigccat EPSPS 4 torward                                                                     (SEQ ID No.34)
gcwggaacwgcmatgcgiecrytiacigc SEQ ID No. 31 with double mutation                                                  (SEQ ID No.35)
aaaaaatacctttagtaaaataagagcgtragatcaatcagacgttttctctttgggacttctcattcttaattgaattgacaataactaaagt gaaactaaggctaaaatcaactcgcctagtcaagctcgtccacaaaaataggttttttgaaagttttaccatgtcagtttcttactaagtaaaa aaggatcatttgtaaggtccaacgccttaaaatgatcaccttcaaagtaaaagaatcacttgtttcacgcataagtaagaactacgtagg tctgatttcctctccaaaggagggtacgtaggagcaaaagccccgcttttgtcgaccttaaaaaataaaaagaaacaaaagttaaggta acacaatttccacaattctagaaataaggttgttgtctttcgagacaaacgtaagaggtgctaataccttcctcaaacgtaaatacaactcc cgaacttagaattttcattttgaecggtttccttcggttttcccgacgttttccacaaataaacgttggtggcgactccgcgcatctttcctcct ttggaaagcgcacccatgagcctcgccctcgctcgcccgcgaagggcacgttgcgacactaggttaataagaagtttagtccacatat ctatggacctcttaaggtgattatcaaagtggaagtggtgacctacatgttggccctaccagcttattcgtatatttaccccatcaaccat gtatctcagctgaaacatgctatcaatccaaatgttatcagaggaacatgagctgcatgttcaaccagaagtagttctagtcttaatacaa atgtcaaatggcacaagtgagattttgaatttctgatgttgtaaaaatctcaggacatgaatactattgggaagcaattattcatacttcacc aatccaaactgacccaaaattctcaaatcacatgaaagcaaaatgcatataacacgaagaataagaagaagaggaactaacctggg gtttcgatgattaaagcgttgttgttgatgatgaaaacgatgattatggagagaaattgttgttgaatggtgaaattgttatagaaagagaa cgaagatagagaaaagatatatagatttttcaaggctcaaaccctaaaatcaecatgagagagaacaaagattgagaaacctacaac cactatgagagagaatgagcagaacagaagcgtgagatagagaacgagagttaaggtgcgagaggacacgaagaacaaaaggtg tgagagaaagaacaaaggagcctacggtgtgagatgagagaatttgaattcttaccatttaggtggaatttcaattctacaattttattct attaaaattattttaaaaaatgatgtcattttaaattctttaaaatctcatatccaaeaactgaattatgatagaggtatttcaaattcacttaaaa aaattatcttatttaaataccccatccaaacatagcgaaatgttcatgagaaggatcaagtggtttggaaacatagtactaatggtgtttata cagttcatggaatccttgatagataatttaaaggttgctggaaattggatgaaggtgtggagattaaatattcttcc[]iaaataaagcgtttt
```

-continued

```
atttggagagtgttgtgtggttgtctcccotgtaggcaaaagettcgatgtaaaggagttcaatgtccaataacctatgctttctatccctcg
attattgaaaatgaatgacacatttttatttggttgaaatcaagaaataagcatgtggcaagcaacgggtatttgacaattcatagaacaaaa
ggtgaatgcagcaaaagaattaatgaactccttttcgatctacttggatcactacatggagatattatcaacaaatttgatgttactttatgg
agcagttggaattcttggaatgacaagatatgaaatgaacataccaaccctctcttgtttctgtttcggtttctatgcagtattttgttgaatg
gcaaagtgcaagtaatatgctcctcaacatcaattaacaaatgttcatgacatctcttaccagctccaacttggggacgtttgacaaaca
ccaccgtcaagtttccttaaatgcaacattaatgttgctcatttcaaggaggagaatagttttggtgtcggcatgatactccatcaaggaag
attcgtcaaagctcactcacgttttcgacatgggtcgacatgggttacctgacccaaaggctgaggcttaggcttgggtttgcttcaagta
ttgatctgggcccagactattggtttacataatatcattttgaaaacctaacatctaaaactcaaggttgtttagaggtgcgccattccaaa
ataagattatcctatttgtgcatgaatgcgaccaactatctcctgtttcagcattataaagtataaacaacaaacttctttaatcaagggacta
aaagatattggacatacaagctaaaagtgatagaatttgagaaaacaaatattgacaacaatattcaagaggacactaaaacataattct
caaattttttttgtttatttaaaataaagtggttcattaggtagctcttgaaaaaaaaaagtgattaacatgctagtacatgttaaaaaaagtga
ataatattctattataagtaaagaggaataatttatcgatgtctcatttttgagatagttcaccgaagccaattttttttactttttttctcttcaatca
attttattttgttaatagtgtcattgtggatggattataataattttgaaatgatttaaaatgagatatatattaataaatttaattaattcataaata
tgttactaaatataaatttcatggtatactcaggacggttataacggaaatcaaataaataataaaatagaataatattaatttgcagtaaaa
gtttcttatttattaccattttgttcacttctcaattaataaaataaaaatatattctacaattatagtaaaaaggtttaattttatataatgttagca
tatgtaccaaaaagttttaaagcaattattataaaaattaataaatttatcatataaaataatttataattaaattttaaattatcaattcattaaatt
aaacacttataacaaaaaagtaagtaaaaaataaaaaaaagtttttcaataaagtataaactaatttgtataaacttttagaaaaaataaag
aacaatgatttgcaattagatgataatatgaaallatttttacacactacatgtattaaactcaaacttttatatattagttttttctaaaaactaatttt
actactctcttagacaccaaacaacccttcccaaactataatctaatccaaaagccatcattcattttccttggtaggtaaagttccaagacc
ttcaccaacttttttcactcaattgttttggtgtaagcaattcgacatgtgttagtgttagttggcaaccaaaaatccctttatgtgactcaatcc
aacaaccactcacaccaccaacccccataaccatttctcacaataccttcatttacacattatcatcaccaaaaataaataaaaaaaacc
tctcatttcagagagagagagagagacttcacagaccaaagtgcagagaacaacaaagttcacaactttaaggaaaattgaaatggcc
caagtgagcagagtgcacaatcttgctcaaagcactcaaattttttggccattcttccaactccaacaaactcaaatcggtgaattcggtttc
attgaggccacgcctttgggggccctcaaaatctcgcatcccgatgcataaaaatggaagctttatgggaaattttaatgtggggaagg
gaaattccggcgtgtttaaggtttctgcatcggtcgccgccgcagagaagccgtcaacgtcgccggagatcgtgttggaacccatcaa
agacttctcgggtaccatcacattgccagggtccaagtctctgtccaatcgaattttgcttcttgctgctctctctgaggtgaagtttatttatt
tatttatttgtttgtttgttgttgggtgtgggaataggagtttgatgtgtagagtggattttgaatatttgattttttttttgtattattctgtgaaaatg
aagcatcatgtcccatgaaagaaatggacacgaaattaagtggcttatgatgtgaaatgaggatagaaatgtgtgtagggtttttttaatgg
gtagcaataagcatattcaatatctggattgatttggacgtttctgtataaaggagtatgctagcaatgtgttaatgtatggcttgctaaaata
ctcctaaaaatcaagtgggagtagtatacatatctacagcaaatgtattaggtgaggcatttggcttctctattgtaaggaacaaataatat
cagtaatgtgaaaatcaatggttgatattccaatacattcatgatgtgttatttatatgtacctaatattgactgttgtttttctccgcaatgacc
aagattatttattttatcctctaaagtgactaattgagttgcttactttagagaagttggacccattaggtgagagcgtgggggaactaatc
ttgaatacaatctgagtcttgattatccaagtatggttgtatgaacaatgttagctctagaagataaaccctcccccaaaacacaaatta
gaatgacatttcaagttccatgtatgtcactttcattctattattttacaacttttagttacttaacagatgtcttgttcagcataaattataatttat
tctgttttttttttagggaacaactgttgtagacaacttgttgtatagtgaggatattcattacatgcttggtgcattaaggaccctttggactgc
gtgtggaagatgacaaaacaaccaaacaagcaattgttgaaggctgtgggggattgtttcccactagtaaggaatctaaagatgaaatc
aatttattccttggaaatgctggtactgcaatgcgtcctttgacagcagctgtggttgctgcaggtggaaatgcaaggtctgtttttttttttttt
gttcagcataatctttgaattgttcctcgtataactaatcacaacagagtacgtgttcttcttcctgttataatctaaaaatctcatccagattag
ctgagaaatgcacctgagggtgttcctcatgatctacttcaacctctgttattattagattttctatcatgattactggtttgagtctctaagtag
accatcttgatgttcaaaatatttcagctacgtacttgatggggtgccccgaatgagagagaggccaattggggatttggttgctggtctt
```

-continued

```
aagcaacttggtgcagatgttgattgctttcttggcacaaactgtccacctgttcgtgtaaatgggaagggaggacttcctggcggaaag gtatggttggatttcattlagaataaggtggagactttcctggatcaaaattctaatttaagaagcctccctgttttcctctctttagaataa gactaagggtaggtttaggagttgggttttggagagaaatggaagggagagcaatttttttcttcttctaataaatattctttaatttgataca aatatttgtcctccattcccttccttcaaaacctcagttccaaatataccgtagttgaattatattttggaaggcctattggttggagactttt cctttcagagattatccctccctttattatagcctttctattttaaacttcatatagaogccattcttgttttaaaaaacactaagttttcttttta gttataccttccctccttattctctccaaagtaaatattgtagcaagtgttggttgatccattgtgaatcttattatcctatttaacatgcaggt gaaactgtctggatcagttagcagtcaatacttgactgctttgcttatggcagctcctttagctcttggtgatgtggaaattgagattgttgat aaactgatttctgttccatatgttgaaatgactctgaagttgatggagcgttttggagtttctgtggaacacagtgg-taattgggataggttc ttggtccatggaggtcaaaagtacaagtaggtttctatgttttagtgttacatcacttttagtatccaaaatgcaatgaaattaaaactcatgtt tcctattaggtctcctggcaatgcttttgttgaaggtgatgcttcaagtgccagttatttactagctggtgcagcaattactggtgggactat cactgttaatggctgtggcacaagcagtttacaggtattcatgaatgacactatcttctattatctttattttatagcttacactatcattcctaa ttcaacccccttcttttctctttccctcactcccaaaatagagcttatcattgtatccttaatagctcttttatgtgctgtttcatctcttgagcag atttcattaagagtgataaaattacattgtcaagtaaagcaagttagcgtatcagataatgatgcttcgattgcagaattggtgaaagcttg cacaattcattagcttagtgacaattgtgatgtagatagccataatcttccatgcaacttattatgcttttgtctaaaacttcttttgcacttaaa catgaattagagagttaggatgaacaatagtaacagacacaaagcttatttctagaccacccagtggtgaagacgaagcagcatgagt gagattaatggcagcatctgattgaagcttcttttggtattattggagatgaaatcttgagccaaattagggcttttgcctcctcaatagcca ttggttcaaaattgctttcaataaaatgattacagaatcaaattcttaagaaagaccttcaagaacaacatcaagatgtttcctgtgcaaaac aggctcacctacaaaagagtgtctacaagcacctttacacttgcaaaaaattccttaactgaacaattgccaagagtcatgttgcaaactt gagattggagttgattagatttggtgtgtgtgagattctggaaatgagcatgaagttttttgcaaagctcataaaatgaatgcagccaaga atcctagataggattgaatttgagagagaggcttgaagtcaagataaccgcaactgatcttgctgttcccatgctgcataggactcgttg attctaccaagataacaatcttctgtggtgagaatatgagtgggaattgtcaggcaacaaagaaaatgaaggctatgagcctttgttaag gtgcagagagaaaacagaaaatgaagaacttgtgtattgaaggaattgaaaagccaattacaattgtgttgcagagagatatttatagtt ctgaagtgtataactaactaaacagaatgctaccaacctagaggcagttgagaattgctcccttattacaatactctcacagccttgatgat aggcttgatttgctgccaccgaagaagaacattattgttggagagttttttcagtgattgcatcagagaaagttacaagtgtgattggagat gaaggacttgcggtcgtcgaaggttaagtgttaagtggtggaatgtgtatcggaggtggttgcctagcccaagaagctggttgcagtg gaagcggatgcggcagaagccatgggttcagatcagaactatgttctagataccatattagggttagctttcaagagaaaacttatgaa actgaactgtaaactgttgtattattgattagctgatctagtagtgatggaagcttgcttgcgaagcttctatggaggctggatcattgagct tcaatgaggtccttcaatggtgattttcaccatggagatgcagcggaagataaatgaagaggtgagaggaggcgtcatccactagga aataaactatggaagaaggagcttcaccaccaagagagtgtcttggataagaagcttagagaggaagcttcaatggaggaatagaaa gagagaggggaacaaaaaattgaaggaggaaaagagggagagaagttgaactttgaagtgtgtctcacaagactcattcattaaag ttacaacaagtgttacacatgcttctatttatagtctaggtaacttccttgagaagctagaacttaactacacacacctctctaataactaaga taacctccttgagaaatttccttgagaagcttccttaagaagattcctagagaagctaaagcttagttacacacacctctctaataactaagt tcacctccttgagatgagaagctagagccttagctacacacaccccttiitaatagctaaactcactctattccaaaatacatgaaaatacaa aaaagttcctactacaaagattactcaaaatgtcctgaaatacaagactaaaactctatactactagaatggtcaaaatacaaggtccaaa agaaggaaaaacctattctaatatttacaaagagagtggacccaaccttagtccatgggctcagaaatctaccctgaggttcatgggaat cctagggtcttctttagtagctctagtccaattttcttggagtcttctatccaatatccttgggggtaggattgcatcatgtagtacaagagag gggaatatatatacagttgtaagttgtaactacctaatcaaacccaactgactcaccatacacagaaaaacaatgtacaaaggataatag aaaaactgaaactgagatatactcattacatagaagaattacatgatgaatctgaaaattttaattgggaaactgaggacaataacaagg ctttcagagttcattttgacaataggtaaattatggacttcaacttagacctcaagggtatgcttgggagtggggttttagaggaaagggg gaaggagggaaattttttaattctagtaaatattctctattttgattaattttttaaaataaaacaaataaacttatagattagcattcacttaatgt
```

-continued

```
ttttttttacctgtactataactttccaaacaaatagtagaaaatgtttcaaatattcccagaactgtttcagtgaacaaagttcaagccagaa
aaaaagcaagcagaggctaaagaagtatatcttattgtgaagagtaatctcaattggttaattatcgaattgtatcattttacaatagaaaat
tagaagtgggttgattagtttatacgaacaattatttaaatagggttgatggtgtggttaattactgatcatatgttaagactatgagtcgatg
accagcctcagtgcagtcattttaagttccattattttttaattgtgcttatgtttaactttgtccttcttttaaagggagatgtaaaatttgctgaa
gttcttgaaaagatgggagctaaggttacatggtcagagaacagtgtcactgtttctggaccaccacgagattttttctggtcgaaaagtct
tgcgaggcattgatgtcaatatgaacaagatgccagatgttgccatgacacttgctgttgttgcactatttgctaatggtccactgctata
agagatggtatggtttagctgtttgttttttgctcaagagcttgttttcacatatttgtggtcaagagcggtttagctgttttttttttttaaattgtgg
ttaatgaaattattataattatactaatattgaaattggatcactaaccatgtgaaatgcttgaatttttagcttgaaaacttcttttgtggatgatt
tttcttttatctatgtagtgtggggcatctatgttgttccttaagctttgtgtcatagttgtacaacctggtctgtgggctggtccagttcttact
catgactgtcttttgcagcaaactggttaaacttgggtgacctgttgacccacccagattggcctgttctttttaaataaaactccaaaagg
ctacttataagatttcaacatgatacttgaatgaccaccccttactttaaaggtcattatgccatcagaccccttgattctctgttcagttatgttc
ttattccttattattttttaatttatattattatccaacgatctgatctttgtacatgatgctggacaatcatcaaagctagtttggttacatcatataa
aatactatttcaatgactgggccttattattttctggtttgggttatacaactgtcctttgatgtacttttgaatgcttcaatagtattttttcataatc
atggaaggcactagagtgcagtgcatattgcacaaggttctttaatggcatcttgaatttgttagaacatggagttatgatatacaaccatt
cctatgtcttcatctaatagctaaagcttttggcgtagttggttaacatggtattggaatcttattttaaaggtccatcttattcgcaagtacaa
ggcaggtggacctgcgcattattcacgtgccaggctcaaagggattttgtatgagggggaattttttggaatataatatatagaatcattca
tgtggttcacctatcatgtgtcaactcaagttttttgtcctagttgtattattgcagtgtctaaactaggcatgatcttctgtggaaggaaattta
acctaaggaacttgaatgcttcttgttctgagatcttttatttttttttctccaatcttttttaatacttgaaaggttttagttgtatctataaagggtgc
agaattaggggggtcagcttttctgttgtaagcgtgaattaagtgcatttttatgttgttccctattttatacatttgaactatcaaccatatcattta
gcaaacttctttgttgctcagattcccatttattcttgtttcctctattttttagtggcaagttggagagttaaagagactgagaggatgatagc
aatctgcacagaactcagaaaggtcttgctaattcctttatggtttctatattactggacttttttacatctcactgacctactactgtcttggtat
ttcagctaggagcaacagttgaagaaggtcctgattactgtgtgattactccacctgagaaattgaatgtcacagctatagacacatatga
tgaccacagaatggccatggcattctctcttgctgcttgtggggatgttccagtaaccatcaaggatcctggttgcaccaggaagacatt
tcctgactactttgaagtccttgagaggttaacaaagcactaagcattttgtacattgagtagggaagagagagagatatatataaatact
cacaaagcagtgagtatatggcttgcttttgtttctaaacattcctttataaggacttgagataaatttgtattgtttaaaagagccattggttct
gttgtatcaaagtaattaatttcagtaccgacttggctctactcatatgtggtggtgtacattgcatctttgcatttgattccatatctattgg
gatgggaccatacatttttttgtttattatttaagtcaaacatatcagataatatgtggtgaccagaaaagtgtctagcaatcaaatgggtctgt
gattgcatgtttgagttcaggacatttattaatgagtgacagaattttaaaaagctcgccaataggagttgccacatctgatcgagtcttctg
taaacactaactgtaacttgagtttgataatcagattcccccgttggtaggtaatatgtaaatttcactatagattcttactgaggatgatgg
tcttgacttcgaagtggtgagtgtaattctctaatctaaactttatatatatataaaaaagaatgttaaaaacttgagtgacatacagcaaat
agcaatgaaagcatgaccatggccttgggggccaaatggccatgtaccacttttccacctacttgagagccatggtcctgaatgaggt
cctttttgtttcatttttttacaataaagaaagttcatattcttggcaatagcaaggcaaatcatttgtggaagtcacatgaaattcaccatagg
cttcattgttcaaatcctttagtcactaaggcagggcctatgtaagaattttgactactcttgtaaatgctgtgcggtaaagactacgggaa
aatataaattattgcatatctagaggtgaggttcatttctccgatccatttctccaagtaataaaaatatatataaattattaatatggtatgata
tggttatttgtcctttaaatatgcgattataggttcaatctttggttaatctatcaaatgcatctcaatattttgagagaatagtttttagctcttga
ctgagagatactttgagttaaaaaaatgtatttataaactattgtctattgattttttatttttttttgtaacaccacatgtgagtattttactaaatcc
atgttacaatgtactgaatgttttacaatacagtctggtttgataataaaatatgcacaaagtccagcttatgtaactctttcaattcatggaaa
atgatgatatgcgaattgaaagaaagaaaaccataatgtaagtgtattttttttttctttctcttctttaatattactcaatatcagattgcacatg
ggaagggtactggctcatgtgggatattaattttttatcccttacctaaaaagagagaaagagaaaataactatttaaaaagagtaccacc
accacctttttcgcttttaagttttgttctgttttcactactctttcatgcgttgtttgttggcttccgatagtgacgaatatgataatgattttacgt
```

-continued tgagaaaaaaaatgtgccatgtaaattccagagattgaaattttagcttcaaattaatatttattttattatctttttcaaattggttgcatgtgaa[]
agaatttgaagttcttcaacaaggaaataaacacttcaatgctcaatccttagagtcagtcactagatcccaaaagaatgtgatgtttacac
acattagtatatatatatatataaacacagcttatattatattaatgagtgatgcgcgaggacggtggtgacactacatggccaaaacaag
aaatgtaatttaatttttttttctttaagtattactctatccttgaatattagtcttaaatcttcaaagaccttgcgaacgaagcaatcttgtcctga
tcctgtgattgttctacactagtccttacgtgtacctaagcacatgatactttgctgccctaacataaattgtaccataaggattcttgggga
gatgcttttgccttcattttcaagtttgtttacactttcaagtcgttttttcaatgcattctctttcctttctgggaccccttgtctttaacacgcgc
gcacacaaaaactagtagacaataattagtactacttgggttccattaaattgtaactacatatacatgtgtttttttttttcttggatcaactgc
atatacatgttttatgagtttcattgaatttatatttacacaaacagttattaaaacataatgtagagccttgtcattaacctgatgttaggatt
ccgttcaaaagagagacgacaaggataatactaatactagtagattccacgcattcaaccctagttagtttagctatgacaaattaagcat
ggtaagaaaaggggaggagaaagtaagaatgaacatataacaaattgtgattgaacttttccatgacgtaatgaaaacattaattttt
aagataagcttcaactcctaagaagagatatgtcaaagaaacttaggattttttctctatttataacggtaaattactcatccttttaaatgatt
aatttgcgttgttgaattcgttgtaaagggaaaatcaagaagtctcttcacgggaaagttatatcaaagtatcatatactagacttcatggct
agcttttactttgattataagtaatgcatgcaattaatgggcaaataaattatttgaaaccaactaaagtacaaataattttcctccaaaacct
ctcaagttcgcattgaaattaaataaaccaatgcatattaaggcgtaaatctaaaccatgttttgtttcatcttgtattgtatatcatagtattaat
aaggtactttgaatttagttgttattgaccgttaaatttagggggtgagttgttttactatctcttactcaattgcttttattcaacgcaaattctagt
aggattttcagcccaaattaaaagaagttttacggtttgattctctacaaacttgaattgagatttctaatttcagaaatcaataattgcggtct
taattaactctataatcaaaccttttaacccaatctttttctcaattctctgaattaagacaatcaaaatttaaactcacacgaatctcacacgc
cttcccacggtagagaaatatagggagtcccttaatagcaaaagcctcaaaattcagaaaatctcatccattgcatttgcacattcaacaa
accacccattattatgttcccttaataaatctcacacttaaaaaccctcctcacccataattaacccaaaaggaagtttcctccacacaaaa
aatatccttaaacaaagagcctctataaatctatttaaaaaaaccccccaaatttaagga SEQ ID No. 32 with double mutation                                                         (SEQ ID No. 36)
aaaagtctgaatgaagtgaagttgttgtgttaggggatgctgaatttgattttaatttaatttaaataaattacctgtgtaaaggattlttgta
ccgccttttaatcacaaattgtcgtgtatcgaaagtttgttgaatttttatagtaactatcttggaggttataccctagtaggatttctgattagtta
accatgtaaattttttttaatgggtttgtgtttgttttaactgatgttgttttttgatatgtacgtggtaagtgtgatgagtttgtgcatatcttgatca
aagactgaagtgaagttgttgtgtttggggggttgactcttttaggaagaggatttgagggaatttcgecaatggggagcagaactcc
gggacaccctgagaattttgagactccgggaattgaagttacaacaggtttgatatgagttagagtttgtataatagaatagtaattctttttt
atttttttatttttattgtttatttatccattattgctattttgtaggtcctcttggtcaggggattgccaatgctgttggtttggcccttgcagagaa
gcacttggctgcaagatacaacaagcctgacaatgagattgttgaccattacaegtaaaaataactaaatcatacacaacttgcaagact
ttagttgttggtgttttgctaatggcgtttgttttatgcaggtatgctattctgggtgatggttgtcaaatggagggaattgcaaatgaagcat
gctcacttgctggccactggggactggggaagctgatagcatttttatgatgacaatcatatttctattgatggtaacacagagattgcgtt
caccgagagtgttgatagtcgttttgagggacttgggtggcatgttatttgggtaaagaatggaaataatggctatgatgatattcgtgct
gccattaaggaagcaaaagctgtcaaagacaaacccacattaatcaaggttagtttactaattgtggctgatatgcatagatttctggc
ttgtagttaccataacaatcataatctgtcatgatttatagggattcttttaaactaaggttataaacatgatatgttactaaagactgcattgc
attgtagtacctcatttgagaaactggaagttataggtgggaaatcaaaatagtaaattatgggtcagtttattaagtgtagctggtttgtctt
ttgctaactctatcatttcacaggtcaeaacaaccattggttatggttctcctaacaaggctaactcctacagtgtgcatggaagtgcactg
ggtgccaaagaagttgatgccaccaggcagaaccttggatggtcacatgagccattccacgtgcctgaggatgtcaaaaagtatggat
gatgggtttagagatttctttttttcctgtgaeactgctgatgtttataatgatactgaataagaattgcttgtctgtcccaggcattggagtc
gccacacccctgagggtgctgcacttgaagctgagtggaatgctaagtttgctgagtatgaaaagaaatacaaggaggaagctgcag
aattgaaatctattatcaatggtgaattccctgctggttgggagaaagcacttccggtgagtaaattct[]actcacaggttttttcttacatgt
ttgtaacttttcaaggtttggattacatactatccaagttgatcatgatttcagtttgatttggtagtatggggcttcaaaaagttattccaaat -continued

```
attaaaacetggcttccaatttgatttcagacatacactecagagagcccagcggatgccaccagaaacctgtctcaaacaaaccttaat
gcccttgcaaaggttcttcccggtctgcttggtggcagtgcagatcttgcttcttccaacatgaccttgctcaaaatgttcggggacttcca
aaaggatactccagcagagcgtaatgttagattcggtgttagagaacacggaatgggagctatctgcaacggcattgctcttcacagec
ctggactgattccatattgtgcaaccttetttgtattcactgactacatgagaggtgccataaggctttctgcgctgtctgaggctgggtta
tttatgtcatgaeccatgattcaataggacttggagaagatgggccaacccaccagcctattgagcacctagcaagcttccgggcaatg
ccaaacattttgatgcttcgtcctgccgacggtaacsgaaacagccsgagcatacaaagtggccgtgctcaaeaggaaagagaccct
ccattcttgccctatccaggcaaaaactgccccagcttcccggaactthcattgaaggagttgaaaagggtggttacaccatttcggga
caactccactggcaacaagcctgatgtcattttgatcggaactggttcggaattggaaatcgctgccaaagctgctgatgacctaagga
aggaagggaaggctgttagagttgtttcccttgtttcttggggaactttttgatgagcaatcagaagcatacgggagagtgttttccctg
ctgctgtttcagccagagttagcattgaggcaggatcaacatttgggtgggagaaaattgttggagcaaagggaaaagcaataggcat
tgatcgttttggagctagtgctccagctggaagaatatacaaagaatttggtatcactttggaagctgttgttgctgcagctaaagagctt
atctagaacttttgatttttttttgccttctggttttggttgagagcattccatgtcatgaataagaaaaggttaaatatccttcgattgggaat
ttgggattctaagtgaagaagcaacatagatcaaagaattttgtgaacttgtaataactatttgacaatttagttttgcactgccacatggtta
aattcaatgtttgatcatatcaaccatagatgctagtttatactacttgtataatttgtttcacttgcagattcactcttagcatttgagtgtttgg
atggccgtgttttgttcattaagaaatgttgacatggatagtttgttgcatggtaaattggtgattaataccttttaagcttcttttggcaagtt
gttaaaaagtgttttgttttaatctctagttaatctaaaaatgcctacttattttatttttgactttcaaaacttgtctatatgccgagtataaaaaaa
acttgtctatataagttccttatggaaaaaggacctacaaaataatttaaaaatgctgaatttgttaggaagtttgacaactttagacatWzaat
aattgtttttttttcatatatataattgactttcaaaacttgtctatatattataaattcgttatggaaagggcgaccacacgtaaaacgtaacat
gccaatctctccctagtgaactgttattctcattcagttttgtaagttcaccttcaaattttcaatttttttttgacaaaaatatctttgatggaac
acgttagggtgtaaattcaccattcatcatttcattcattatacacaatagtctttcataatccaatgaaaacttgttttgttgttattttttctg
aaaaatctttataaaataaataaaaacattttttgttataaatttcagttgaaatacataaccattaattctacagagtgttaatgttgatgtaaa
ataaaaaatattggatatcaaacttaatgaacagaacaaaaattacaaaattgtacaatttaaatgataaaaaaccaaattcacaaaaata
aaaattaaggacgaaatttgagaaatgataattaaaaacgattaaaaatataattaaactaaaatttattatgtaattctttaatatatatatata
tatatatatatatatatatatatataataaaagttttacattataattttgaaatgaagtatttgataaacgaacaacccaccttggg
gttggtgagagtgaaacggagaacagtgtctcectcacttggtcttctgagtcgagtcctattcatcaccaacccactcgtcaaaattgtt
atttcagttcctagttgctacaacttccagctggtgaaaaatagtcaacagagactacaatattctaataaaatagaataacaaaatc
aaaaatttctacaattatagaaaaagtttagttttgtagattgttaacataaagattttcctattaactaattaatta[]aaagtcatcttatatataa
gttttaaagtaattatcttatatatgtacccaaaagttttaaagcaattattataaaaaagtaaaatttttatcatatacaataatctataattacat
atttattccactttttaccaataaatttcctcataaacacttataagaaaaaagtaagtaaagaataaaataagctttttctataaactataaac
ttttttaagaaatttgttcaaacatatttttatgacatgtcaatgcttgagagatataaggtgagttaaatcataaatgattaaagaaaaataaa
agaagaaaagataattaatttaattttttattaacattctaacaaattaacattatataaataaaaataatatttcaataattggatcaataatac
tattgttcttaaacaccaaaccaaccttcctaaagtcctaatctaatccaaaagccatcattcattUccttggtaggtaaagttccaaaacct
ttaccaaccttttcactcaattattttggtgtaagcaattcgacatgtgttaatgttagttggcaaccaaaaacccctttatgtgactcactcaa
tccaacaacctctcacaccaccaacccccccataactcataaggccaaaaccatttctcacaaaacccttcattacacacattattatcatt
atcacacacacaaaaaacctctcatttcaaagagagagagagatttcacagaccaaattgcagaggacgacaaagttcacaacttcaa
ggaaaatcgaaatggcccaagtgagcagagtgcacaatcttgctcaaagcactcaaattttyggycattcttccaayyccaacaaacy
caaatcggygaattcggtttcattgaggccacgcctttgggkscctcaaaatctcgcatcyygrtgmayaaaamtggaagcyttat
gggaaattttaatgyggggaagggaaattccggcrtgtttaaggtttctgcatcsgtcgccgccgccgcagagaagccgtcaacgtcg
ccggagatcgtgttggaacccatcaaagacttctcgggtaccatcacattgccagggtcyaagtctctgtccaatcgaattttgcttcttg
ctgctctctctgaggtaaagtttatttatttattttatttctgtatccaaaaatgtaaattgttagtttgttaattttttgttagcagtgagagtcgaact
```

-continued

```
acttggcttctttcttagtcatccaaccaaccttatatctccaaaatttatttattggttttttttggggttatgtggttaggaataggagtttgatg
cgtggagtggattttgaatatttgatttttttttttttgtattattcagtgaaaatgaagcatcttgtcccatgaaagaaatggacacgaaatta
agtggcgtatgatttagaatgatgatagaaatgtgtataggtggttttaatgtgtagcaataagcatattcaatatctggattgatttggacg
tttctgtataaaggagtatgctagcaatgtgttaataatgtcttgttaaaagtatggatggctaaaataatcataaaaatcgagtgggagta
gtatacatatctacaggaaatgtattaggtgaggcatttggcttctctattgcgagtaaggaacaagtaatctcagltaatgtgaaaatcaa
tggttgatattccaatacattcatgatgtgttatttacgggaacgcaatattgactgttgattttatctgcagctgagattatatactatatccttt
ccaaagaaatctttgactcttgattatccaagtatggttgtattaccaatttagctctagaagataatccctcccccaaaacacaaattaga
tttttattcttatttagggaacaaetgttgtagacaacttgytgtayagygaggatattcattacatgcttggtgcattaaggaccccttggact
gcgtgtggaagaygacmaaacaaccaaacaagcaattgtkgaaggctgtgggggattgtttcccactaktaargaatctaaagatga
aatcaatttattccttggaaatgctggtactgcratgcgtcctttgacagcagctgtrgttgctgcaggtggaaatgcaaggtctgtttttttgt
tttgtttgttcatcatgatctctgaattgttcctcgtataactaatcacatcagactatgtgttcttcctccatcctgttataatctaaaaatctcat
ccagattagtcatccttctttaaatgaacctttaattatatctatgtatttatttaacatgtaaattagcttgtcaagtcaaagtctagcatataga
tatactgattacactctgaggaatgcacctgagggtcttaatcatgatctatttcaaccttgccactttcttcttttattattagatcacctatcat
gattactggtttgagtctctaaatagaccatcttgatgttcaaaatatttcagctacgtacttgatggrgtgccccgaatgagagagaggcc
aattggggatttggttgctggtcttaagcaictyggtgcagatgttgattgctttcttggcacaaactgtccacctgttcgtgtaaatggga
agggaggacttcctggcggaaaggtatggtttggatttccattagaataaggtggactaactttcctggagcaaaattctaatttatacct
gtttcccctctttagaataagacactaagggtatgtttaggagttgggttttggcgagaaagggaagggagggcaatttttttttctaataa
cctctatttaaaaacaagatattttcctccattcccttccctttaaaacctcagttccaaatataccgtacttgaattatattttggaaggtgta
ttggttggagaccttcctttcagaggttatccctcacctttattatagccttctactctcttaatgagttcattgtgcattgagtcattgaactt
cctgtgaaaagaaattgtttacttttctttatttgttacctacatccttattcctgttttaaaaaatactaagttttcttttagttatgccttcccctcc
ttattctctccaaagaaaatataatagcgaatgttggtttatccattgtgaatcttattatcctatttcacatgcaggtgaaactgtctggatca
gttagcagtcaatacyractgctttgcttatggcagctcctttagctcttggygatgtggaaattgagattgttgataaactgatttctgttc
catatgttgaaatgactctgaagttgatggagcgttttggagtttctgtggaacacagtggtaattgggatargttcttggtccatggaggt
caaaagtacaagtaggtttctatgttttagcattacatcacttttagtatccaaaatgcaatgaaatcaaaactcatgttttctatcaggtctc
ctggcaatgcttttgttgaaggtgatgcttcaagtgccagttayttmctagctggtgcagcarttactggtgggactatcactgttaatgg
ctgtggcacaagcagtttacaggtattcatgcttgacactattttctattatcttttattttatggtctatactgtatcattcctaattcaacccccct
tcttttctctttcccctcacttccaaaaaaatagagcttatcattgtattcttaatagctcttgtatgtccttttttcgtctcttgagcagattctacc
tatttcattaacagtgataaagataaaaataaattgtcaagtaaagcaagttagcatgtcagataatgatgcttcaattgcaaaattggtgaa
agcttgcacagtacattagctttggtgacaattgtgatgtagatagccataacctcccatgcaacttattatgttgtttgcttaaacttcttttg
cacttaaacacggattagagagagtgaggatgaacaataataacagacacaaagcttagttttataccacccggcacccagtggtgaa
gaccaagcagtatgagtgagatcaatggcagcatctgattgaagcttcttgtggtattttttggagatgaaatccgaggcgaattagggca
tctggctcaacaatagccattggttcaaacttgcttttaataaaattgattacagaatcaaattcttgaggaagccttcaagaactacatcat
gatgttccctgtgcaaaacaggttcaccgacaaaagagaacatctacaagttccttacatgccaaaaattcctcaactgaacaattg
ccaagagtcatgttgcgaacttcaggttggagttgacgaaatttggtgcatgtatgattctggaaatgagcatgaagttttttcctaagctc
ataaaagtgaatgcagccaagaaccctagataggattgaatcggagagaggcttgaagccaagataacagcaactgatcttgctgttc
ccatgctgcgtaggactcattgattctaccaagatcacaatcttctgtggtgagaaaatgagggtgaattgtcaaccaataaagaaaatg
gtgaaggctgagtcttgatgataggcttgatttgcttgcgctgaagaagaacgttattgttgtagagtttctcagtgattgtatgagagtaa
gttacaggtgcgattggagatgacggacttgtggtgggaggagggtaagtgttaagtggtggaatgcgtatcagaggtggttgccca
gccaaagaagctggttgcggtggaggaggtggtggtgcagtggaagccatgggttttgatgcttttgagagaaaacatacgaaactg
aactgtaaacttttgtattattgattagctgatttggtagtacaagagaggaatatatatacagttttaatgtaactacctaaccaaacatgag
```

```
gaactctccatacacagaaagacgtatacaaaggataacagacaaacagaaacttagatatactcatacagagaagaattacaggatg
aatctgagaattttaattgggaaactgaggaaaatagcaagggtttcagaattcattttgacgataggcaaatcatggacttaacttagac
ctcaagggtacgcttgggagtgggggtttttagagggaaaagggaaggagggcaaacttttaattcctaataaatattctcttttttgatttt
ctatagtatgtataactattcaaataaatagtagaaaatgtttcaaatattccccagaactgtttcagtgaacaaagttcaagccagaaaaa
agaagtatatcttcttgtgaagagtagctcaagtggttaattgtcaaatttgtatcattttagaatacaaaattagaagtggtttgattagtttat
acgaacgattatttaaataggggttgatgatgtggttaattactgatcatatgtgaagactgtgagtcgatgaccagcccagtgcagtcattt
taaattccattattttaatttgtgcttatgttaaactttgtccttctttcaaagggagatgtaaaatttgctgaagttcttgaaaagatgggagc
taaggttacatggtcagagaacagtgtcacygttwctggaccrccacragattyttctggtcraaaagtcttgcraggcattgatgtcaat
atgaacaagatgccagatgttgccatgacwcttgcygttgtygcactatttgctaatggtcmmactrcyatmagagatggtatggttt
agctgtttgtttgtgttcaagagcttgttttaacaaattgttttttttaattatggttaatgaaattattataattacactaatattgaaattggatca
ctaaccatgtgaaatgcttgaattttttagcttgaaaacttcttttgtggacaattttttcttttatctatggattgtgggcatctatgttgttccttt
aagcttcgtacaacctggtctgtgggctggtccagtccttcttactcatgacagtcttttgcagtaaactggttaaacttgggtgacctgttg
acccacccagattggcctgttcttttaaataaaacttggctacttataagatttcaacatgatacttgaatgatcacccttactctaaaggcc
gtcgttttttcctggcttgaatgctatttcaatgactgggccttattattttctggtttaggttatacaactgtcctccaattgacttttgaatg
cttcaatagttttcttcttaatcatggaaggcactagagtgcatattgaatatgttagaacatggaaggcttaaatatcttutagtctttgcaat
ttaacgttttttttgcttttagtccttgcaaaattataattttttttttagtcctgactaattatgtttgttttgttttttgagggcgagccctggtgcagc
ggtaaagttgtgccttggtgacttgttggtcatgggttcgaatccggaaacagcctctttgcatatgcaagggtaaggctgcgtacaatat
ccctcccccatacctttcgcatagcgaagagcctctgggcaatgggtagaaaagaagaatgctttagataacactttttttgttactgtt
caaagcactatctaaagtgctttgaggactaaacacaaaacaaacataatttgcaaggactgaaaaacaaaaaaataattttgc[]gga
caaaaaaacaaaaaaaaaaacaaaattgcaaggaccaaaaatatatttaaaccaacatgaaattatggtataaaaccattcatatgtctt
catctaatagcttaagcttttgggatagttggttaacaatatggtattagagtcttatgatttttaggtggtctttgagttcaatccttgctgctc
ccagttctagttaatttcttttggtccacttcaaataaaagttgaatttaagggtaaggcagctggacctgcgcattaatcatgtgtcagg
ctcaaagggcttttgtatgggggcatgtttggaatataatatagaatcattcatgtggtttcacctatcaaggacaactctagtttttgtcat
acttgtattattacagtgtctaaactagacatgatcttttccggaaggaaatttaacttaaaaggaacttagatgcttcttgttctgtgatcttt
tttgctgctcagattctccttttggactatctaccatatcatttagcaaacctgttcactgctcagattctcatttattctttgtccctctatwj[]ca
gtggcaagttggagagttaaagagactgagaggatgatagcaatctgcacagaactcagaaaggtgagtgtcttgctaattcctttatg
gtttcgatattactggacttttacatctcactgacctactctgtcttggtatttcagctaggagcaacagttgaagaaggtcctgattactgt
gtgattactccacctgagaaattgaatgtcacagctatagacacatatgatgaccacagaatggccatggcattctctcttgctgcttgtg
gggatgttccagtaaccatcaaggatcctggttgcaccaggaagacatttccygactactttgaagtccttgagaggttmacaaagca
ctaagcattttgtacattgagtaggaagagagagagagataaatactcacaaaacagtgagtatatgcatggcttgcttttgtt-tcttaaca
tcccttgtaagaacttgagataatttgtattgttggaaagagctattgauctgttgtatcaaagtaatttaatttccagtacagacuggctct
attcctcatatgtggtggtgtacattgcatctttgcatttgatcccatttctattgggataggaccataccttttttgtttattattcaagtcaaac
ttagcagataatatgtggtgaccagaaaatagtctagctagcaaatagacctgtgattgcatgtttgaattcaggacttcaggacatttaat
taatgagtgacaatgttaaaaagctcgccaacaggagttgacacatctgattgagtcttctattaacactaactgtaacttgagtttgattat
cagattcctcctgttggtaggtaatatgtaaatttcactatatatttaccgaggttggtggtcttacttgactttgaagaggtgagtgtaattta
aactttatatcaaaaaagattgctaaaagcttgagtggcatgcaacaaatagcaatgaaagaatgactatggccttgggaaccaaatg
gccacgtaccacttttccaccaacttgagagccctggtcctggatgatgcccttttttttttttcatttctttgacaataaagaaagttcttattc
ttggcaattgcaagtcgtttgtggaagtcacatgaaattcaccataggcttcattgttcaaatcctttagtcactaactaaaggctggaccta
tgcaagaattttggctactcttataaatgctgtgcggcaaagactacggaaaaatataaaattattgcatatctagaggtgaggttcattgct
cccatccatttttccaagaactaaaatatatataaattattaatatgatattacattgaaaaataatattttt-tcttttaaatatgtgatcataagttta
```

-continued attttaagtctattcatacgaaaaaaatatttattagaaaagattaatttattaaatggatctcaatattttaagaaattaacttttagctctcaac caacagatgatttgagttaaaaaaatgtatatataaactattgcatatctgctgattttgtttgtaacaccaataagtgggcattttactaaat ccatgtgacaatgtactgaatgttttagaatacagtctggtttgataataaaacgtgcataaagtccagcttatgttaactcttaattcatgga aaatgatgatatgcgaattgaaagaaagaaaaccataatgtaagtgcagttttctctctcttttttaatattattcaatatcagattgcacatg ggaagggtattggctcatgtgggatattagttttttgtcccttacctaaaaagagagaaagagaaaaataacaatttaaaaagagtacca ccgctaccaccttttttcgcttttaaattttgttctgttttcactactctttcatgcgttgtttgttggcttctgatagtgacgaatatgatataatga ttttatgttgggaaaaaagtgccatgtaaattctagagattgaaattttagcatcaaattatttattttatccttttaaaatttgttgcatgtga aagaatttgaagctctccaacaaggaaataacacttcaatccttagagtcatcctctagatcccaaaagaatgtgatgtttatacacattag tatatatatatatatatatatatatatatatatatatatatatatatatatatatatatataggtttatattatattaatgagtgatgtacgaggac ggtggtgacactatatggccaaaacaagtgtaatataattatttttttttctcaagtattactctatccttgaatattattagtcttaaatcttcaa gcaccttgtgaacgaagcaatcttgtcc FMVS35S90 enhancer (SEQ ID No.37)
aagcttcccgggccggccgcagctggcttgtggggaccagacaaaaaaggaatggtgcagaattgttaggcgcacctaccaaaagc atctttgcctttattgcaaagataaagcagattcctctagtacaagtggggaacaaaataacgtggaaaagagctgtcctgacagcccac tcactaatgcgtatgacgaacgcagtgacgaccacaaaactcgagacttttcaacaaagggtaatatccggaaacctcctcggattcca ttgcccagctatctgtcacttttattgtgaagatagtggaaaaggaaggtggctcctacaaatgccatcattgcgataaaggaaaggccat cgttgaagatgcctctgccgacagtggtcccaaagatggaccccacccacgaggagcatcgtggaaaaagaagacgttccaacca cgtcttcaaagcaagtggattgatgtgatatctccactgacgtaagggatgacgcacaatcccactatccttcttaattaa FMV35S46 enhancer (SEQ ID No.38)
aagcttcccgggccggccgcagctggcttgtggggaccagacaaaaaaggaatggtgcagaattgttaggcgcacctaccaaaagc atctttgcctttattgcaaagataaagcagattcctctagtacaagtggggaacaaaataacgtggaaaagagctgtcctgacagcccac tcactaatgcgtatgacgaacgcagtgacgaccacanaactcgagaacatggtggagcacgacacacttgtctactccaagaatatca agatacagtctcagaagaccagagggctattgagacttttcaacaaagggtaatatcgggaaacctcctcggattccattgcccagct atctgtcacttcatcgaaaggacagtagaaaggaagatggcttctacaaatgccatcattgcgataaaggaaaggctatcgttcaaga tgcctctaccgacagtggtcccaaagatggaccccacccacgaggaacatcgtggaaaaagaagacgttccaaccacgtcttcaaa gcaagtggattgatgttaattaa GmTerm Barn (SEQ ID No.39)
ctgcagggatcctggttgcaccaggaag GmTermEco (SEQ ID No.40)
gaattcccgggtatggtgaatttcatgtg BnMUT2PST (SEQ ID No.41)
gacttctcgggtaccatcacattgc BnMUTkpn (SEQ ID No.42)
cacctgcagcaaccacagctgctgtcaaagaacgcattgcaataccagcatttcc GmRubPac (SEQ ID No.43)
aatttaattaattcataaatatgttac GmRubbot (SEQ ID No.44)
ggtcttctccttcttagttctcaactacttgttcttctgctgccagatttcaattttccttaaagttgtgaac GmRubtop (SEQ ID No.45)
atctggcagcagaagaacaagtagttgagaactaagaaggagaagaecatggcccaagtgagcagagtgcac GmRubKpn (SEQ ID No.46)
ggcaatgtgatggatcccgagaag ZPPDK1 (SEQ ID No. 47)
gcgccatggcggcatcggttttccaggg ZMIPPDK2 (SEQ ID No. 48)
gcgggtacctcagacaagcacctgagctgcagc

| | |
|---|---|
| EcPPS1<br>gcggcatgcccaacaatggctcgtc | (SEQ ID No. 49) |
| EcPS2<br>gcggatccttatttcttcagttcagcca | (SEQ ID No. 50) |
| EPSPS motit<br>ALLMZAIPLA, wherein Z is not S or T | (SEQ ID No. 51) |
| EPSPS motit<br>EIEIZDKL, wherein Z is not V | (SEQ ID N6. 52) |
| EPSPS motit<br>FG(V/I)(K/S)ZEH, wherein Z is not V | (SEQ ID No. 53) |
| EPSPS motit<br>AL(K/R)ZLGL, wherein Z is not R | (SEQ ID No. 54) |
| EPSPS motit<br>GLXVEZ$_1$DXZ$_2$XXXA(I/V)V, wherein Z$_1$ is not T and/or Z$_2$ is not E | (SEQ ID No. 55) |
| EPSPS motit<br>ITPPZ$_1$K(L/V)(K/N)Z$_2$, wherein Z$_1$ is not K and/or Z$_2$ is not T | (SEQ ID No. 56) |
| EPSPS motit<br>TIZ(D/N)PGCT, wherein Z is not N or L | (SEQ ID No. 57) |
| EPSPS motit<br>(D/N)YFXVLXZXX(K/R)H, wherein Z is not K | (SEQ ID No. 58) |
| EPSPS motit<br>(I/V)VEGCGG(I/L/Q)FP(V/A/T)(S/G) | (SEQ ID No. 59) |
| EPSPS motit<br>(I/V)VVGCGG(J/L/Q)FP(V/A/T)E | (SEQ ID No. 60) |
| EPSPS motit<br>(I/V)VVGCGG(I/L/Q)FP(V/A/T)(S/G) | (SEQ ID No. 61) |
| EPSPS motit<br>(I/V)VVGCGGKFP(V/A/T)(S/G) | (SEQ ID No. 62) |
| EPSPS motit<br>(I/V)VEGCGGKFP(V/A/T)E | (SEQ ID No. 63) |
| EPSPS motit<br>(I/V)VEGCGG(I/L/Q)FPV/A/T)E; | (SEQ ID No. 64) |
| EPSPS motit<br>(I/V)VEGCGGKFP(V/A/TXS/G). | (SEQ ID No. 65) |

---

The invention claimed is:

1. An isolated polynucleotide comprising the following components in the 5' to 3' direction of transcription:
   (i) at least one transcriptional enhancer selected from the group consisting of SEQ ID NOs 29, 30, 37 and 38;
   (ii) the soybean genomic sequence set forth in SEQ ID NO: 31 which comprises the promoter from the soybean EPSPS gene, and a coding sequence which encodes the soybean EPSPS chloroplast transit peptide and the soybean EPSPS enzyme; and
   (iv) a transcriptional terminator;
   wherein the soybean EPSPS coding sequence is modified in that a first position is mutated so that the residue at said first position is Ile rather than Thr and a second position is mutated so that the residue at said second position is Ser rather than Pro, the mutations being introduced into EPSPS sequences which comprise the conserved region GNAGTAMRPL (SEQ ID NO: 66) in the wild type enzyme such that the region in the modified sequence reads GNAGIAMRSL (SEQ ID NO: 67).

2. An isolated polynucleotide comprising the following components in the 5' to 3' direction of transcription:
   (i) at least one transcriptional enhancer selected from the group consisting of SEQ ID NOs 29, 30, 37 and 38, a sequence that comprises the promoter of a *Brassica napus* EPSPS gene;
   (ii) a *Brassica napus* genomic sequence which comprises the promoter for a *brassica* EPSPS gene and which encodes a *Brassica napus* EPSPS chloroplast transit peptide and a *Brassica napus* EPSPS enzyme coding sequence; and
   (iii) a transcriptional terminator;
   wherein the *Brassica napus* EPSPS coding sequence is modified in that a first position is mutated so that the residue at said first position is Ile rather than Thr and a second position is mutated so that the residue at said second position is Ser rather than Pro, the mutations being introduced into EPSPS sequences which comprise the conserved region GNAGTAMRPL(SEQ ID NO: 66) in the wild type enzyme such that the region in the modified sequence reads GNAGIAMRSL(SEQ ID NO: 67).

3. The polynucleotide according to claim 1, further comprising a sequence which encodes a chloroplast transit peptide/phosphoenolpyruvate synthase (CTP/PPS) or a chloroplast transit peptide/pyruvate orthophosphate di-kinase (CTP/PPDK), which sequence is under expression control of a plant operable promoter.

4. The polynucleotide according to claim 3, wherein the CTP and PPDK encoding sequences are non-heterologous with respect to each other.

5. The polynucleotide according to claim 1, comprising at least two of said transcriptional enhancers which are tandemly present in the polynucleotide.

6. The polynucleotide according to claim 1, further comprising regions encoding proteins capable of conferring upon transformed plant material at least one of the following agronomically desirable traits:
resistance to insects, fungi, viruses, bacteria, nematodes, stress, dessication, and herbicides.

7. The polynucleotide according to claim 6, wherein the herbicide is other than glyphosate.

8. The polynucleotide according to claim 7, wherein the herbicide is a protoporphyrinogen oxidase (PPGO) inhibitor and the corresponding resistance protein is a PPGO or inhibitor resistant variant thereof.

9. A recombinant vector comprising the polynucleotide of claim 1.

10. Plant material which has been transformed with the polynucleotide of claim 1.

11. The plant material of claim 10, which has been, or is, further transformed with a polynucleotide comprising regions encoding proteins capable of conferring upon plant material containing it at least one of the following agronomically desirable traits: resistance to insects, fungi, viruses, bacteria, nematodes, stress, desiccation, and herbicides.

12. A transgenic plant regenerated from the plant material according to claim 10.

13. A progeny of the transgenic plant of claim 12, wherein said progeny comprises the polynucleotide.

14. A method of selectively controlling weeds in a field, the field comprising weeds and transgenic plants comprising the polynucleotide according to claim 1, the method comprising application to the field of a glyphosate type herbicide in an amount sufficient to control the weeds without substantially affecting the plants.

15. The method according to claim 14, further comprising application to the field either before or after application of the glyphosate herbicide of one or more of the following: a herbicide, insecticide, fungicide, nematicide, bacteriocide and an anti-viral.

16. Transgenic seed from the transgenic plant of claim 12, wherein said seed comprise the polynucleotide.

17. The polynucleotide according to claim 2, further comprising a sequence which encodes a chloroplast transit peptide/phosphoenolpyruvate synthase (CTP/PPS) or a chloroplast transit peptide/pyruvate orthophosphate di-kinase (CTP/PPDK), which sequence is under expression control of a plant operable promoter.

18. The polynucleotide according to claim 17, wherein the CTP and PPDK encoding sequences are non-heterologous with respect to each other.

19. The polynucleotide according to claim 2, comprising at least two of said transcriptional enhancers which are tandemly present in the polynucleotide.

20. The polynucleotide according to claim 2, further comprising regions encoding proteins capable of conferring upon plant material containing it at least one of the following agronomically desirable traits: resistance to insects, fungi, viruses, bacteria, nematodes, stress, dessication, and herbicides.

21. The polynucleotide according to claim 20, wherein the herbicide is other than glyphosate.

22. The polynucleotide according to claim 21, wherein the herbicide is a protoporphyrinogen oxidase (PPGO) inhibitor, and the corresponding resistance protein is a PPGO or inhibitor resistant variant thereof.

23. A recombinant vector comprising the polynucleotide of claim 2.

24. Plant material which has been transformed with the polynucleotide of claim 2.

25. The plant material of claim 24, which has been, or is, further transformed with a polynucleotide comprising regions encoding proteins capable of conferring upon plant material containing it at least one of the following agronomically desirable traits: resistance to insects, fungi, viruses, bacteria, nematodes, stress, desiccation, and herbicides.

26. A transgenic plant regenerated from the plant material according to claim 24.

27. Transgenic seed from the transgenic plant of claim 26, wherein said seed comprises the polynucleotide.

28. A method of selectively controlling weeds in a field, the field comprising weeds and transgenic plants comprising the polynucleotide of claim 2, the method comprising application to the field of a glyphosate type herbicide in an amount sufficient to control the weeds without substantially affecting the plants.

29. The method according to claim 28, further comprising application to the field either before or after application of the glyphosate herbicide of one or more of the following: a herbicide, insecticide, fungicide, nematicide, bacteriocide and an anti-viral.

* * * * *

SEQUENCE LISTING

<160> NUMBER OF SEQ ID NOS: 70

<210> SEQ ID NO 1
<211> LENGTH: 3836
<212> TYPE: DNA
<213> ORGANISM: Brassica napus

<400> SEQUENCE: 1

```
gcatgcagat cttaaaggct cttttccagt ctcacctacc aaaactataa gaaaatccac      60
ttgctgtctg aaatagccga cgtggataaa gtacttaaga cgtggcacat tattattgac     120
tactagaaaa aaaactcata caccatcgta ggagttgggg ttggtgaaga atttgatggg     180
tgcctctccc cccccactc accaaactca tgttctttgt aaagccgtca ctacaacaac      240
aaaggagacg acagttctat agaaaagctt tcaaattcaa tcaatggcgc aatctagcag     300
aatctgccat ggcgtgcaga acccatgtgt tatcatctcc aatctctcca aatccaacca     360
aaacaaatca cctttctccg tctccttgaa gacgcatcag cctcgagctt cttcgtgggg     420
```

-continued

```
attgaagaag agtggaacga tgctaaacgg ttctgtaatt cgcccggtta aggtaacagc     480
ttctgtttcc acgtccgaga aagcttcaga gattgtgctt caaccaatca gagaaatctc     540
gggtctcatt aagctacccg gatccaaatc tctctccaat cggatcctcc ttcttgccgc     600
tctatctgag gtacatatac ttgcttagtg ttaggccttt gctgtgagat tttgggaact     660
atagacaatt tagtaagaat ttatatataa ttttttttaaa aaaaatcaga agcctatata     720
tatttaaatt tttccaaaat ttttggaggt tataggctta tgttacacca ttctagtctg     780
catctttcgg tttgagactg aagaatttta ttttttaaaa aattattata gggaactact     840
gtagtggaca acttgttgaa cagtgatgac atcaactaca tgcttgatgc gttgaagaag     900
ctggggctta acgtggaacg tgacagtgta acaaccgtg cggttgttga aggatgcggt      960
ggaatattcc cagcttcctt agattccaag agtgatattg agttgtacct tgggaatgca    1020
ggaacagcca tgcgtccact caccgctgca gttacagctg caggtggcaa cgcgaggtaa    1080
ggttaacgag ttttttgtta ttgtcaagaa attgatcttg tgtttgatgc ttttagtttg    1140
gtttgttttc tagttatgta cttgatgggg tgcctagaat gagggaaaga cctataggag    1200
atttggttgt tggtcttaag cagcttggtg ctgatgttga gtgtactctt ggcactaact    1260
gtcctcctgt tcgtgtcaat gctaatggtg gccttcccgg tggaaaggtg atcttcacat    1320
ttactctatg aattgtttgc agcagtcttt gttcatcaca gcctttgctt cacattattt    1380
catcttttag tttgttgtta tattacttga tggatcttta aaaggaatt gggtctggtg     1440 tgaaagtgat tagcaatctt tctcgattcc ttgcagggcc gtgggcatta ctaagtgaaa    1500
cattagccta ttaacccca aaattttga aaaaaattta gtatatggcc ccaaaatagt      1560
ttttaaaaaa ttagaaaaac ttttaataaa tcgtctacag tcccaaaaat cttagagccg    1620
gccctgcttg tatggtttct cgattgatat attagactat gttttgaatt ttcaggtgaa    1680
gctttctgga tcgatcagta gtcagtactt gactgccctc ctcatggcag ctcctttagc    1740
tcttggagac gtggagattg agatcattga taaactgata tctgttccat atgttgaaat    1800
gacattgaag ttgatggagc gttttggtgt tagtgccgag catagtgata gctgggatcg    1860
tttctttgtc aagggcggtc agaaatacaa gtaatgagtt cttttaagtt gagagttaga    1920
ttgaagaatg aatgactgat taaccaaatg gcaaaactga ttcaggtcgc ctggtaatgc    1980
ttatgtagaa ggtgatgctt ctagtgctag ctacttcttg gctggtgctg ccattactgg    2040
tgaaactgtt actgtcgaag gttgtggaac aactagcctc caggtagttt atccactctg    2100
aatcatcaaa tattatactc cctccgtttt atgttaagtg tcattagctt ttaaattttg    2160
tttcattaaa agtgtcattt tacattttca atgcatatat taaataaatt ttccagtttt    2220
tactaattca ttaattagca aaatcaaaca aaaattatat taaataatgt aaaattcgta    2280
atttgtgtgc aaataccttta aaccttatga acggaaacc ttatgaaaca gagggagtac    2340 taatttttata ataaaatttg attagttcaa agttgtgtat aacatgtttt gtaagaatct   2400
aagctcattc tcttttattt ttttgtgatg aatcccaaag ggagatgtga aattcgcaga    2460
ggttcttgag aaaatgggat gtaaagtgtc atggacagag aacagtgtga ctgtgactgg    2520
accatcaaga gatgctttg gaatgaggca cttgcgtgct gttgatgtca acatgaacaa     2580
aatgcctgat gtagccatga ctctagccgt tgttgctctc tttgccgatg gtccaaccac    2640
catcagagat ggtaaagcaa aaccctctct ttgaatcagc gtgttttaaa agattcatgg    2700
ttgcttaaac tctatttggt caatgtagtg gctagctgga gagttaagga gacagagagg    2760
```

```
atgattgcca tttgcacaga gcttagaaag gtaagtttcc tttctctca tgctctctca      2820 ttcgaagtta atcgttgcat aacttttgc ggtttttttt tttgcgttca gcttggagct      2880
acagtggaag aaggttcaga ttattgtgtg ataactccac cagcaaaggt gaaaccggcg      2940
gagattgata cgtatgatga tcatagaatg gcgatggcgt tctcgcttgc agcttgtgct      3000
gatgttccag tcaccatcaa ggatcctggc tgcaccagga agactttccc tgactacttc      3060
caagtccttg aaagtatcac aaagcattaa aagacccttt cctctgatcc aaatgtgaga      3120
atctgttgct ttctctttgt tgccactgta acatttatta gaagaacaaa gtgtgtgtgt      3180
taagagtgtg tttgcttgta atgaactgag tgagatgcaa tcgttgaatc agttttgggc      3240
cttaataaag ggttaggaa gctgcagcga gatgattgtt tttggtcgat catctttgaa       3300
aatgtgtttg tttgagtaat ttttctaggg ttgagttgat tacactaaga aacacttttt      3360
gattttctat tacacctata gacacttctt acatgtgaca cactttgttg ttggcaagca      3420
acagattgtg gacaattttg cctttaatgg aaaggacaca gttgtggatg ggtgatttgt      3480
ggacgattca tgtgtggtta ggtgatttgt ggacggatga tgtgtagatg agtgatgagt      3540
aatgtgtgaa tatgtgatgt taatgtgttt atagtagata agtggacaaa ctctctgttt      3600
tgattccata aaactataca acaatacgtg gacatggact catgttacta aaattatacc      3660
gtaaaacgtg gacacggact ctgtatctcc aatacaaaca cttggcttct tcagctcaat      3720
tgataaatta tctgcagtta aacttcaatc aagatgagaa agagatgata ttgtgaatat      3780
garscggaga gagaaatcga agaagcgttt acctttgtc ggagagtaat gaattc           3836
```

```
<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
gcatgcagat cttaaaggct cttttccagt c                                    31

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gaattcatta ctctccgaca aaaggtaaac gc                                   32

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gcgcaatcta gcagaatctg                                                 20

<210> SEQ ID NO 5
<211> LENGTH: 20
<212> TYPE: DNA
<213> ORGANISM: Artificial Sequence
<220> FEATURE:
<223> OTHER INFORMATION: Primer
```

```
<400> SEQUENCE: 5
tccttcttgc cgctctatct                                           20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcgttgaaga agctggggct                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
acctatagga gatttggttg                                           20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
actaagtgaa acattagcct                                           20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gttccatatg ttgaaatgac                                           20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tccactctga atcatcaaat                                           20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtaagaatct aagctcattc                                           20

<210> SEQ ID NO 12
```

```
<211> LENGTH: 20
<212> TYPE: DNA
<213> ORGANISM: Artificial Sequence
<220> FEATURE:
<223> OTHER INFORMATION: Primer

<400> SEQUENCE: 12
tcatggttgc ttaaactcta                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cagcttgtgc tgatgttcca                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cgatcatctt tgaaaatgtg                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ctctctgttt tgattccata                                               20

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cgcatcagcc tcgagcttct tcgtg                                         25

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ggtgagtgaa cgcatggcta ttcctgcat                                     29

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
```

```
atgcaggaat agccatgcgt tcactcacc                                              29

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
catttcaaca tatggaacag atatc                                                  25

<210> SEQ ID NO 20
<211> LENGTH: 90
<212> TYPE: DNA
<213> ORGANISM: Artificial Sequence
<220> FEATURE:
<223> OTHER INFORMATION: Primer

<400> SEQUENCE: 20
cccgggatat tggaagttaa aggaaaagag agaaagagaa atctttctgt ctaagtgtaa            60
ttaaccatgg cgcaatctag cagaatctgc                                             90

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ggacgtggaa acagaagctg                                                        20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tctcaaaccg aaagatgcag                                                        20

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
ggttgaagca caatctctga agcttccatg g                                           31

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
gatcttgggt cattttaatg ggccttctaa c                                           31

<210> SEQ ID NO 25
```

```
<211> LENGTH: 34
<212> TYPE: DNA
<213> ORGANISM: Artificial Sequence
<220> FEATURE:
<223> OTHER INFORMATION: Primer

<400> SEQUENCE: 25
aaataaaccc attaaccact aatgaaaaag ggat                              34

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
gcggagctcg agacttttca acaaaggg                                     28

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
atcccgggaa gcatgcgaag gatagtggga ttgtg                             35

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
cgcccgggat tgaatttbaa agc                                          23

<210> SEQ ID NO 29
<211> LENGTH: 209
<212> TYPE: DNA
<213> ORGANISM: Figwort Mosaic Virus
<220> FEATURE:
<223> OTHER INFORMATION: Enhancer

<400> SEQUENCE: 29
tctagagcag ctggcttgtg gggaccagac aaaaaaggaa tggtgcagaa ttgttaggcg   60
cacctaccaa aagcatcttt gcctttattg caaagataaa gcagattcct ctagtacaag  120
tggggaacaa aataacgtgg aaaagagctg tcctgacagc ccactcacta atgcgtatga  180
cgaacgcagt gacgaccaca aaagagctc                                   209

<210> SEQ ID NO 30
<211> LENGTH: 309
<212> TYPE: DNA
<213> ORGANISM: Cauliflower Mosaic Virus
<220> FEATURE:
<223> OTHER INFORMATION: Enhancer

<400> SEQUENCE: 30
tgagactttt caacaaaggg taatatccgg aaacctcctc ggattccatt gcccagctat   60
ctgtcacttt attgtgaaga tagtggaaaa ggaaggtggc tcctacaaat gccatcattg  120
cgataaagga aaggccatcg ttgaagatgc ctctgccgac agtggtccca aagatggacc  180
```

```
cccacccacg aggagcatcg tggaaaaaga agacgttcca accacgtctt caaagcaagt    240
ggattgatgt gatatctcca ctgacgtaag ggatgacgca caatcccact atccttcgca    300
agacccttc                                                            309

<210> SEQ ID NO 31
<211> LENGTH: 15941
<212> TYPE: DNA
<213> ORGANISM: Glycine max

<400> SEQUENCE: 31
aaaaaatacc ttttagtaaa ataagagcgt ragatcaatc agacgttttc tctttgggac     60
ttctcattct taattgaatt gacaataact aaagtgaaac taaggctaaa atcaactcgc    120
ctagtcaagc tcgtccacaa aaataggttt ttgaaagttt accatgtcag tttcttacta    180
agtaaaaaag gatcatttgt aaggtccaac gccttaaaat gatcacccct caaagtaaaa    240
gaatcacttg tttcacgcat aagtaagaac tacgtaggtc tgatttcctc tccaaaggag    300
ggtacgtagg agcaaaagcc cgcttttgt cgaccttaaa aaataaaaag aaacaaaagt    360
taaggtaaca caatttccac aattctagaa ataaggttgt tgtctttcga gacaaacgta    420
agaggtgcta ataccttcct caaacgtaaa tacaactccc gaacttagaa ttttcatttt    480
gaccggtttc cttcggtttt cccgacgttt tccacaaata aacgttggtg gcgactccgc    540
gcatctttcc tcctttggaa agcgcaccca tgagcctcgc cctcgctcgc ccgcgaaggg    600
cacgttgcga cactaggtta ataagaagtt tagtccacat atctatggac ctcttaaggt    660
gattatcaaa gtggaagtgg tgacctacat gttggcccta ccagcttatt cgtatattta    720
cccccatcaa ccatgtatct cagctgaaac atgctatcaa tccaaatgtt atcagaggaa    780
catgagctgc atgttcaacc agaagtagtt ctagtcttaa tacaaatgtc aaatggcaca    840
agtgagattt tgaatttctg atgttgtaaa atctcaggta catgaatact attgggaagc    900
aattattcat acttcaccaa tccaaactga cccaaaattc tcaaatcaca tgaaagcaaa    960
aatgcatata acacgaagaa taagaagaag aggaactaac ctggggtttc gatgattaaa   1020
gcgttgttgt tgatgatgaa aacgatgatt atggagagaa attgttgttg aatggtgaaa   1080
ttgttataga aagagaacga agatagagaa aaagatatat agatttttca aggctcaaac   1140
cctaaaatca ccatgagaga gaacaaagat tgagaaacct acaaccacta tgagagagaa   1200
tgagcagaac agaagcgtga gatagagaac gagagttaag gtgcgagagg acacgaagaa   1260
caaaaggtgt gagagaaaga acaaaggagc ctacggtgtg agatgagaga atttgaaatt   1320
cttaccattt aggtggaatt tcaattctac aattttattc tattaaaatt attttaaaaa   1380
atgatgtcat tttaaattct ttaaaatctc atatccaaca actgaattat gatagaggta   1440
tttcaaattc acttaaaaaa attatcttat ttaaatacco catccaaaca tagcgaaatg   1500
ttcatgagaa ggatcaagtg gtttggaaac atagtactaa tggtgtttat acagttcatg   1560
gaatccttga tagataattt aaaggttgct ggaaattgga tgaaggtgtg gagattaaat   1620
attcttccaa aaataaagcg ttttatttgg agagtgttgt gtggttgtct cccctgtagg   1680
caaaagcttc gatgtaaagg agttcaatgt ccaataacct atgctttcta tccctcgatt   1740
attgaaaatg aatgacacat tttatttggt tgaaatcaag aaataagcat gtggcaagca   1800
acgggtattt gacaattcat agaacaaaag gtgaatgcag caaaagaatt aatgaactcc   1860
ttttcgatct acttggatca ctacatggag atattatcaa caaatttgat gttactttat   1920
```

-continued

```
ggagcagttg gaattcttgg aatgacaaga tatgaaatga acataccaac cctcctcttg   1980
tttctgtttc ggtttctatg cagtattttg ttgaatggca aagtgcaagg taatatgctc   2040
ctcaacatca attaacaaat gttcatgaca tctcttacca gctccaactt ggggacgttt   2100
gacaaacacc accgtcaagt ttccttaaat gcaacattaa tgttgctcat ttcaaggagg   2160
agaatagttt tggtgtcggc atgatactcc atcaaggaag attcgtcaaa gctcactcac   2220
gttttcgaca tgggtcgaca tgggttacct gacccaaagg ctgaggctta ggcttgggtt   2280
tgcttcaagt attgatctgg gcccagacta ttggtttaca taatatcatt tttgaaaacc   2340
taacatctaa aactcaaggt tgtttagagg tgcgccattc caaataaga ttatcctatt    2400 tgtgcatgaa tgcgaccaac tatctcctgt ttcagcatta taagtataa acaacaaact    2460 tctttaatca agggactaaa agatattgga catacaagct aaaagtgata gaatttgaga   2520
aaacaaatat tgacaacaat attcaagagg acactaaaac ataattctca aattttttt    2580 gtttatttaa aataaagtgg ttcattaggt agctcttgaa aaaaaaagt gattaacatg    2640 ctagtacatg ttaaaaaaag tgaataatat tctattataa gtaaagagga ataatttatc   2700
gatgtctcat ttttgagata gttcaccgaa gccaattttt ttactttttt ctcttcaatc   2760
aattttattt tgttaatagt tgtcattgtg gatggattat ataattttg aaatgattta    2820 aaatgagata tatattaata aatttaatta attcataaat atgttactaa atataaattt   2880
catggtatac tcaggacggt tataacggaa atcaaataaa taataaaata gaataatatt   2940
aatttgcagt aaaaagaata atattaattt attctgttta cactatgtat aacgaaatta   3000
aatatattca tttaatatga ttttattttt ctttaattta aaaacatgaa ttatttgttt   3060
cttattttat taccattttg ttcacttctc aattaataaa ataaaatat attctacaat    3120 tatagtaaaa aggtttaatt ttatataatg ttagcataca gattttctc tattaactaa    3180 ttaattaaaa attatcctta ttttaaggaa attaaaaatt atcatatata tataagtttt   3240
aaattaatta tcttatatat gtaccaaaaa gttttaaagc aattattata aaaattaata   3300
aatttatcat ataaaataat ttataattaa attttaaatt atcaattcat taaattaaat   3360
tatttaaaat ttttgaatga taatataata atttatcct ctactaagtc ccaacgtttc    3420
ctattttatt ccacttttag caataaattt tgtcataaac acttataaca aaaaagtaa    3480 gtaaaaaata aaaaaaagtt tttcaataaa gtataaacta atttgtataa acttttagaa   3540
aaaataaagt tatacattga taatataaat tttttacata attatccgat caactcatta   3600
tatatgataa atttattgat tttttaaaat aattatctta aaataattta aacaatgatt   3660
tgcaattaga tgataatata aaattatttt acacactaca tgtattaaac tcaaactttt   3720
atatattagt ttttctaaaa actaattttt aactcaaaaa aaatgttact tataattttc   3780
ttatcttctt tttttataag tatttttaa gaaatttatt gaaacatgac catgcttggg    3840
tcaataatac tactctctta gacaccaaac aacccttccc aaactataat ctaatccaaa   3900
agccatcatt cattttcctt ggtaggtaaa gttccaagac cttcaccaac ttttcactc    3960 aattgttttg gtgtaagcaa ttcgacatgt gttagtgtta gttggcaacc aaaaatccct   4020
ttatgtgact caatccaaca accactcaca ccaccaaccc ccataaccat ttctcacaat   4080
acccttcatt tacacattat catcaccaaa aataaataaa aaaacctct catttcgag    4140 agagagagag agacttcaca gaccaaagtg cagagaacaa caaagttcac aactttaagg   4200
aaaattgaaa tgcccaagt gagcagagtg cacaatcttg ctcaaagcac tcaaatttt     4260 ggccattctt ccaactccaa caaactcaaa tcggtgaatt cggtttcatt gaggccacgc   4320
```

```
ctttgggggg cctcaaaatc tcgcatcccg atgcataaaa atggaagctt tatgggaaat    4380
tttaatgtgg ggaagggaaa ttccggcgtg tttaaggttt ctgcatcggt cgccgccgca    4440
gagaagccgt caacgtcgcc ggagatcgtg ttggaaccca tcaaagactt ctcgggtacc    4500
atcacattgc cagggtccaa gtctctgtcc aatcgaattt tgcttcttgc tgctctctct    4560
gaggtgaagt ttatttattt atttatttgt ttgtttgttg ttgggtgtgg gaataggagt    4620
ttgatgtgta gagtggattt tgaatatttg attttttttt gtattattct gtgaaaatga    4680
agcatcatgt cccatgaaag aaatggacac gaaattaagt ggcttatgat gtgaaatgag    4740
gatagaaatg tgtgtagggt ttttttaatgg gtagcaataa gcatattcaa tatctggatt    4800
gatttggacg tttctgtata aaggagtatg ctagcaatgt gttaatgtat ggcttgctaa    4860
aatactccta aaaatcaagt gggagtagta tacatatcta cagcaaatgt attaggtgag    4920
gcatttggct tctctattgt aaggaacaaa taatatcagt taatgtgaaa atcaatggtt    4980
gatattccaa tacattcatg atgtgttatt tatatgtacc taatattgac tgttgttttt    5040
ctccgcaatg accaagatta tttatttttat cctctaaagt gactaattga gttgcttact    5100
ttagagaagt tggacccatt aggtgagagc gtggggggaa ctaatcttga atatacaatc    5160
tgagtcttga ttatccaagt atggttgtat gaacaatgtt agctctagaa gataaaccct    5220
cccccaaaac acaaattaga atgacatttc aagttccatg tatgtcactt tcattctatt    5280 attttttacaa cttttagtta cttaacagat gtcttgttca gcataaatta taatttattc    5340
tgtttttttt tagggaacaa ctgttgtaga caacttgttg tatagtgagg atattcatta    5400
catgcttggt gcattaagga cccttggact gcgtgtggaa gatgacaaaa caaccaaaca    5460
agcaattgtt gaaggctgtg ggggattgtt tcccactagt aaggaatcta aagatgaaat    5520
caatttattc cttggaaatg ctggtactgc aatgcgtcct ttgacagcag ctgtggttgc    5580
tgcaggtgga aatgcaaggt ctgttttttt ttttttgttc agcataatct ttgaattgtt    5640
cctcgtataa ctaatcacaa cagagtacgt gttcttcttc ctgttataat ctaaaaatct    5700
catccagatt agtcatcctt tcttcttaaa aggaaccttt aattatcaat gtatttattt    5760
aatatttaaa ttagcttgtc aaagtctagc atatacatat tttgattata ttctgagaaa    5820
tgcacctgag ggtgttcctc atgatctact tcaacctctg ttattattag attttctatc    5880
atgattactg gtttgagtct ctaagtagac catcttgatg ttcaaaatat ttcagctacg    5940
tacttgatgg ggtgccccga atgagagaga ggccaattgg ggatttggtt gctggtctta    6000
agcaacttgg tgcagatgtt gattgctttc ttggcacaaa ctgtccacct gttcgtgtaa    6060
atgggaaggg aggacttcct ggcggaaagg tatggtttgg atttcattta gaataaggtg    6120
gagtaacttt cctggatcaa aattctaatt taagaagcct ccctgttttc ctctctttag    6180
aataagacta agggtaggtt taggagttgg gttttggaga gaaatggaag ggagagcaat    6240
ttttttcttc ttctaataaa tattctttaa tttgatacat tttttaagta aaagaatata    6300
aagatagatt agcataactt aatgtttttaa tcttttattt attttttataa atattatata    6360 cctgtctatt taaaaatcaa atatttgtcc tccattccct ttcccttcaa aacctcagtt    6420
ccaaatatac cgtagttgaa ttatattttg gaaggcctat tggttggaga cttttccttt    6480
tcagagatta tccctcacct ttattatagc ctttctattt ttaaacttca tatagacgcc    6540
attcttgttt taaaaacac taagttttct tttagttata ccttcccctc cttattctct    6600
ccaaagtaaa tattgtagca agtgttggtt gatccattgt gaatcttatt atcctatttta   6660
```

```
acatgcaggt gaaactgtct ggatcagtta gcagtcaata cttgactgct ttgcttatgg   6720
cagctccttt agctcttggt gatgtggaaa ttgagattgt tgataaactg atttctgttc   6780
catatgttga aatgactctg aagttgatgg agcgttttgg agtttctgtg aacacagtg    6840 gtaattggga taggttcttg gtccatggag gtcaaaagta caagtaggtt tctatgtttt   6900
agtgttacat cacttttagt atccaaaatg caatgaaatt aaaactcatg tttcctatta   6960
ggtctcctgg caatgctttt gttgaaggtg atgcttcaag tgccagttat ttactagctg   7020
gtgcagcaat tactggtggg actatcactg ttaatggctg tggcacaagc agtttacagg   7080
tattcatgaa tgacactatc ttctattatc ttttatttta tagcttacac tatcattcct   7140
aattcaaccc ccttctttc tctttcccct cactcccaaa atagagctta tcattgtatc    7200
cttaatagct cttttatgtg ctgtttcatc tcttgagcag attctacatg attatccttt   7260
ttagtgaact ttttgtctt taaataatt gatatcatca tttgaacttg cacatcatct     7320
ctatccttcc tcattttatt atatttcatt aagagtgata aaattacatt gtcaagtaaa   7380
gcaagttagc gtatcagata atgatgcttc gattgcagaa ttggtgaaag cttgcacaat   7440
tcattagctt agtgacaatt gtgatgtaga tagccataat cttccatgca acttattatg   7500 cttttttgtct aaaacttctt ttgcacttaa acatgaatta gagagttagg atgaacaata  7560
gtaacagaca caaagcttat ttctagacca cccagtggtg aagacgaagc agcatgagtg   7620
agattaatgg cagcatctga ttgaagcttc ttttggtatt attggagatg aaatcttgag   7680
ccaaattagg gcttttgcct cctcaatagc cattggttca aaattgctt caataaaatg    7740 attacagaat caaattctta agaaagacct tcaagaacaa catcaagatg tttcctgtgc   7800
aaaacaggct cacctacaaa agagtgtcta caagcacctt tacacttgca aaaaattcct   7860
taactgaaca attgccaaga gtcatgttgc aaacttgaga ttggagttga ttagatttgg   7920
tgtgtgtgag attctggaaa tgagcatgaa gttttttgca aagctcataa aatgaatgca   7980
gccaagaatc ctagatagga ttgaatttga gagagaggct tgaagtcaag ataaccgcaa   8040
ctgatcttgc tgttcccatg ctgcatagga ctcgttgatt ctaccaagat aacaatcttc   8100
tgtggtgaga atatgagtgg gaattgtcag gcaacaaaga aaatgaaggc tatgagcctt   8160
tgttaaggtg cagagagaaa acagaaaatg aagaacttgt gtattgaagg aattgaaaag   8220
ccaattacaa ttgtgttgca gagagatatt tatagttctg aagtgtataa ctaactaaac   8280
agaatgctac caacctagag gcagttgaga attgctccct tattacaata ctctcacagc   8340
cttgatgata ggcttgattt gctgccaccg aagaagaaca ttattgttgg agagtttttc   8400
agtgattgca tcagagaaag ttacaagtgt gattggagat gaaggacttg cggtcgtcga   8460
aggttaagtg ttaagtggtg gaatgtgtat cggaggtggt tgcctagccc aagaagctgg   8520
ttgcagtgga agcggatgcg gcagaagcca tgggttcaga tcagaactat gttctagata   8580
ccatattagg gttagctttc aagagaaaac ttatgaaact gaactgtaaa ctgttgtatt   8640
attgattagc tgatctagta gtgatggaag cttgcttgcg aagcttctat ggaggctgga   8700
tcattgagct tcaatgaggt ccttcaatgg tgatttttca ccatggagat gcagcggaag   8760
ataaatgaag aggtgagagg aggcgtcatc cactaggaaa taaactatgg aagaaggagc   8820
ttcaccacca agagagtgtc ttggataaga agcttagaga ggaagcttca atggaggaat   8880
agaaagagag aggggggaaca aaaaattgaa ggaggaaaag agggagagaa gttgaacttt   8940
gaagtgtgtc tcacaagact cattcattaa agttacaaca agtgttacac atgcttctat   9000
ttatagtcta ggtaacttcc ttgagaagct agaacttaac tacacacacc tctctaataa   9060
```

```
ctaagataac ctccttgaga aatttccttg agaagcttcc ttaagaagat tcctagagaa    9120
gctaaagctt agttacacac acctctctaa taactaagtt cacctccttg agatgagaag    9180
ctagagcctt agctacacac acccttataa tagctaaact cactctattc caaatacat     9240 gaaaatacaa aaaagttcct actacaaaga ttactcaaaa tgtcctgaaa tacaagacta    9300
aaactctata ctactagaat ggtcaaaata caaggtccaa agaaggaaa aacctattct     9360 aatatttaca aagagagtgg acccaacctt agtccatggg ctcagaaatc taccctgagg    9420
ttcatgggaa tcctagggtc ttctttagta gctctagtcc aattttcttg gagtcttcta    9480
tccaatatcc ttgggggtag gattgcatca tgtagtacaa gagagggaa tatatataca     9540 gttgtaagtt gtaactacct aatcaaaccc aactgactca ccatacacag aaaacaatg     9600 tacaaaggat aatagaaaaa ctgaaactga gatatactca ttacatagaa gaattacatg    9660
atgaatctga aaattttaat tgggaaactg aggacaataa caaggctttc agagttcatt    9720
ttgacaatag gtaaattatg gacttcaact tagacctcaa gggtatgctt gggagtgggg    9780 tttttagagga aaaggggaag gagggaaatt ttttaattct agtaaatatt ctctatttg    9840 attaattttt aaaataaaac aaataaactt atagattagc attcacttaa tgtcctgatc    9900 tttttatttgt ttcatgaagt ttttttatagc ctttctgttt ctgttaaaag aaattggagg   9960
gtgttcataa tctatatgcc catatatatg tattgtcctg ttgtctgtgt ttctgttttc   10020 tttcttttagt gtctcgcctt tccttaattc cttatcaaca ccttgtttat ttttgaaaac   10080
ttaaatgtcc tcatttttttt tacctgtact ataactttcc aaacaaatag tagaaaatgt  10140
ttcaaatatt ccccagaact gtttcagtga acaaagttca agccagaaaa aaagcaagca   10200
gaggctaaag aagtatatct tattgtgaag agtaatctca attggttaat tatcgaattg   10260 tatcattta caatagaaaa ttagaagtgg gttgattagt ttatacgaac aattatttaa    10320 ataggggttga tggtgtggtt aattactgat catatgttaa gactatgagt cgatgaccag   10380
cctcagtgca gtcatttta gttccattat ttttaattg tgcttatgtt taactttgtc     10440
cttcttttaa agggagatgt aaaatttgct gaagttcttg aaaagatggg agctaaggtt   10500
acatggtcag agaacagtgt cactgtttct ggaccaccac gagattttc tggtcgaaaa    10560 gtcttgcgag gcattgatgt caatatgaac aagatgccag atgttgccat gacacttgct   10620
gttgttgcac tatttgctaa tggtcccact gctataagag atggtatggt ttagctgttt  10680
gtttttgctc aagagcttgt tttcacatat tgtggtcaa gagcggttta gctgtttttt   10740
tttttaaatt gtggttaatg aaattattat aattatacta atattgaaat tggatcacta   10800
accatgtgaa atgcttgaat ttttagcttg aaaacttctt ttgtggatga tttttctttt   10860
atctatgtag tgtggggcat ctatgttgtt cctttaagct ttgtgtcata gttgtacaac   10920
ctggtctgtg ggctggtcca gttcttactc atgactgtct tttgcagcaa actggttaaa   10980
cttgggtgac ctgttgaccc acccagattg gcctgttctt ttttaaataa aactccaaaa   11040
ggctacttat aagatttcaa catgatactt gaatgaccac ccttacttta aaggtcatta   11100
tgccatcaga ccccttgatt ctctgttcag ttatgttctt attcttatta ttttttaatt   11160
tatattatta tccaacgatc tgatctttgt acatgatgct ggacaatcat caaagctagt   11220
ttggttacat catataatac cttttttttc ataaattatt ttttcccata atatatttat   11280
atgtattttt ttaatacaat attctgggga aattttttt ttctgttttc ttttttctgg    11340
tttgaatact atttcaatga ctgggcctta ttattttctg gttggggtta tacaactgtc    11400
```

```
ctttgatgta cttttgaatg cttcaatagt attttttcata atcatggaag gcactagagt   11460
gcagtgcata ttgcacaagg ttctttaatg gcatcttgaa tttgttagaa catggagtta   11520
tgatatacaa ccattcctat gtcttcatct aatagctaaa gcttttggcg tagttggtta   11580
acatggtatt ggaatcttat tttaaaggtc catcttattc gcaagtacaa ggcaggtgga   11640
cctgcgcatt attcacgtgc caggctcaaa gggattttgt atgaggggga attttttggaa  11700
tataatatat agaatcattc atgtggttca cctatcatgt gtcaactcaa gtttttgtcc   11760
tagttgtatt attgcagtgt ctaaactagg catgatcttc tgtggaagga aatttaacct   11820
aaggaacttg aatgcttctt gttctgagat cttttattttt tttctccaat cttttttaata 11880
cttgaaaggt tttagttgta tctataaagg gtgcagaatt aggggtcag cttttctgtt    11940
gtaagcgtga attaagtgca ttttatgttg ttccctattt tatacatttg aactatcaac   12000
catatcattt agcaaacttc tttgttgctc agattcccat ttattcttgt ttcctctatt   12060
ttttagtggc aagttggaga gttaaagaga ctgagaggat gatagcaatc tgcacagaac   12120
tcagaaaggt cttgctaatt cctttatggt ttctatatta ctggacttttt tacatctcac   12180
tgacctacta ctgtcttggt atttcagcta ggagcaacag ttgaagaagg tcctgattac   12240
tgtgtgatta ctccacctga gaaattgaat gtcacagcta tagacacata tgatgaccac   12300
agaatggcca tggcattctc tcttgctgct tgtggggatg ttccagtaac catcaaggat   12360
cctggttgca ccaggaagac atttcctgac tactttgaag tccttgagag gttaacaaag   12420
cactaagcat tttgtacatt gagtagggaa gagagagaga tatatataaa tactcacaaa   12480
gcagtgagta tatggcttgc ttttgtttct aaacattcct ttataaggac ttgagataat   12540
ttgtattgtt taaagagcc attggttctg ttgtatcaaa gtaatttaat tttcagtacc    12600
gacttggctc tactcatatg tggtggtgta cattgcatct ttgcatttga ttccatatct   12660
attgggatgg gaccatacat ttttttgttta ttatttaagt caaacatatc agataatatg  12720
tggtgaccag aaaagtgtct agcaatcaaa tgggtctgtg attgcatgtt tgagttcagg   12780
acatttatta atgagtgaca gaattttaaa aagctcgcca ataggagttg ccacatctga   12840
tcgagtcttc tgtaaacact aactgtaact tgagtttgat aatcagattc cccccgttgg   12900
taggtaaatat gtaaatttca ctatagattc ttactgagga tgatggtctt gacttcgaag  12960
tggtgagtgt aattctctaa tctaaacttt atatatatat aaaaaaagaa tgttaaaaac   13020
ttgagtgaca tacagcaaat agcaatgaaa gcatgaccat ggccttgggg ggccaaatgg   13080
ccatgtacca cttttccacc tacttgagag ccatggtcct gaatgaggtc cttttgtttc   13140
atttttttta caataaagaa agttcatatt cttggcaata gcaaggcaaa tcatttgtgg   13200
aagtcacatg aaattcacca taggcttcat tgttcaaatc ctttagtcac taaggcaggg   13260
cctatgtaag aattttgact actcttgtaa atgctgtgcg gtaaagacta cgggaaaata   13320
taaattattg catatctaga ggtgaggttc atttctccga tccatttctc caagtaataa   13380
aaatatatat aaattattaa tatggtatga tatggttatt tgtcctttaa atatgcgatt   13440
ataggttcaa tctttggtta atctatcaaa tgcatctcaa tattttgaga gaatagtttt   13500
tagctcttga ctgagagata ctttgagtta aaaaaatgta tttataaact attgtctatt   13560
gaattttat tttttttgta acaccacatg tgagtatttt actaaatcca tgttacaatg    13620
tactgaatgt tttacaatac agtctggttt gataataaaa tatgcacaaa gtccagctta   13680
tgtaactctt tcaattcatg gaaaatgatg atatgcgaat tgaaagaaag aaaaccataa   13740
tgtaagtgta tttttttttt ctttctcttc tttaatatta ctcaatatca gattgcacat   13800
```

```
gggaagggta ctggctcatg tgggatatta attttatcc cttacctaaa aagagagaaa    13860
gagaaaataa ctatttaaaa agagtaccac caccaccttt ttcgctttta agttttgttc    13920
tgttttcact actctttcat gcgttgtttg ttggcttccg atagtgacga atatgataat    13980
gattttacgt tgagaaaaaa aatgtgccat gtaaattcca gagattgaaa ttttagcttc    14040
aaattaatat ttatttatt atcttttcaa attggttgca tgtgaaagaa tttgaagttc    14100
ttcaacaagg aaataaacac ttcaatgctc aatccttaga gtcagtcact agatcccaaa    14160
agaatgtgat gtttacacac attagtatat atatatatat aaacacagct tatattatat    14220
taatgagtga tgcgcgagga cggtggtgac actacatggc caaaacaaga aatgtaattt    14280 aattttttt tctttaagta ttactctatc cttgaatatt agtcttaaat cttcaaagac    14340
cttgcgaacg aagcaatctt gtcctgatcc tgtgattgtt ctacactagt ccttacgtgt    14400
acctaagcac atgatacttt gctgccctaa cataaattgt accataagga ttcttgggga    14460
gatgcttttg ccttcatttt caagtttgtt tacactttca agtcgttttt tcaatgcatt    14520
ctctttcctt tctgggaccc cttgtcttta acacgcgcgc acacaaaaac tagtagacaa    14580
taattagtac tacttgggtt ccattaaatt gtaactacat atacatgtgt ttttttttc    14640 ttggatcaac tgcatataca tatgttttat gagtttcatt gaatttatat ttacacaaac    14700
agttattaaa acataatgta gagccttgtc attaacctga tgttaggatt ataatttcat    14760
gctttgattt tgattgtacg tttttttgttt ttattgtaaa gtgtttattt tattaaaatt    14820
tgtcttggag tgctgtgatc tttagggtgc accgttcaaa agagagacga caaggataat    14880
actaatacta gtagattcca cgcattcaac cctagttagt ttagctatga caaattaagc    14940
atggtaagaa aaggggagga gaaaagtaag aatgaaaaca taacaaaat tgtgattgaa    15000 cttttccatg acgtaatgaa aacattaatt ttaagataag cttcaactcc taagaagaga    15060
tatgtcaaag aaacttagga ttttttctct atttataacg gtaaattact catccttta    15120 aatgattaat ttgcgttgtt gaattcgttg taaagggaaa atcaagaagt ctcttcacgg    15180
gaaagttata tcaaagtatc atatactaga cttcatggct agcttttact ttgattataa    15240
gtaatgcatg caattaatgg gcaaataaat tatttgaaac caactaaagt acaaataatt    15300
ttcctccaaa acctctcaag ttcgcattga aattaaataa accaatgcat attaaggcgt    15360
aaatctaaac catgtttgtt tcatcttgta ttgtatatca tagtattaat aaggtacttt    15420
gaatttagtt gttattgacc gttaaattta ggggtgagtt gttttactat ctcttactca    15480
attgctttta ttcaacgcaa attctagtag gatttcagc ccaaattaaa agaagttta    15540 cggtttgatt ctctacaaac ttgaattgag atttctaatt tcagaaatca ataattgcgg    15600
tcttaattaa ctctataatc aaaccttta acccaatctt tttctcaatt ctctgaatta    15660
agacaatcaa aatttaaact cacacgaatc tcacacgcct tcccacggta gagaaatata    15720
gggagtccct taatagcaaa agcctcaaaa ttcagaaaat ctcatccatt gcatttgcac    15780
attcaacaaa ccacccatta ttatgttccc ttaataaatc tcacacttaa aaaccctcct    15840
cacccataat taacccaaaa ggaagtttcc tccacacaaa aaatatcctt aaacaaagag    15900
cctctataaa tctatttaa aaaaccccc aaatttaagg a    15941
```

<210> SEQ ID NO 32
<211> LENGTH: 15172
<212> TYPE: DNA
<213> ORGANISM: Glycine max

```
<400> SEQUENCE: 32
aaaagtctga atgaagtgaa gttgttgtgt taggggatg ctgaatttga tttttaattta      60
atttaaataa attacctgtg taaggatttt ttgtaccgcc ttttaatcac aaattgtcgt     120
gtatcgaaag tttgttgaat tttatagtaa ctatcttgga ggttatacct agtaggattt     180
ctgattagtt aaccatgtaa atttttttaa tgggtttgtg tttgttttaa ctgatgttgt     240
ttttgatatg tacgtggtaa gtgtgatgag tttgtgcata tcttgatcaa agactgaagt     300
gaagttgttg tgtttggggg gttgactctt ttaggaagag gatttgaggg aatttcgcca     360
atgggggagc agaactccgg gacaccctga gaattttgag actccgggaa ttgaagttac     420
aacaggtttg atatgagtta gagtttgtat aatagaatag taattctttt tattttttat     480
ttttattgtt tatttatcca ttattgctat ttttgtaggt cctcttggtc agggattgc      540
caatgctgtt ggtttggccc ttgcagagaa gcacttggct gcaagataca acaagcctga     600
caatgagatt gttgaccatt acacgtaaaa ataactaaat catacacaac ttgcaagact     660
ttagttgttg gtgttttgct aatggcgttt gttttatgca ggtatgctat tctgggtgat     720
ggttgtcaaa tggagggaat tgcaaatgaa gcatgctcac ttgctggcca ctggggactg     780
gggaagctga tagcatttta tgatgacaat catatttcta ttgatggtaa cacagagatt     840
gcgttcaccg agagtgttga tagtcgtttt gagggacttg ggtggcatgt tatttgggta     900
aagaatggaa ataatggcta tgatgatatt cgtgctgcca ttaaggaagc aaaagctgtc     960
aaagacaaac ccacattaat caaggttagt ttactaattg tggcaatgat atgcatagat    1020
ttctggcttg tagttaccat aacaatcata atctgtcatg atttataggg attcttttaa    1080
actaaggtta taaacatgat atgttactaa agactgcatt gcattgtagt acctcatttg    1140
agaaactgga agttataggt gggaaatcaa aatagtaaat tatgggtcag tttattaagt    1200
gtagctggtt tgtcttttgc taactctatc atttcacagg tcacaacaac cattggttat    1260
ggttctccta acaaggctaa ctcctacagt gtgcatggaa gtgcactggg tgccaaagaa    1320
gttgatgcca ccaggcagaa ccttggatgg tcacatgagc cattccacgt gcctgaggat    1380
gtcaaaaagt atggatgatg ggtttagaga tttcttttttt cctgtgacac tgctgatgtt    1440
tataatgata ctgaataaga attgcttgtc tgtccccagg cattggagtc gccacacccc    1500
tgagggtgct gcacttgaag ctgagtggaa tgctaagttt gctgagtatg aaaagaaata    1560
caaggaggaa gctgcagaat tgaaatctat tatcaatggt gaattccctg ctggttggga    1620
gaaagcactt ccggtgagta aattctaaac tcacaggttt ttcttacatg tttgtaactt    1680
ttcaaggttt ggattacata ctatccaaag ttgatcatga tttcagtttg atttggtagt    1740
atggggcttc aaaaagttat tccaaatatt aaaacctggc ttccaatttg atttcagaca    1800
tacactccag agagcccagc ggatgccacc agaaacctgt ctcaaacaaa ccttaatgcc    1860
cttgcaaagg ttcttcccgg tctgcttggt ggcagtgcag atcttgcttc ttccaacatg    1920
accttgctca aaatgttcgg ggacttccaa aaggatactc cagcagagcg taatgttaga    1980
ttcggtgtta gagaacacgg aatgggagct atctgcaacg gcattgctct tcacagccct    2040
ggactgattc catattgtgc aaccttcttt gtattcactg actacatgag aggtgccata    2100
aggctttctg cgctgtctga ggctggggtt atttatgtca tgacccatga ttcaatagga    2160
cttggagaag atgggccaac ccaccagcct attgagcacc tagcaagctt ccgggcaatg    2220
ccaaacattt tgatgcttcg tcctgccgac ggtaacsgaa acagccgag catacaaagt    2280
ggccgtgctc aacaggaaag agaccctcca ttcttgccct atccaggcaa aaactgcccc    2340
```

-continued

```
agcttcccgg aactthcatt gaaggagttg aaaagggtgg ttacaccatt tcgggacaac    2400
tccactggca acaagcctga tgtcattttg atcggaactg gttcggaatt ggaaatcgct    2460
gccaaagctg ctgatgacct aaggaaggaa gggaaggctg ttagagttgt ttcccttgtt    2520
tcttggggaa cttttttgatg agcaatcaga agcstacaag gagagtgttt tccctgctgc    2580
tgtttcagcc agagttagca ttgaggcagg atcaacattt gggtgggaga aaattgttgg    2640
agcaaaggga aaagcaatag gcattgatcg ttttggagct agtgctccag ctggaagaat    2700
atacaaagaa tttggtatca ctaaggaagc tgttgttgct gcagctaaag agcttatcta    2760
gaacttttga ttttttttttg ccttctggtt ttggttgaga gcattccatg tcatgaataa    2820
gaaaaaggtt aaatatcctt cgattgggaa tttgggattc taagtgaaga agcaacatag    2880
atcaaagaat tttgtgaact tgtaataact atttgacaat ttagttttgc actgccacat    2940
ggttaaattc aatgtttgat catatcaacc atagatgcta gtttatacta cttgtataat    3000
ttgtttcact tgcagattca ctcttagcat ttgagtgttt ggatggccgt gttttgttca    3060
ttaagaaatg ttgacatgga tagtttgttg catggtaaat tggtgattaa tacctttttta   3120 agcttctttt ggcaagttgt taaaaagtgt tttgttttaa tctctagtta atctaaaaat    3180
gcctacttat tttatttga cttctcaaaac ttgtctatat gccgagtata aaaaaaactt    3240
gtctatataa gttccttatg gaaaaaggac ctacaaaata atttaaaaat gctgaatttg    3300
ttaggaagtt tgacaacttt agacattaat aattgttttt ttttcatata tataattgac    3360
tttcaaaact tgtctatata ttataaattc gttatggaaa gggcgaccac acgtaaaacg    3420
taacatgcca atctctcct agtgaactgt tattctcatt cagttttttgt aagttcacct    3480 tcaaattttc aatttttttt ttgacaaaaa tatctttgat ggaacacgtt aggggtgtaa    3540
attcaccatt catcatttca ttcattatac acaatagtct ttcataatcc aatgaaaact    3600
tgtttttgtt gttatttttt tctgaaaaat ctttataaaa taaataaaaa catttttttg    3660
ttataaattt cagttgaaat acataaccat taattctaca gagtgttaat gttgatgtaa    3720
aataaaaaaa tattggatat caaacttaat gaacagaaca aaaattacaa aattgtacaa    3780
tttaaatgat aaaaaaccaa attcacaaaa ataaaaatta aggacgaaat ttgagaaatg    3840
ataattaaaa acgattaaaa atataattaa actaaaattt attatgtaat tctttaatat    3900
atatatatat atatatatat atatatatat atatatatat ataataaaag ttttacatta    3960
taattttgaa atgaagtatt tgataaacga acaacccacc cttggggttg gtgagagtga    4020
aacggagaac agtgtctccc tcacttggtc ttctgagtcg agtcctattc atcaccaacc    4080
cactcgtcaa aattgttgta tgctatgtaa ccatttttgtt ttttaataaa taaaagtgtt    4140
ttgttctgct atgcactccc catcaaatac catttacttt tttttttgtct tctatcaatt    4200 tctatttagt tcctagttgc tacaacttcc agctggtgaa aaatagtcaa cagagactac    4260
aatattctaa taaatagaa taacaaaatc aaatatattc atttaatatg atttttatttt    4320 tatttaattt aaaacatgaa ttatttgttt cttatttaat taccgtttcg ttcacttctc    4380
aattaataaa ataaaaaatt tctacaatta tagaaaaagt ttagttttgt agattgttaa    4440
cataaagatt tttcctatta actaattaat taaaagtcat cttatatata agttttaaag    4500
taattatctt atatatgtac ccaaaagttt taaagcaatt attataaaaa agtaaaattt    4560
tatcatatac aataatctat aattcactga aagtataatt tttaaattat taatacgtta    4620
aaattatttt tttaaaattt gaatgatcat atagtaattt tattttatac caagtcccaa    4680
```

```
catttcctat tttattccac ttttaccaat aaatttcctc ataaacactt ataagaaaaa    4740
aagtaagtaa agaataaaat aagcttttct ataaactata aacaaatttg tataaacttt    4800
cttatattag tttttctgaa aactaatttt aaattataca taaattgaat ttactgataa    4860
ttttttattt tctttttgta taagtgtttt ttaagaaatt tgttcaaaca tatttttatg    4920
acatgtcaat gcttgagaga tataaggtga gttaaatcat aaatgattaa agaaaaataa    4980
aagaagaaaa agataattaa tttaattttt tattaacatt ctaacaaatt aacattatat    5040
aaataaaaat aatatttcaa taattggatc aataatacta ttgttcttaa acaccaaacc    5100
aaccttccta aagtcctaat ctaatccaaa agccatcatt catttccttt ggtaggtaaa    5160
gttccaaaac ctttaccaac cttttcactc aattattttg gtgtaagcaa ttcgacatgt    5220
gttagtgtta gttggcaacc aaaaacccct ttatgtgact cactcaatcc aacaacctct    5280
cacaccacca acccccccat aactcataag gccaaaacca tttctcacaa aacccttcat    5340
tacacacatt attatcatta tcacacacac aaaaaacctc tcatttcaaa gagagagaga    5400
gatttcacag accaaattgc agaggacgac aaagttcaca acttcaagga aaatcgaaat    5460
ggcccaagtg agcagagtgc acaatcttgc tcaaagcact caaattttyg gycattcttc    5520
caayyccaac aaacycaaat cggygaattc ggtttcattg aggccacgcc tttggggksc    5580
ctcaaaatct cgcatcyygr tgmayaaaam tggaagcytt atgggaaatt ttaatgyggg    5640
gaagggaaat tccggcrtgt ttaaggtttc tgcatcsgtc gccgccgccg cagagaagcc    5700
gtcaacgtcg ccggagatcg tgttggaacc catcaaagac ttctcgggta ccatcacatt    5760
gccagggtcy aagtctctgt ccaatcgaat tttgcttctt gctgctctct ctgaggtaaa    5820
gtttatttat ttatttattt ctgtatccaa aaatgtaaat tgttagtttg ttaattttg    5880 ttagcagtga gagtcgaact acttggcttc tttcttagtc atccaaccaa ccttatatct    5940
ccaaaattta tttattggtt ttttttgggg ttatgtggtt aggaatagga gtttgatgcg    6000
tggagtggat tttgaatatt tgattttttt tttttttgta ttattcagtg aaaatgaagc    6060
atcttgtccc atgaaagaaa tggacacgaa attaagtggc gtatgattta gaatgatgat    6120
agaaatgtgt ataggtggtt ttaatgtgta gcaataagca tattcaatat ctggattgat    6180
ttggacgttt ctgtataaag gagtatgcta gcaatgtgtt aataatgtct tgttaaaagt    6240
atggatggct aaaataatca taaaaatcga gtgggagtag tatacatatc tacaggaaat    6300
gtattaggtg aggcatttgg cttctctatt gcgagtaagg aacaagtaat ctcagttaat    6360
gtgaaaatca atggttgata ttccaataca ttcatgatgt gttatttacg ggaacgcaat    6420
attgactgtt gattttatct gcagctgaga ttatatacta tatccttcca aagaaatctt    6480
tgactcttga ttatccaagt atggttgtat taccaatttt agctctagaa gataatccct    6540
cccccaaaac acaaattaga atggtgctgc aagttccgtg ttactttcat tctattattt    6600
ttataacttt taattattta atagatgtct tgtttggcat aaactataat ttattctgtt    6660 ttttttatt cttatttagg gaacaactgt tgtagacaac ttgytgtaya gygaggatat    6720
tcattacatg cttggtgcat taaggaccct tggactgcgt gtggaagayg acmaaacaac    6780
caaacaagca attgtkgaag gctgtggggg attgtttccc actaktaarg aatctaaaga    6840
tgaaatcaat ttattccttg gaaatgctgg tactgcratg cgtcctttga cagcagctgt    6900
rgttgctgca ggtggaaatg caaggtctgt tttttgtttt gtttgttcat catgatctct    6960
gaattgttcc tcgtataact aatcacatca gactatgtgt tcttcctcca tcctgttata    7020
atctaaaaat ctcatccaga ttagtcatcc ttctttaaat gaacctttaa ttatatctat    7080
```

```
gtatttattt aacatgtaaa ttagcttgtc aagtcaaagt ctagcatata gatatactga   7140
ttacactctg aggaatgcac ctgagggtct taatcatgat ctatttcaac cttgccactt   7200
tcttctttta ttattagatc acctatcatg attactggtt tgagtctcta aatagaccat   7260
cttgatgttc aaaatatttc agctacgtac ttgatggrgt gccccgaatg agagagaggc   7320
caattgggga tttggttgct ggtcttaagc arctyggtgc agatgttgat tgctttcttg   7380
gcacaaactg tccacctgtt cgtgtaaatg ggaagggagg acttcctggc ggaaaggtat   7440
ggtttggatt tccattagaa taaggtggac taacttttcct ggagcaaaat tctaatttat   7500
accctgtttc cccctcttta gaataagaca ctaagggtat gtttaggagt tgggttttgg   7560
cgagaaaggg aagggaggc aattttttttt ctaataaata ttctttaatt tgataaattt   7620
tttaaacgaa ggaatatgaa gatagattag cataacttaa tgttttaatc ttttatttat   7680
ttttataaat attatatacc tctatttaaa aacaagatat ttttcctcca ttccctttcc   7740
ctttaaaacc tcagttccaa ataccgta cttgaattat attttggaag gtgtattggt   7800
tggagacctt tccttttcag aggttatccc tcacctttat tatagccttt ctactctctt   7860
aatgagttca ttgtgcattg agtcattgaa cttcctgtga aaagaaattg tttactttt c   7920 tttatttgtt acctacatcc ttattcctgt tttaaaaaat actaagtttt cttttagtta   7980
tgccttcccc tccttattct ctccaaagaa aatataatag cgaatgttgg tttatccatt   8040
gtgaatctta ttatcctatt tcacatgcag gtgaaactgt ctggatcagt tagcagtcaa   8100
tacytractg cttttgcttat ggcagctcct ttagctcttg gygatgtgga aattgagatt   8160
gttgataaac tgatttctgt tccatatgtt gaaatgactc tgaagttgat ggagcgtttt   8220
ggagtttctg tggaacacag tggtaattgg gatargttct tggtccatgg aggtcaaaag   8280
tacaagtagg tttctatgtt ttagcattac atcacttttt agtatccaaa atgcaatgaa   8340
atcaaaactc atgttttcta tcaggtctcc tggcaatgct tttgttgaag gtgatgcttc   8400
aagtgccagt tayttmctag ctggtgcagc arttactggt gggactatca ctgttaatgg   8460
ctgtggcaca agcagtttac aggtattcat gcttgacact attttctatt atctttatt   8520 ttatggtcta tactgtatca ttcctaattc aaccccttc ttttctcttt cccctcactt   8580 ccaaaaaat agagcttatc attgtattct taatagctct tgtatgtcct ttttcgtctc   8640
ttgagcagat tctaccgtga ttatcctttt tagtaaactt ttttttttgtg tgtctttaa   8700 ataattgata tcatcatatg aattcacaca tcatctctat cccttcctca ttttattata   8760
tttcattaac agtgataaag ataaaaataa attgtcaagt aaagcaagtt agcatgtcag   8820
ataatgatgc ttcaattgca aaattggtga agcttgcac agtacattag ctttggtgac   8880
aattgtgatg tagatagcca taacctccca tgcaacttat tatgttgttt gcttaaactt   8940
cttttgcact taaacacgga ttagagagag tgaggatgaa caataataac agacacaaag   9000
cttagtttta taccacccgg cacccagtgg tgaagaccaa gcagtatgag tgagatcaat   9060
ggcagcatct gattgaagct tcttgtggta tttttggaga tgaaatccga ggcgaattag   9120
ggcatctggc tcaacaatag ccattggttc aaacttgctt ttaataaaat tgattacaga   9180
atcaaattct tgaggaagcc ttcaagaact acatcatgat gttccctgtg caaaacaggt   9240
tcaccgacaa aagagaacat ctacaagttc ctttacacat gccaaaaatt cctcaactga   9300
acaattgcca agagtcatgt tgcgaacttc aggttggagt tgacgaaatt tggtgcatgt   9360
atgattctgg aaatgagcat gaagtttttt cctaagctca taaagtgaa tgcagccaag   9420
```

```
aaccctagat aggattgaat cggagagagg cttgaagcca agataacagc aactgatctt    9480
gctgttccca tgctgcgtag gactcattga ttctaccaag atcacaatct tctgtggtga    9540
gaaaatgagg gtgaattgtc aaccaataaa gaaaatggtg aaggctgagt cttgatgata    9600
ggcttgattt gcttgcgctg aagaagaacg ttattgttgt agagtttctc agtgattgta    9660
tgagagtaag ttacaggtgc gattggagat gacggacttg tggtgggagg agggtaagtg    9720
ttaagtggtg gaatgcgtat cagaggtggt tgcccagcca aagaagctgg ttgcggtgga    9780
ggaggtggtg gtgcagtgga agccatgggt tttgatgctt ttgagagaaa acatacgaaa    9840
ctgaactgta aacttttgta ttattgatta gctgatttgg tagtacaaga gaggaatata    9900
tatacagttt taatgtaact acctaaccaa acatgaggaa ctctccatac acagaaagac    9960
gtatacaaag gataacagac aaacagaaac ttagatatac tcatacagag aagaattaca   10020
ggatgaatct gagaatttta attgggaaac tgaggaaaat agcaagggtt tcagaattca   10080
ttttgacgat aggcaaatca tggacttaac ttagacctca agggtacgct gggagtgggg   10140
ggttttttaga gggaaaaggg aaggagggca aacttttaat tcctaataaa tattctcttt   10200
tttgattttt tttaaataa aacaaataaa cttatagatt agcatacact taatgtccta   10260
atcttttatt tatttgcatg agtttttttc ttttatattc tttctgtttc tgttttcttt   10320
cttcagtgtc tcttgtcttt ccttaattcc ttatcaatac cttgtttatt tttgaaaact   10380
taattttcct cattttttta acttataggc tatactatag tatgtataac tattcaaata   10440
aatagtagaa aatgtttcaa atattcccca gaactgtttc agtgaacaaa gttcaagcca   10500
gaaaaagaa gtatatcttc ttgtgaagag tagtctcaag tggttaattg tcaaattgta   10560
tcattttaga atacaaaatt agaagtggtt tgattagttt atacgaacga ttatttaaat   10620
agggttgatg atgtggttaa ttactgatca tatgtgaaga ctgtgagtcg atgaccagcc   10680
cagtgcagtc attttaaatt ccattatttt ttaatttgtg cttatgttaa actttgtcct   10740
tctttcaaag ggagatgtaa aatttgctga agttcttgaa aagatgggag ctaaggttac   10800
atggtcagag aacagtgtca cygttwctgg accrccacra gattyttctg gtcraaaagt   10860
cttgcraggc attgatgtca atatgaacaa gatgccagat gttgccatga cwcttgcygt   10920
tgtygcacta tttgctaatg gtcmmactrc yatmagagat ggtatggttt agctgttttgt  10980
ttgtgttcaa gagcttgttt taacaaattg tttttttttaa ttatggttaa tgaaattatt   11040
ataattacac taatattgaa attggatcac taaccatgtg aaatgcttga atttttagct   11100
tgaaaacttc ttttgtggac aatttttctt ttatctatgg attgtggggc atctatgttg   11160
ttcctttaag cttcgtacaa cctggtctgt gggctggtcc agtccttctt actcatgaca   11220
gtcttttgca gtaaactggt taaacttggg tgacctgttg acccacccag attggcctgt   11280
tcttttttaaa taaaacttgg ctacttataa gatttcaaca tgatacttga atgatcaccc   11340
ttactctaaa ggccattatc tgttcagtta tgttcttctt cttcttatta tttttaattt   11400
atattattat ccaacgatct gatctttgaa catgatgctg acaatcatc aaagctagtt    11460
tggttacatc atataatacc ttttttttca tatattattt ttcccatagt atattttttgt  11520
gttttttttt catacaatat tattctgaaa aaaacttgtt tcgttttttt cctggcttga   11580
atgctatttc aatgactggg ccttattatt ttctggtttta ggttatacaa ctgtcctcca   11640
attgactttt gaatgcttca atagttttct tcttaatcat ggaaggcact agagtgcata   11700
ttgaatatgt tagaacatgg aaggcttaaa tatcttttta gtctttgcaa tttaacgttt   11760
ttttgctttt agtccttgca aaattataat tttttttag tcctgactaa ttatgtttgt    11820
```

-continued

```
tttgttttg  agggcgagcc  ctggtgcagc  ggtaaagttg  tgccttggtg  acttgttggt    11880
catgggttcg  aatccggaaa  cagcctcttt  gcatatgcaa  gggtaaggct  gcgtacaata    11940
tccctccccc  ataccttcgc  atagcgaaga  gcctctgggc  aatggggtag  aaaaagaaga    12000
atgctttaga  taacactttt  tttgttactg  ttcaaagcac  tatctaaagt  gctttgagga    12060
ctaaacacaa  aacaaacata  atttgcaagg  actgaaaaac  aaaaaaataa  ttttgcaagg    12120
acaaaaaaac  aaaaaaaaaa  aacaaaattg  caaggaccaa  aaatatattt  aaaccaacat    12180
gaaattatgg  tataaaacca  ttcatatgtc  ttcatctaat  agcttaagct  tttgggatag    12240
ttggttaaca  atatggtatt  agagtcttat  gattttagg   tggtctttga  gttcaatcct    12300
tgctgctccc  agttctagtt  aatttctttt  tggtccactt  caaataaaaa  gttgaattta    12360
agggtaaggc  agctggacct  gcgcattaat  catgtgtcag  gctcaaaggg  cttttgtatg    12420
gggggcatgt  ttggaatata  atatagaatc  attcatgtgg  tttcacctat  caaggacaac    12480
tctagttttt  gtcatacttg  tattattaca  gtgtctaaac  tagacatgat  cttttccgg    12540
aaggaaattt  aacttaaaag  gaacttagat  gcttcttgtt  ctgtgatctt  tatttgttta    12600
tttttccaa   tctttttaac  aattgaaagg  ttttagttgt  atccaatctt  tttatacatt    12660
tggactatct  accatatcat  ttagcaaact  tgtttgctgc  tcagattctc  ctttggacta    12720
tctaccatat  catttagcaa  acctgttcac  tgctcagatt  ctcatttatt  ctttgtttcc    12780
tctattttc   agtggcaagt  tggagagtta  aagagactga  gaggatgata  gcaatctgca    12840
cagaactcag  aaaggtgagt  gtcttgctaa  ttcctttatg  gtttcgatat  tactggactt    12900
tttacatctc  actgacctac  tctgtcttgg  tatttcagct  aggagcaaca  gttgaagaag    12960
gtcctgatta  ctgtgtgatt  actccacctg  agaaattgaa  tgtcacagct  atagacacat    13020
atgatgacca  cagaatggcc  atggcattct  ctcttgctgc  ttgtggggat  gttccagtaa    13080
ccatcaagga  tcctggttgc  accaggaaga  catttccyga  ctactttgaa  gtccttgaga    13140
ggttmacaaa  gcactaagca  ttttgtacat  tgagtaggaa  gagagagaga  gataaatact    13200
cacaaaacag  tgagtatatg  catggcttgc  ttttgtttct  taacattccc  ttgtaagaac    13260
ttgagataat  ttgtattgtt  ggaaagagct  attgattctg  ttgtatcaaa  gtaatttaat    13320
ttccagtaca  gacttggctc  tattcctcat  atgtggtggt  gtacattgca  tctttgcatt    13380
tgatcccatt  tctattggga  taggaccata  cctttttttg  tttattattc  aagtcaaact    13440
tagcagataa  tatgtggtga  ccagaaaata  gtctagctag  caaatagacc  tgtgattgca    13500
tgtttgaatt  caggacttca  ggacatttaa  ttaatgagtg  acaatgttaa  aaagctcgcc    13560
aacaggagtt  gacacatctg  attgagtctt  ctattaacac  taactgtaac  ttgagtttga    13620
ttatcagatt  cctcctgttg  gtaggtaata  tgtaaatttc  actatatatt  taccgaggtt    13680
ggtggtctta  cttgactttg  aagaggtgag  tgtaatttaa  actttatat   caaaaaaaga    13740
ttgctaaaag  cttgagtggc  atgcaacaaa  tagcaatgaa  agaatgacta  tggccttggg    13800
aaccaaatgg  ccacgtacca  cttttccacc  aacttgagag  ccctggtcct  ggatgatgcc    13860
ccttttttt   tttcatttct  ttgacaataa  agaaagttct  tattcttggc  aattgcaagt    13920
cgtttgtgga  agtcacatga  aattccacat  aggcttcatt  gttcaaatcc  tttagtcact    13980
aactaaaggc  tggacctatg  caagaatttt  ggctactctt  ataaatgctg  tgcggcaaag    14040
actacggaaa  aatataaatt  attgcatatc  tagaggtgag  gttcattgct  cccatccatt    14100
tttccaagaa  ctaaaatata  tataaattat  taatatgata  ttacattgaa  aaataatatt    14160
```

-continued

| | | | | |
|---|---|---|---|---|
| tttcttttaa | atatgtgatc | ataagtttaa | ttttaagtct | attcatacga | aaaaaatatt | 14220 |
| tattagaaaa | gattaattta | ttaaatggat | ctcaatattt | taagaaatta | acttttagct | 14280 |
| ctcaaccaac | agatgatttg | agttaaaaaa | atgtatatat | aaactattgc | atatctgctg | 14340 |
| atttttgttt | gtaacaccaa | taagtgggca | ttttactaaa | tccatgtgac | aatgtactga | 14400 |
| atgttttaga | atacagtctg | gtttgataat | aaaacgtgca | taaagtccag | cttatgttaa | 14460 |
| ctcttaattc | atggaaaatg | atgatatgcg | aattgaaaga | agaaaacca | taatgtaagt | 14520 |
| gcagttttct | ctctcttttt | taatattatt | caatatcaga | ttgcacatgg | aagggggtat | 14580 |
| tggctcatgt | gggatattag | ttttttgtccc | ttacctaaaa | agagagaaag | agaaaaataa | 14640 |
| caatttaaaa | agagtaccac | cgctaccacc | tttttcgctt | ttaaattttt | gttctgtttt | 14700 |
| cactactctt | tcatgcgttg | tttgttggct | tctgatagtg | acgaatatga | tataatgatt | 14760 |
| ttatgttggg | aaaaaagtgc | catgtaaatt | ctagagattg | aaattttagc | atcaaattat | 14820 |
| ttattttatc | accttttaaa | atttgttgca | tgtgaaagaa | tttgaagctc | tccaacaagg | 14880 |
| aaataacact | tcaatcctta | gagtcatcct | ctagatccca | aaagaatgtg | atgtttatac | 14940 |
| acattagtat | atatatatat | atatatatat | atatatatat | atatatatat | atatatatat | 15000 |
| atatatatat | agggtttata | ttatattaat | gagtgatgta | cgaggacggt | ggtgacacta | 15060 |
| tatggccaaa | acaagtgtaa | tataattatt | ttttttctc | aagtattact | ctatccttga | 15120 |
| atattattag | tcttaaatct | tcaagcacct | tgtgaacgaa | gcaatcttgt | cc | 15172 |

<210> SEQ ID NO 33
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: modified base
<222> LOCATION: 9, 15, 21, 27
<223> OTHER INFORMATION: a is inosine

<400> SEQUENCE: 33
gcacarcgag caagagaraa agccatagcc at                                       32

<210> SEQ ID NO 34
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: modified base
<222> LOCATION: 18, 24, 27
<223> OTHER INFORMATION: a is inosine

<400> SEQUENCE: 34
gcwggaacwg cmatgcgacc rytaacagc                                           29

<210> SEQ ID NO 35
<211> LENGTH: 15941
<212> TYPE: DNA
<213> ORGANISM: Glycine maximus

<400> SEQUENCE: 35

| | | | |
|---|---|---|---|
| aaaaaatacc | ttttagtaaa | ataagagcgt | ragatcaatc | agacgttttc | tctttgggac | 60 |
| ttctcattct | taattgaatt | gacaataact | aaagtgaaac | taaggctaaa | atcaactcgc | 120 |
| ctagtcaagc | tcgtccacaa | aaataggttt | ttgaaagttt | accatgtcag | tttcttacta | 180 |

-continued

```
agtaaaaaag gatcatttgt aaggtccaac gccttaaaat gatcaccctt caaagtaaaa      240
gaatcacttg tttcacgcat aagtaagaac tacgtaggtc tgatttcctc tccaaaggag      300
ggtacgtagg agcaaaagcc ccgcttttgt cgaccttaaa aaataaaaag aaacaaaagt      360
taaggtaaca caatttccac aattctagaa ataaggttgt tgtctttcga gacaaacgta      420
agaggtgcta ataccttcct caaacgtaaa tacaactccc gaacttagaa ttttcatttt      480
gaccggtttc cttcggtttt cccgacgttt tccacaaata aacgttggtg gcgactccgc      540
gcatctttcc tcctttggaa agcgcaccca tgagcctcgc cctcgctcgc ccgcgaaggg      600
cacgttgcga cactaggtta ataagaagtt tagtccacat atctatggac ctcttaaggt      660
gattatcaaa gtggaagtgg tgacctacat gttggcccta ccagcttatt cgtatattta      720
cccccatcaa ccatgtatct cagctgaaac atgctatcaa tccaaatgtt atcagaggaa      780
catgagctgc atgttcaacc agaagtagtt ctagtcttaa tacaaatgtc aaatggcaca      840
agtgagattt tgaatttctg atgttgtaaa aatctcagga catgaatact attgggaagc      900
aattattcat acttcaccaa tccaaactga cccaaaattc tcaaatcaca tgaaagcaaa      960
aatgcatata acacgaagaa taagaagaag aggaactaac ctggggtttc gatgattaaa     1020
gcgttgttgt tgatgatgaa aacgatgatt atggagagaa attgttgttg aatggtgaaa     1080
ttgttataga aagagaacga agatagagaa aaagatatat agatttttca aggctcaaac     1140
cctaaaatca ccatgagaga gaacaaagat tgagaaacct acaaccacta tgagagagaa     1200
tgagcagaac agaagcgtga gatagagaac gagagttaag gtgcgagagg acacgaagaa     1260 caaaggtgt gagagaaaga acaaaggagc ctacggtgtg agatgagaga atttgaaatt      1320
cttaccattt aggtggaatt tcaattctac aattttattc tattaaaatt attttaaaaa     1380
atgatgtcat tttaaattct ttaaaatctc atatccaaca actgaattat gatagaggta     1440
tttcaaattc acttaaaaaa attatcttat ttaaatacccc catccaaaca tagcgaaatg    1500
ttcatgagaa ggatcaagtg gtttggaaac atagtactaa tggtgtttat acagttcatg     1560
gaatccttga tagataattt aaaggttgct ggaaattgga tgaaggtgtg gagattaaat     1620
attcttccaa aaataaagcg tttttatttgg agagtgttgt gtggttgtct cccctgtagg    1680
caaaagcttc gatgtaaagg agttcaatgt ccaataaccct atgctttcta tccctcgatt    1740
attgaaaatg aatgacacat tttatttggt tgaaatcaag aaataagcat gtggcaagca     1800
acgggtattt gacaattcat agaacaaaag gtgaatgcag caaagaatt aatgaactcc      1860 ttttcgatct acttggatca ctacatggag atattatcaa caaatttgat gttactttat     1920
ggagcagttg gaattcttgg aatgacaaga tatgaaatga acataccaac cctcctcttg     1980
tttctgtttc ggtttctatg cagtattttg ttgaatggca aagtgcaagg taatatgctc     2040
ctcaacatca attaacaaat gttcatgaca tctcttacca gctccaactt ggggacgttt     2100
gacaaacacc accgtcaagt ttccttaaat gcaacattaa tgttgctcat ttcaaggagg     2160
agaatagttt tggtgtcggc atgatactcc atcaaggaag attcgtcaaa gctcactcac     2220
gttttcgaca tgggtcgaca tgggttacct gacccaaagg ctgaggctta ggcttgggtt     2280
tgcttcaagt attgatctgg gcccagacta ttggtttaca taatatcatt tttgaaaacc     2340
taacatctaa aactcaaggt tgtttagagg tgcgccattc caaaataaga ttatcctatt     2400
tgtgcatgaa tgcgaccaac tatctcctgt ttcagcatta taaagtataa acaacaaact     2460
tctttaatca agggactaaa agatattgga catacaagct aaaagtgata gaatttgaga     2520
```

```
aaacaaatat tgacaacaat attcaagagg acactaaaac ataattctca aattttttt      2580 gtttatttaa aataaagtgg ttcattaggt agctcttgaa aaaaaaagt gattaacatg      2640 ctagtcacatg ttaaaaaaag tgaataatat tctattataa gtaaagagga ataatttatc   2700
gatgtctcat ttttgagata gttcaccgaa gccaatttt ttactttttt ctcttcaatc     2760 aatttattt tgttaatagt tgtcattgtg gatggattat aataattttg aaatgattta     2820
aaatgagata tatattaata aatttaatta attcataaat atgttactaa atataaattt    2880
catggtatac tcaggacggt tataacggaa atcaaataaa taataaaata gaataatatt    2940
aatttgcagt aaaagaata atattaattt attctgttta cactatgtat aacgaaatta     3000
aatatattca tttaatatga ttttatttt ctttaattta aaaacatgaa ttatttgttt     3060 cttatttat taccatttg ttcacttctc aattaataaa ataaaaatat attctacaat      3120
tatagtaaaa aggtttaatt ttatataatg ttagcataca gattttctc tattaactaa     3180 ttaattaaaa attatccta ttttaaggaa attaaaaatt atcatata tataagttt        3240 aaattaatta tcttatatat gtaccaaaaa gttttaaagc aattattata aaattaata     3300 aatttatcat ataaataat ttataattaa atttaaatt atcaattcat taaattaaat     3360
tatttaaaat ttttgaatga taatataata attttatcct ctactaagtc ccaacgtttc    3420
ctattttatt ccacttttag caataaattt tgtcataaac acttataaca aaaaagtaa     3480 gtaaaaaata aaaaaagtt tttcaataaa gtataaacta atttgtataa acttttagaa     3540
aaaataaagt tatacattga taatataat ttttacata attatccgat caactcatta     3600
tatatgataa atttattgat tttttaaaat aattatctta aaataattta aacaatgatt    3660
tgcaattaga tgataatata aaattattt acacactaca tgtattaaac tcaaacttt     3720 atatattagt ttttctaaaa actaatttt aactcaaaaa aaatgttact tataattttc    3780
ttatcttctt ttttttataag tatttttaa gaaatttatt gaaacatgac catgcttggg   3840
tcaataatac tactctctta gacaccaaac aacccttccc aaactataat ctaatccaaa    3900
agccatcatt catttttcctt ggtaggtaaa gttccaagac cttcaccaac tttttcactc  3960
aattgttttg gtgtaagcaa ttcgacatgt gttagtgtta gttggcaacc aaaaatccct   4020
ttatgtgact caatccaaca accactcaca ccaccaaccc ccataaccat ttctcacaat    4080
acccttcatt tacacattat catcaccaaa aataaataaa aaaacctct catttcagag    4140 agagagagag agacttcaca gaccaaagtg cagagaacaa caaagttcac aactttaagg    4200
aaaattgaaa tgcccaagt gagcagagtg cacaatcttg ctcaaagcac tcaaatttt     4260 ggccattctt ccaactccaa caaactcaaa tcggtgaatt cggtttcatt gaggccacgc    4320 ctttggggg cctcaaaatc tcgcatcccg atgcataaaa atgaagctt tatgggaaat     4380 tttaatgtgg ggaagggaaa ttccggcgtg tttaaggttt ctgcatcggt cgccgccgca   4440
gagaagccgt caacgtcgcc ggagatcgtg ttggaaccca tcaaagactt ctcgggtacc   4500
atcacattgc cagggtccaa gtctctgtcc aatcgaattt tgcttcttgc tgctctctct   4560
gaggtgaagt ttatttattt atttatttgt ttgtttgttg ttgggtgtgg aataggagt    4620 ttgatgtgta gagtggattt tgaatatttg atttttttt gtattattct gtgaaaatga    4680
agcatcatgt cccatgaaag aaatggacac gaaattaagt ggcttatgat gtgaaatgag    4740
gatagaaatg tgtgtagggt ttttaatgg gtagcaataa gcatattcaa tatctggatt    4800
gatttggacg tttctgtata aaggagtatg ctagcaatgt gttaatgtat ggcttgctaa   4860
aatactccta aaaatcaagt gggagtagta tacatatcta cagcaaatgt attaggtgag    4920
```

-continued

```
gcatttggct tctctattgt aaggaacaaa taatatcagt taatgtgaaa atcaatggtt      4980
gatattccaa tacattcatg atgtgttatt tatatgtacc taatattgac tgttgttttt      5040
ctccgcaatg accaagatta tttattttat cctctaaagt gactaattga gttgcttact      5100
ttagagaagt tggacccatt aggtgagagc gtgggggaa ctaatcttga atatacaatc       5160
tgagtcttga ttatccaagt atggttgtat gaacaatgtt agctctagaa gataaaccct      5220
cccccaaaac acaaattaga atgacatttc aagttccatg tatgtcactt tcattctatt      5280
atttttacaa cttttagtta cttaacagat gtcttgttca gcataaatta taatttattc      5340 tgttttttt tagggaacaa ctgttgtaga caacttgttg tatagtgagg atattcatta       5400
catgcttggt gcattaagga cccttggact gcgtgtggaa gatgacaaaa caaccaaaca      5460
agcaattgtt gaaggctgtg ggggattgtt tcccactagt aaggaatcta aagatgaaat      5520
caatttattc cttggaaatg ctggtactgc aatgcgtcct ttgacagcag ctgtggttgc      5580
tgcaggtgga aatgcaaggt ctgtttttt tttttgttc agcataatct ttgaattgtt        5640
cctcgtataa ctaatcacaa cagagtacgt gttcttcttc ctgttataat ctaaaaatct      5700
catccagatt agtcatcctt tcttcttaaa aggaaccttt aattatcaat gtatttattt     5760
aatatttaaa ttagcttgtc aaagtctagc atatacatat tttgattata ttctgagaaa     5820
tgcacctgag ggtgttcctc atgatctact tcaacctctg ttattattag attttctatc     5880
atgattactg gtttgagtct ctaagtagac catcttgatg ttcaaaatat ttcagctacg      5940
tacttgatgg ggtgccccga atgagagaga ggccaattgg ggatttggtt gctggtctta     6000
agcaacttgg tgcagatgtt gattgctttc ttggcacaaa ctgtccacct gttcgtgtaa      6060
atgggaaggg aggacttcct ggcggaaagg tatggtttgg atttcattta gaataaggtg     6120
gagtaacttt cctggatcaa aattctaatt taagaagcct ccctgttttc ctctctttag     6180
aataagacta agggtaggtt taggagttgg gttttggaga gaaatggaag ggagagcaat    6240 tttttcttc ttctaataaa tattctttaa tttgatacat tttttaagta aaagaatata      6300
aagatagatt agcataactt aatgttttaa tcttttattt attttttataa atattatata    6360 cctgtctatt taaaaatcaa atatttgtcc tccattccct ttcccttcaa aacctcagtt     6420
ccaaatatac cgtagttgaa ttatattttg aaggcctat tggttggaga cttttccttt      6480
tcagagatta tccctcacct ttattatagc ctttctattt ttaaacttca tatagacgcc     6540
attcttgttt taaaaacac taagttttct tttagttata ccttcccctc cttattctct      6600
ccaaagtaaa tattgtagca agtgttggtt gatccattgt gaatcttatt atcctatta      6660 acatgcaggt gaaactgtct ggatcagtta gcagtcaata cttgactgct ttgcttatgg    6720
cagctccttt agctcttggt gatgtggaaa ttgagattgt tgataaactg atttctgttc     6780
catatgttga aatgactctg aagttgatgg agcgttttgg agtttctgtg aacacagtg      6840 gtaattggga taggttcttg gtccatggag gtcaaaagta caagtaggtt tctatgtttt     6900
agtgttacat cacttttagt atccaaaatg caatgaaatt aaaactcatg tttcctatta     6960
ggtctcctgg caatgctttt gttgaaggtg atgcttcaag tgccagttat ttactagctg     7020
gtgcagcaat tactggtggg actatcactg ttaatggctg tggcacaagc agtttacagg    7080
tattcatgaa tgacactatc ttctattatc tttattttta tagcttacac tatcattcct     7140
aattcaaccc ccttctttc tctttccct cactcccaaa atagagctta tcattgtatc       7200
cttaatagct cttttatgtg ctgtttcatc tcttgagcag attctacatg attatccttt    7260
```

-continued

```
ttagtgaact ttttttgtctt ttaaataatt gatatcatca tttgaacttg cacatcatct    7320
ctatccttcc tcattttatt atatttcatt aagagtgata aaattacatt gtcaagtaaa    7380
gcaagttagc gtatcagata atgatgcttc gattgcagaa ttggtgaaag cttgcacaat    7440
tcattagctt agtgacaatt gtgatgtaga tagccataat cttccatgca acttattatg    7500 cttttttgtct aaaacttctt ttgcacttaa acatgaatta gagagttagg atgaacaata    7560
gtaacagaca caaagcttat ttctagacca cccagtggtg aagacgaagc agcatgagtg    7620
agattaatgg cagcatctga ttgaagcttc ttttggtatt attggagatg aaatcttgag    7680
ccaaattagg gcttttgcct cctcaatagc cattggttca aaattgcttt caataaaatg    7740
attacagaat caaattctta agaaagacct tcaagaacaa catcaagatg tttcctgtgc    7800
aaaacaggct cacctacaaa agagtgtcta caagcaccttt tacacttgca aaaaattcct    7860
taactgaaca attgccaaga gtcatgttgc aaacttgaga ttggagttga ttagatttgg    7920
tgtgtgtgag attctggaaa tgagcatgaa gttttttgca aagctcataa aatgaatgca    7980
gccaagaatc ctagatagga ttgaatttga gagagaggct tgaagtcaag ataaccgcaa    8040
ctgatcttgc tgttcccatg ctgcatagga ctcgttgatt ctaccaagat aacaatcttc    8100
tgtggtgaga atatgagtgg gaattgtcag gcaacaaaga aaatgaaggc tatgagcctt    8160
tgttaaggtg cagagagaaa acagaaaatg aagaacttgt gtattgaagg aattgaaaag    8220
ccaattacaa ttgtgttgca gagagatatt tatagttctg aagtgtataa ctaactaaac    8280
agaatgctac caacctagag gcagttgaga attgctccct tattacaata ctctcacagc    8340
cttgatgata ggcttgattt gctgccaccg aagaagaaca ttattgttgg agagttttttc    8400 agtgattgca tcagagaaag ttacaagtgt gattggagat gaaggacttg cggtcgtcga    8460
aggttaagtg ttaagtggtg gaatgtgtat cggaggtggt tgcctagccc aagaagctgg    8520
ttgcagtgga agcggatgcg gcagaagcca tgggttcaga tcagaactat gttctagata    8580
ccatattagg gttagctttc aagagaaaac ttatgaaact gaactgtaaa ctgttgtatt    8640
attgattagc tgatctagta gtgatggaag cttgcttgcg aagcttctat ggaggctgga    8700
tcattgagct tcaatgaggt ccttcaatgg tgatttttca ccatggagat gcagcggaag    8760
ataaatgaag aggtgagagg aggcgtcatc cactaggaaa taaactatgg aagaaggagc    8820
ttcaccacca agagagtgtc ttggataaga agcttagaga ggaagcttca atggaggaat    8880
agaaagagag aggggaaca aaaaattgaa ggaggaaaag agggagagaa gttgaacttt    8940
gaagtgtgtc tcacaagact cattcattaa agttacaaca agtgttacac atgcttctat    9000
ttatagtcta ggtaacttcc ttgagaagct agaacttaac tacacacacc tctctaataa    9060
ctaagataac ctccttgaga aatttccttg agaagcttcc ttaagaagat tcctagagaa    9120
gctaaagctt agttacacac acctctctaa taactaagtt cacctccttg agatgagaag    9180
ctagagcctt agctacacac acccttataa tagctaaact cactctattc caaaatacat    9240
gaaaatacaa aaaagttcct actacaaaga ttactcaaaa tgtcctgaaa tacaagacta    9300
aaactctata ctactagaat ggtcaaaata caaggtccaa aagaaggaaa aacctattct    9360
aatatttaca aagagagtgg acccaacctt agtccatggg ctcagaaatc taccctgagg    9420
ttcatgggaa tcctagggtc ttctttagta gctctagtcc aattttcttg gagtcttcta    9480
tccaatatcc ttgggggtag gattgcatca tgtagtacaa gagagggaa tatatataca    9540 gttgtaagtt gtaactacct aatcaaaccc aactgactca ccatacacag aaaaacaatg    9600
tacaaaggat aatagaaaaa ctgaaactga gatatactca ttacatagaa gaattacatg    9660
```

-continued

```
atgaatctga aaattttaat tgggaaactg aggacaataa caaggctttc agagttcatt      9720
ttgacaatag gtaaattatg gacttcaact tagacctcaa gggtatgctt gggagtgggg      9780
ttttagagga aaaggggaag gagggaaatt ttttaattct agtaaatatt ctctattttg      9840
attaattttt aaaataaaac aaataaactt atagattagc attcacttaa tgtcctgatc      9900
ttttatttgt ttcatgaagt ttttttatagc ctttctgttt ctgttaaaag aaattggagg     9960
gtgttcataa tctatatgcc catatatatg tattgtcctg ttgtctgtgt ttctgttttc     10020
tttctttagt gtctcgcctt tccttaattc cttatcaaca ccttgtttat ttttgaaaac     10080
ttaaatgtcc tcatttttttt tacctgtact ataactttcc aaacaaatag tagaaaatgt    10140
ttcaaatatt ccccagaact gtttcagtga acaaagttca agccagaaaa aaagcaagca    10200
gaggctaaag aagtatatct tattgtgaag agtaatctca attggttaat tatcgaattg    10260
tatcatttta caatagaaaa ttagaagtgg gttgattagt ttatacgaac aattatttaa    10320
ataggggtga tggtgtggtt aattactgat catatgttaa gactatgagt cgatgaccag    10380
cctcagtgca gtcattttaa gttccattat tttttaattg tgcttatgtt taactttgtc    10440
cttcttttaa agggagatgt aaaatttgct gaagttcttg aaaagatggg agctaaggtt    10500
acatggtcag agaacagtgt cactgtttct ggaccaccac gagattttttc tggtcgaaaa   10560
gtcttgcgag gcattgatgt caatatgaac aagatgccag atgttgccat gacacttgct    10620
gttgttgcac tatttgctaa tggtcccact gctataagag atggtatggt ttagctgttt    10680
gtttttgctc aagagcttgt tttcacatat ttgtggtcaa gagcggttta gctgtttttt    10740
tttttaaatt gtggttaatg aaattattat aattatacta atattgaaat tggatcacta    10800
accatgtgaa atgcttgaat ttttagcttg aaaacttctt ttgtggatga ttttttctttt   10860
atctatgtag tgtggggcat ctatgttgtt cctttaagct ttgtgtcata gttgtacaac    10920
ctggtctgtg ggctggtcca gttcttactc atgactgtct tttgcagcaa actggttaaa    10980
cttgggtgac ctgttgaccc acccagattg gcctgttctt ttttaaataa aactccaaaa   11040
ggctacttat aagatttcaa catgatactt gaatgaccac ccttacttta aaggtcatta   11100
tgccatcaga ccccttgatt ctctgttcag ttatgttctt attcttatta ttttttaatt    11160
tatattatta tccaacgatc tgatctttgt acatgatgct ggacaatcat caaagctagt   11220
ttggttacat catataatac cttttttttc ataaattatt ttttcccata atatatttat    11280
atgtattttt ttaatacaat attctgggga aattttttttt ttctgttttc ttttttctgg  11340
tttgaatact atttcaatga ctgggcctta ttattttctg gtttgggtta tacaactgtc    11400
ctttgatgta cttttgaatg cttcaatagt atttttcata atcatggaag gcactagagt   11460
gcagtgcata ttgcacaagg ttctttaatg gcatcttgaa tttgttagaa catggagtta   11520
tgatatacaa ccattcctat gtcttcatct aatagctaaa gcttttggcg tagttggtta   11580
acatggtatt ggaatcttat tttaaaggtc catcttattc gcaagtacaa ggcaggtgga   11640
cctgcgcatt attcacgtgc caggctcaaa gggattttgt atgaggggga atttttggaa   11700
tataatatat agaatcattc atgtggttca cctatcatgt gtcaactcaa gttttttgtcc  11760
tagttgtatt attgcagtgt ctaaactagg catgatcttc tgtggaagga aatttaacct    11820
aaggaacttg aatgcttctt gttctgagat ctttattttt tttctccaat cttttttaata  11880
cttgaaaggt tttagttgta tctataaagg gtgcagaatt agggggtcag cttttctgtt   11940
gtaagcgtga attaagtgca ttttatgttg ttccctattt tatacatttg aactatcaac   12000
```

-continued

```
catatcattt agcaaacttc tttgttgctc agattcccat ttattcttgt ttcctctatt    12060
ttttagtggc aagttggaga gttaaagaga ctgagaggat gatagcaatc tgcacagaac    12120
tcagaaaggt cttgctaatt cctttatggt ttctatatta ctggactttt tacatctcac    12180
tgacctacta ctgtcttggt atttcagcta ggagcaacag ttgaagaagg tcctgattac    12240
tgtgtgatta ctccacctga gaaattgaat gtcacagcta tagacacata tgatgaccac    12300
agaatggcca tggcattctc tcttgctgct tgtgggatg ttccagtaac catcaaggat     12360
cctggttgca ccaggaagac atttcctgac tactttgaag tccttgagag gttaacaaag    12420
cactaagcat tttgtacatt gagtagggaa gagagagaga tatatataaa tactcacaaa    12480
gcagtgagta tatggcttgc ttttgtttct aaacattcct ttataaggac ttgagataat    12540
ttgtattgtt taaaagagcc attggttctg ttgtatcaaa gtaatttaat tttcagtacc    12600
gacttggctc tactcatatg tggtggtgta cattgcatct ttgcatttga ttccatatct    12660
attgggatgg gaccatacat ttttgtttta ttatttaagt caaacatatc agataatatg    12720
tggtgaccag aaaagtgtct agcaatcaaa tgggtctgtg attgcatgtt tgagttcagg    12780
acatttatta atgagtgaca gaattttaaa agctcgcca ataggagttg ccacatctga    12840
tcgagtcttc tgtaaacact aactgtaact tgagtttgat aatcagattc cccccgttgg    12900
taggtaatat gtaaatttca ctatagattc ttactgagga tgatggtctt gacttcgaag    12960
tggtgagtgt aattctctaa tctaaacttt atatatatat aaaaaagaa tgttaaaaac     13020 ttgagtgaca tacagcaaat agcaatgaaa gcatgaccat ggccttgggg ggccaaatgg    13080
ccatgtacca cttttccacc tacttgagag ccatggtcct gaatgaggtc cttttgtttc    13140 attttttta caataaagaa agttcatatt cttggcaata gcaaggcaaa tcatttgtgg     13200
aagtcacatg aaattcacca taggcttcat tgttcaaatc ctttagtcac taaggcaggg    13260
cctatgtaag aatttttgact actcttgtaa atgctgtgcg gtaaagacta cgggaaaata    13320
taaattattg catatctaga ggtgaggttc atttctccga tccatttctc caagtaataa    13380
aaatatatat aaattattaa tatggtatga tatggttatt tgtccttaa atatgcgatt     13440 ataggttcaa tctttggtta atctatcaaa tgcatctcaa tattttgaga gaatagtttt    13500
tagctcttga ctgagagata ctttgagtta aaaaatgta tttataaact attgtctatt     13560
gaatttttat ttttttgta acaccacatg tgagtatttt actaaatcca tgttacaatg     13620
tactgaatgt tttacaatac agtctggttt gataataaaa tatgcacaaa gtccagctta    13680
tgtaactctt tcaattcatg gaaatgatg atatgcgaat tgaaagaaag aaaaccataa     13740
tgtaagtgta tttttttttt ctttctcttc tttaatatta ctcaatatca gattgcacat    13800
gggaagggta ctggctcatg tgggatatta attttatcc cttacctaaa agagagaaa     13860 gagaaaataa ctatttaaaa agagtaccac caccaccttt ttcgctttta agttttgttc    13920
tgttttcact actctttcat gcgttgtttg ttggcttccg atagtgacga atatgataat    13980
gattttacgt tgagaaaaaa aatgtgccat gtaaattcca gagattgaaa ttttagcttc    14040
aaattaatat ttattttatt atcttttcaa attggttgca tgtgaagaa tttgaagttc     14100 ttcaacaagg aaataaacac ttcaatgctc aatccttaga gtcagtcact agatcccaaa    14160
agaatgtgat gtttacacac attagtatat atatatatat aaacacagct tatattata    14220 taatgagtga tgcgcgagga cggtggtgac actacatggc caaaacaaga aatgtaattt    14280
aatttttttt tctttaagta ttactctatc cttgaatatt agtctaaat cttcaaagac     14340 cttgcgaacg aagcaatctt gtcctgatcc tgtgattgtt ctacactagt ccttacgtgt    14400
```

-continued

```
acctaagcac atgatacttt gctgccctaa cataaattgt accataagga ttcttgggga    14460
gatgcttttg ccttcatttt caagtttgtt tacactttca agtcgttttt tcaatgcatt    14520
ctctttcctt tctgggaccc cttgtcttta acacgcgcgc acacaaaaac tagtagacaa    14580
taattagtac tacttgggtt ccattaaatt gtaactacat atacatgtgt ttttttttc    14640 ttggatcaac tgcatataca tatgttttat gagtttcatt gaatttatat ttacacaaac    14700
agttattaaa acataatgta gagccttgtc attaacctga tgttaggatt ataatttcat    14760
gctttgattt tgattgtacg ttttttgttt ttattgtaaa gtgtttattt tattaaaatt    14820
tgtcttggag tgctgtgatc tttagggtgc accgttcaaa agagagacga caaggataat    14880
actaatacta gtagattcca cgcattcaac cctagttagt ttagctatga caaattaagc    14940
atggtaagaa aaggggagga gaaaagtaag aatgaaaaca tataacaaat tgtgattgaa    15000
cttttccatg acgtaatgaa aacattaatt ttaagataag cttcaactcc taagaagaga    15060
tatgtcaaag aaacttagga ttttttctct atttataacg gtaaattact catcctttta    15120
aatgattaat ttgcgttgtt gaattcgttg taaagggaaa atcaagaagt ctcttcacgg    15180
gaaagttata tcaaagtatc atatactaga cttcatggct agcttttact ttgattataa    15240
gtaatgcatg caattaatgg gcaaataaat tatttgaaac caactaaagt acaaataatt    15300
ttcctccaaa acctctcaag ttcgcattga aattaaataa accaatgcat attaaggcgt    15360
aaatctaaac catgtttgtt tcatcttgta ttgtatatca tagtattaat aaggtacttt    15420
gaatttagtt gttattgacc gttaaattta ggggtgagtt gttttactat ctcttactca    15480 attgcttttta ttcaacgcaa attctagtag gattttcagc ccaaattaaa agaagtttta    15540
cggtttgatt ctctacaaac ttgaattgag atttctaatt tcagaaatca ataattgcgg    15600
tcttaattaa ctctataatc aaaccttta acccaatctt tttctcaatt ctctgaatta    15660
agacaatcaa aatttaaact cacacgaatc tcacacgcct tcccacggta gagaaatata    15720
gggagtccct taatagcaaa agcctcaaaa ttcagaaaat ctcatccatt gcatttgcac    15780
attcaacaaa ccacccatta ttatgttccc ttaataaatc tcacacttaa aaaccctcct    15840
cacccataat taacccaaaa ggaagttttcc tccacacaaa aaatatcctt aaacaaagag    15900
cctctataaa tctattttaa aaaacccccc aaatttaagg a                        15941
```

<210> SEQ ID NO 36
<211> LENGTH: 15172
<212> TYPE: DNA
<213> ORGANISM: Glycine max EPSPS with double mutation

<400> SEQUENCE: 36

```
aaaagtctga atgaagtgaa gttgttgtgt taggggatg ctgaatttga ttttaattta      60
atttaaataa attacctgtg taaaggattt ttgtaccgcc ttttaatcac aaattgtcgt    120
gtatcgaaag tttgttgaat tttatagtaa ctatcttgga ggttatacct agtaggattt    180
ctgattagtt aaccatgtaa atttttttaa tgggtttgtg tttgttttaa ctgatgttgt    240
ttttgatatg tacgtggtaa gtgtgatgag tttgtgcata tcttgatcaa agactgaagt    300
gaagttgttg tgtttggggg gttgactctt ttaggaagag gatttgaggg aatttcgcca    360 atggggggagc agaactccgg gacaccctga gaattttgag actccgggaa ttgaagttac    420
aacaggtttg atatgagtta gagtttgtat aatagaatag taattctttt tatttttat     480 ttttattgtt tatttatcca ttattgctat ttttgtaggt cctcttggtc agggattgc     540
```

```
caatgctgtt ggtttggccc ttgcagagaa gcacttggct gcaagataca acaagcctga    600
caatgagatt gttgaccatt acacgtaaaa ataactaaat catacacaac ttgcaagact    660
ttagttgttg gtgttttgct aatggcgttt gttttatgca ggtatgctat tctgggtgat    720
ggttgtcaaa tggagggaat tgcaaatgaa gcatgctcac ttgctggcca ctggggactg    780
gggaagctga tagcatttta tgatgacaat catatttcta ttgatggtaa cacagagatt    840
gcgttcaccg agagtgttga tagtcgtttt gagggacttg ggtggcatgt tatttgggta    900
aagaatggaa ataatggcta tgatgatatt cgtgctgcca ttaaggaagc aaaagctgtc    960
aaagacaaac ccacattaat caaggttagt ttactaattg tggcaatgat atgcatagat   1020
ttctggcttg tagttaccat aacaatcata atctgtcatg atttataggg attcttttaa   1080
actaaggtta taaacatgat atgttactaa agactgcatt gcattgtagt acctcatttg   1140
agaaactgga agttataggt gggaaatcaa aatagtaaat tatgggtcag tttattaagt   1200
gtagctggtt tgtcttttgc taactctatc atttcacagg tcacaacaac cattggttat   1260
ggttctccta acaaggctaa ctcctacagt gtgcatggaa gtgcactggg tgccaaagaa   1320
gttgatgcca ccaggcagaa ccttggatgg tcacatgagc cattccacgt gcctgaggat   1380
gtcaaaaagt atggatgatg ggtttagaga tttcttttt cctgtgacac tgctgatgtt   1440
tataatgata ctgaataaga attgcttgtc tgtccccagg cattggagtc gccacacccc   1500
tgagggtgct gcacttgaag ctgagtggaa tgctaagttt gctgagtatg aaaagaaata   1560
caaggaggaa gctgcagaat tgaaatctat tatcaatggt gaattccctg ctggttggga   1620
gaaagcactt ccggtgagta aattctaaac tcacaggttt ttcttacatg tttgtaactt   1680
ttcaaggttt ggattacata ctatccaaag ttgatcatga tttcagtttg atttggtagt   1740 atgggcttc aaaaagttat tccaaatatt aaaacctggc ttccaatttg atttcagaca   1800
tacactccag agagcccagc ggatgccacc agaaacctgt ctcaaacaaa ccttaatgcc   1860
cttgcaaagg ttcttcccgg tctgcttggt ggcagtgcag atcttgcttc ttccaacatg   1920
accttgctca aaatgttcgg ggacttccaa aaggatactc cagcagagcg taatgttaga   1980
ttcggtgtta gagaacacgg aatgggagct atctgcaacg gcattgctct tcacagccct   2040
ggactgattc catattgtgc aaccttcttt gtattcactg actacatgag aggtgccata   2100
aggctttctg cgctgtctga ggctggggtt atttatgtca tgacccatga ttcaatagga   2160 cttgagaag atgggccaac ccaccagcct attgagcacc tagcaagctt ccggcaatg   2220 ccaaacattt tgatgcttcg tcctgccgac ggtaacsgaa acagccsgag catacaaagt   2280
ggccgtgctc aacaggaaag agaccctcca ttcttgccct atccaggcaa aaactgcccc   2340
agcttcccgg aactthcatt gaaggagttg aaaagggtgg ttacaccatt tcgggacaac   2400
tccactggca acaagcctga tgtcattttg atcggaactg gttcggaatt ggaaatcgct   2460
gccaaagctg ctgatgacct aaggaaggaa gggaaggctg ttagagttgt ttcccttgtt   2520
tcttggggaa ctttttgatg agcaatcaga agcstacaag gagagtgttt ccctgctgc    2580 tgtttcagcc agagttagca ttgaggcagg atcaacattt gggtgggaga aaattgttgg   2640
agcaaaggga aaagcaatag gcattgatcg ttttggagct agtgctccag ctggaagaat   2700
atacaaagaa tttggtatca ctaaggaagc tgttgttgct gcagctaaag agcttatcta   2760
gaacttttga ttttttttg ccttctggtt ttggttgaga gcattccatg tcatgaataa   2820
gaaaaaggtt aaatatccctt cgattgggaa tttgggattc taagtgaaga agcaacatag   2880
atcaaagaat tttgtgaact tgtaataact atttgacaat ttagttttgc actgccacat   2940
```

-continued

```
ggttaaattc aatgtttgat catatcaacc atagatgcta gtttatacta cttgtataat    3000
ttgtttcact tgcagattca ctcttagcat ttgagtgttt ggatggccgt gttttgttca    3060
ttaagaaatg ttgacatgga tagtttgttg catggtaaat tggtgattaa tacctttta     3120 agcttctttt ggcaagttgt taaaaagtgt tttgttttaa tctctagtta atctaaaaat    3180
gcctacttat tttattttga cttttcaaaac ttgtctatat gccgagtata aaaaaaactt   3240
gtctatataa gttccttatg gaaaaaggac ctacaaaata atttaaaaat gctgaatttg    3300
ttaggaagtt tgacaacttt agacattaat aattgttttt ttttcatata tataattgac    3360
tttcaaaact tgtctatata ttataaattc gttatggaaa gggcgaccac acgtaaaacg    3420
taacatgcca atctctccct agtgaactgt tattctcatt cagttttgt aagttcacct     3480 tcaaattttc aatttttttt ttgacaaaaa tatctttgat ggaacacgtt aggggtgtaa    3540
attcaccatt catcatttca ttcattatac acaatagtct ttcataatcc aatgaaaact    3600 tgttttgtt gttatttttt tctgaaaaat ctttataaaa taaataaaaa catttttttg     3660
ttataaattt cagttgaaat acataaccat taattctaca gagtgttaat gttgatgtaa    3720
aataaaaaaa tattggatat caaacttaat gaacagaaca aaaattacaa aattgtacaa    3780
tttaaatgat aaaaaaccaa attcacaaaa ataaaaatta aggacgaaat ttgagaaatg    3840
ataattaaaa acgattaaaa atataattaa actaaaattt attatgtaat tctttaatat    3900
atatatatat atatatatat atatatatat atatatatat ataataaaag ttttacatta    3960
taattttgaa atgaagtatt tgataaacga acaacccacc cttggggttg gtgagagtga    4020
aacggagaac agtgtctccc tcacttggtc ttctgagtcg agtcctattc atcaccaacc    4080
cactcgtcaa aattgttgta tgctatgtaa ccatttttgtt ttttaataaa taaaagtgtt   4140
ttgttctgct atgcactccc catcaaatac catttacttt ttttttgtct tctatcaatt    4200
tctatttagt tcctagttgc tacaacttcc agctggtgaa aaatagtcaa cagagactac    4260
aatattctaa taaaatagaa taacaaaatc aaatatattc atttaatatg attttatttt    4320
tatttaattt aaaacatgaa ttatttgttt cttatttaat taccgtttcg ttcacttctc    4380 aatttaataaa ataaaaaatt tctacaatta tagaaaaagt ttagttttgt agattgttaa   4440
cataaagatt tttcctatta actaattaat taaaagtcat cttatatata agttttaaag    4500
taattatctt atatatgtac ccaaaagtttt taaagcaatt attataaaaa agtaaaattt   4560
tatcatatac aataatctat aattcacatga agtataatt tttaaattat taatacgtta    4620
aaattatttt tttaaaatttt gaatgatcat atagtaattt tattttatac caagtcccaa   4680
catttcctat tttattccac ttttaccaat aaatttcctc ataaacactt ataagaaaaa    4740
aagtaagtaa agaataaaat aagcttttct ataaactata aacaaatttg tataaacttt    4800
cttatattag ttttttctgaa aactaatttt aaattataca taaattgaat ttactgataa   4860
ttttttattt tctttttgta taagtgtttt ttaagaaatt tgttcaaaca tatttttatg    4920
acatgtcaat gcttgagaga tataaggtga gttaaatcat aaatgattaa agaaaaataa    4980
aagaagaaaa agataattaa tttaatttt tattaacatt ctaacaaatt aacattatat     5040
aaataaaaat aatatttcaa taattggatc aataatacta ttgttcttaa acaccaaacc    5100
aaccttccta aagtcctaat ctaatccaaa agccatcatt catttttcctt ggtaggtaaa   5160 gttccaaaac ctttaccaac cttttcactc aattattttg gtgtaagcaa ttcgacatgt    5220
gttagtgtta gttggcaacc aaaaacccct ttatgtgact cactcaatcc aacaacctct    5280
```

```
cacaccacca accccccccat aactcataag gccaaaacca tttctcacaa aacccttcat   5340
tacacacatt attatcatta tcacacacac aaaaaacctc tcatttcaaa gagagagaga   5400
gatttcacag accaaattgc agaggacgac aaagttcaca acttcaagga aaatcgaaat   5460
ggcccaagtg agcagagtgc acaatcttgc tcaaagcact caaattttyg gycattcttc   5520
caayyccaac aaacycaaat cggygaattc ggtttcattg aggccacgcc tttggggksc   5580
ctcaaaatct cgcatcyygr tgmayaaaam tggaagcytt atgggaaatt ttaatgyggg   5640
gaagggaaat tccggcrtgt ttaaggtttc tgcatcsgtc gccgccgccg cagagaagcc   5700
gtcaacgtcg ccggagatcg tgttggaacc catcaaagac ttctcgggta ccatcacatt   5760
gccagggtcy aagtctctgt ccaatcgaat tttgcttctt gctgctctct ctgaggtaaa   5820
gtttatttat ttatttatttt ctgtatccaa aaatgtaaat tgttagtttg ttaattttg   5880
ttagcagtga gagtcgaact acttggcttc tttcttagtc atccaaccaa ccttatatct   5940
ccaaaattta tttattggtt ttttttgggg ttatgtggtt aggaatagga gtttgatgcg   6000
tggagtggat tttgaatatt tgatttttttt ttttttgta ttattcagtg aaaatgaagc   6060
atcttgtccc atgaaagaaa tggacacgaa attaagtggc gtatgattta gaatgatgat   6120
agaaatgtgt ataggtggtt ttaatgtgta gcaataagca tattcaatat ctggattgat   6180
ttggacgttt ctgtataaag gagtatgcta gcaatgtgtt aataatgtct tgttaaaagt   6240
atggatggct aaaataatca taaaaatcga gtgggagtag tatacatatc tacaggaaat   6300
gtattaggtg aggcatttgg cttctctatt gcgagtaagg aacaagtaat ctcagttaat   6360
gtgaaaatca atggttgata ttccaataca ttcatgatgt gttatttacg ggaacgcaat   6420
attgactgtt gattttatct gcagctgaga ttatatacta tatccttcca aagaaatctt   6480
tgactcttga ttatccaagt atggttgtat taccaatttt agctctagaa gataatccct   6540
cccccaaaac acaaattaga atggtgctgc aagttccgtg ttactttcat tctattattt   6600
ttataactt taattattta atagatgtct tgtttggcat aaactataat ttattctgtt   6660
tttttttatt cttatttagg gaacaactgt tgtagacaac ttgytgtaya gygaggatat   6720
tcattacatg cttggtgcat taaggaccct tggactgcgt gtggaagayg acmaaacaac   6780
caaacaagca attgtkgaag gctgtggggg attgtttccc actaktaarg aatctaaaga   6840
tgaaatcaat ttattccttg gaaatgctgg tactgcratg cgtcctttga cagcagctgt   6900
rgttgctgca ggtggaaatg caaggtctgt tttttgtttt gttgttcat catgatctct   6960
gaattgttcc tcgtataact aatcacatca gactatgtgt tcttcctcca tcctgttata   7020
atctaaaaat ctcatccaga ttagtcatcc ttctttaaat gaacctttaa ttatatctat   7080
gtatttattt aacatgtaaa ttagcttgtc aagtcaaagt ctagcatata gatatactga   7140
ttacactctg aggaatgcac ctgagggtct taatcatgat ctatttcaac cttgccactt   7200
tcttctttta ttattagatc acctatcatg attactggtt tgagtctcta aatagaccat   7260
cttgatgttc aaaatatttc agctacgtac ttgatggrgt gccccgaatg agagagaggc   7320
caattgggga tttggttgct ggtcttaagc arctyggtgc agatgttgat tgctttcttg   7380
gcacaaactg tccacctgtt cgtgtaaatg ggaagggagg acttcctggc ggaaaggtat   7440
ggtttggatt tccattagaa taaggtggac taactttcct ggagcaaaat tctaatttat   7500
accctgtttc ccctctttta gaataagaca ctaagggtat gtttaggagt tgggttttgg   7560
cgagaagggg aagggagggc aattttttt ctaataaata ttcttaattt tgataaattt   7620
tttaaacgaa ggaatatgaa gatagattag cataacttaa tgttttaatc ttttatttat   7680
```

```
ttttataaat attatatacc tctatttaaa aacaagatat ttttcctcca ttccctttcc    7740
ctttaaaacc tcagttccaa ataccgta cttgaattat attttggaag gtgtattggt    7800
tggagacctt tccttttcag aggttatccc tcacctttat tatagccttt ctactctctt    7860
aatgagttca ttgtgcattg agtcattgaa cttcctgtga aaagaaattg tttacttttc    7920
tttatttgtt acctacatcc ttattcctgt tttaaaaaat actaagtttt cttttagtta    7980
tgccttcccc tccttattct ctccaaagaa aatataatag cgaatgttgg tttatccatt    8040
gtgaatctta ttatcctatt tcacatgcag gtgaaactgt ctggatcagt tagcagtcaa    8100
tacytractg ctttgcttat ggcagctcct ttagctcttg gygatgtgga aattgagatt    8160
gttgataaac tgatttctgt tccatatgtt gaaatgactc tgaagttgat ggagcgtttt    8220
ggagtttctg tggaacacag tggtaattgg gatargttct tggtccatgg aggtcaaaag    8280
tacaagtagg tttctatgtt ttagcattac atcacttttt agtatccaaa atgcaatgaa    8340
atcaaaactc atgttttcta tcaggtctcc tggcaatgct tttgttgaag gtgatgcttc    8400
aagtgccagt tayttmctag ctggtgcagc arttactggt gggactatca ctgttaatgg    8460
ctgtggcaca agcagtttac aggtattcat gcttgacact attttctatt atcttttatt    8520
ttatggtcta tactgtatca ttcctaattc aaccccttc ttttctcttt cccctcactt    8580 ccaaaaaat agagcttatc attgtattct taatagctct tgtatgtcct ttttcgtctc    8640
ttgagcagat tctaccgtga ttatcctttt tagtaaactt ttttttttgtg tgtcttttaa    8700 ataattgata tcatcatatg aattcacaca tcatctctat cccttcctca ttttattata    8760
tttcattaac agtgataaag ataaaaataa attgtcaagt aaagcaagtt agcatgtcag    8820
ataatgatgc ttcaattgca aaattggtga agcttgcac agtacattag ctttggtgac    8880
aattgtgatg tagatagcca taacctccca tgcaacttat tatgttgttt gcttaaactt    8940
cttttgcact taaacacgga ttagagagag tgaggatgaa caataataac agacacaaag    9000
cttagtttta taccacccgg cacccagtgg tgaagaccaa gcagtatgag tgagatcaat    9060
ggcagcatct gattgaagct tcttgtggta tttttggaga tgaaatccga ggcgaattag    9120
ggcatctggc tcaacaatag ccattggttc aaacttgctt ttaataaaat tgattacaga    9180
atcaaattct tgaggaagcc ttcaagaact acatcatgat gttccctgtg caaaacaggt    9240
tcaccgacaa aagagaacat ctacaagttc ctttacacat gccaaaaatt cctcaactga    9300
acaattgcca agagtcatgt tgcgaacttc aggttggagt tgacgaaatt tggtgcatgt    9360
atgattctgg aaatgagcat gaagtttttt cctaagctca taaaagtgaa tgcagccaag    9420
aaccctagat aggattgaat cggagagagg cttgaagcca agataacagc aactgatctt    9480
gctgttccca tgctgcgtag gactcattga ttctaccaag atcacaatct tctgtggtga    9540
gaaaatgagg gtgaattgtc aaccaataaa gaaaatggtg aaggctgagt cttgatgata    9600
ggcttgattt gcttgcgctg aagaagaacg ttattgttgt agagtttctc agtgattgta    9660
tgagagtaag ttacaggtgc gattggagat gacggacttg tggtgggagg agggtaagtg    9720
ttaagtggtg gaatgcgtat cagaggtggt tgcccagcca aagaagctgg ttgcggtgga    9780
ggaggtggtg gtgcagtgga agccatgggt tttgatgctt ttgagagaaa catacgaaa    9840 ctgaactgta aacttttgta ttattgatta gctgatttgg tagtacaaga gaggaatata    9900
tatacagttt taatgtaact acctaaccaa acatgaggaa ctctccatac acagaaagac    9960
gtatacaaag gataacagac aaacagaaac ttagatatac tcatacagag aagaattaca   10020
```

```
ggatgaatct gagaatttta attgggaaac tgaggaaaat agcaagggtt tcagaattca    10080
ttttgacgat aggcaaatca tggacttaac ttagacctca agggtacgct tgggagtggg    10140 ggttttaga gggaaaaggg aaggagggca aacttttaat tcctaataaa tattctcttt    10200 tttgatttt ttttaaataa aacaaataaa cttatagatt agcatacact taatgtccta    10260 atctttatt tatttgcatg agttttttc ttttatattc tttctgtttc tgttttcttt     10320
cttcagtgtc tcttgtcttt ccttaattcc ttatcaatac cttgtttatt tttgaaaact   10380 taatttcct catttttta acttataggc tatactatag tatgtataac tattcaaata     10440
aatagtagaa aatgtttcaa atattcccca gaactgtttc agtgaacaaa gttcaagcca    10500 gaaaaagaa gtatatcttc ttgtgaagag tagtctcaag tggttaattg tcaaattgta    10560
tcattttaga atacaaaatt agaagtggtt tgattagttt atacgaacga ttatttaaat   10620
agggttgatg atgtggttaa ttactgatca tatgtgaaga ctgtgagtcg atgaccagcc    10680
cagtgcagtc atttttaaatt ccattatttt ttaatttgtg cttatgttaa actttgtcct  10740
tctttcaaag ggagatgtaa aatttgctga agttcttgaa aagatgggag ctaaggttac   10800
atggtcagag aacagtgtca cygttwctgg accrccacra gattyttctg gtcraaaagt   10860
cttgcraggc attgatgtca atatgaacaa gatgccagat gttgccatga cwcttgcygt   10920
tgtygcacta tttgctaatg gtcmmactrc yatmagagat ggtatggttt agctgttgt    10980 ttgtgttcaa gagcttgttt taacaaattg tttttttaa ttatggttaa tgaaattatt    11040
ataattacac taatattgaa attggatcac taaccatgtg aaatgcttga attttagct    11100 tgaaaacttc ttttgtggac aatttttctt ttatctatgg attgtggggc atctatgttg   11160
ttcctttaag cttcgtacaa cctggtctgt gggctggtcc agtccttctt actcatgaca   11220
gtcttttgca gtaaactggt taaacttggg tgacctgttg acccacccag attggcctgt   11280 tcttttaaa taaaacttgg ctacttataa gatttcaaca tgatacttga atgatcaccc    11340
ttactctaaa ggccattatc tgttcagtta tgttcttctt cttcttatta ttttttaattt  11400 atattattat ccaacgatct gatctttgaa catgatgctg gacaatcatc aaagctagtt    11460
tggttacatc atataatacc ttttttttca tatattattt ttcccatagt atattttgt    11520 gtttttttt catacaatat tattctgaaa aaaacttgtt tcgttttttt cctggcttga    11580
atgctatttc aatgactggg ccttattatt ttctggttta ggttatacaa ctgtcctcca   11640
attgactttt gaatgcttca atagttttct tcttaatcat ggaaggcact agagtgcata   11700
ttgaatatgt tagaacatgg aaggcttaaa tatcttttta gtctttgcaa tttaacgttt   11760 ttttgcttt agtccttgca aaattataat tttttttag tcctgactaa ttatgtttgt    11820 tttgttttg agggcgagcc ctggtgcagc ggtaaagttg tgccttggtg acttgttggt   11880
catgggttcg aatccggaaa cagcctcttt gcatatgcaa gggtaaggct gcgtacaata   11940
tccctccccc atacctttcgc atagcgaaga gcctctgggc aatggggtag aaaaagaaga  12000
atgctttaga taacactttt tttgttactg ttcaaagcac tatctaaagt gctttgagga   12060
ctaaacacaa aacaaacata atttgcaagg actgaaaaac aaaaaaataa ttttgcaagg   12120 acaaaaaac aaaaaaaaa aacaaaattg caaggaccaa aatatatttt aaaccaacat    12180
gaaattatgg tataaaacca ttcatatgtc ttcatctaat agcttaagct tttgggatag   12240
ttggttaaca atatggtatt agagtcttat gattttttagg tggtctttga gttcaatcct  12300
tgctgctccc agttctagtt aatttctttt tggtccactt caaataaaaa gttgaattta   12360
agggtaaggc agctggacct gcgcattaat catgtgtcag gctcaaaggg cttttgtatg   12420
```

```
gggggcatgt tggaatata atatagaatc attcatgtgg tttcacctat caaggacaac    12480
tctagttttt gtcatacttg tattattaca gtgtctaaac tagacatgat cttttttccgg  12540 aaggaaattt aacttaaaag gaacttagat gcttcttgtt ctgtgatctt tatttgttta   12600 tttttttccaa tcttttttaac aattgaaagg tttagttgt atccaatctt tttatacatt  12660
tggactatct accatatcat ttagcaaact tgtttgctgc tcagattctc ctttggacta   12720
tctaccatat catttagcaa acctgttcac tgctcagatt ctcatttatt ctttgtttcc   12780
tctatttttc agtggcaagt tggagagtta aagagactga gaggatgata gcaatctgca   12840
cagaactcag aaaggtgagt gtcttgctaa ttcctttatg gtttcgatat tactggactt   12900
tttacatctc actgacctac tctgtcttgg tatttcagct aggagcaaca gttgaagaag   12960
gtcctgatta ctgtgtgatt actccacctg agaaattgaa tgtcacagct atagacacat   13020
atgatgacca cagaatggcc atggcattct ctcttgctgc ttgtggggat gttccagtaa   13080
ccatcaagga tcctggttgc accaggaaga catttccyga ctactttgaa gtccttgaga   13140
ggttmacaaa gcactaagca ttttgtacat tgagtaggaa gagagagaga gataaatact   13200
cacaaaacag tgagtatatg catggcttgc ttttgtttct taacattccc ttgtaagaac   13260
ttgagataat ttgtattgtt ggaaagagct attgattctg ttgtatcaaa gtaatttaat   13320
ttccagtaca gacttggctc tattcctcat atgtggtggt gtacattgca tctttgcatt   13380
tgatcccatt tctattggga taggaccata ccttttttg tttattattc aagtcaaact   13440
tagcagataa tatgtggtga ccagaaaata gtctagctag caaatagacc tgtgattgca   13500
tgtttgaatt caggacttca ggacatttaa ttaatgagtg acaatgttaa aaagctcgcc   13560
aacaggagtt gacacatctg attgagtctt ctattaacac taactgtaac ttgagtttga   13620
ttatcagatt cctcctgttg gtaggtaata tgtaaatttc actatatatt taccgaggtt   13680
ggtggtctta cttgactttg aagaggtgag tgtaatttaa acttttatat caaaaaaga   13740 ttgctaaaag cttgagtggc atgcaacaaa tagcaatgaa agaatgacta tggccttggg   13800
aaccaaatgg ccacgtacca cttttccacc aacttgagag ccctggtcct ggatgatgcc   13860 ccttttttt tttcatttct ttgacaataa agaaagttct tattcttggc aattgcaagt   13920 cgttgtgga agtcacatga aattccat aggcttcatt gttcaaatcc tttagtcact    13980
aactaaaggc tggacctatg caagaatttt ggctactctt ataaatgctg tgcggcaaag   14040
actacgaaaa aatataaatt attgcatatc tagaggtgag gttcattgct cccatccatt   14100
tttccaagaa ctaaaatata tataaattat taatatgata ttacattgaa aaataatatt   14160
tttcttttaa atatgtgatc ataagtttaa tttaagtct attcatacga aaaaatatt    14220 tattagaaaa gattaattta ttaaatggat ctcaatattt taagaaatta acttttagct   14280
ctcaaccaac agatgatttg agttaaaaaa atgtatatat aaactattgc atatctgctg   14340 attttgttt gtaacaccaa taagtgggca ttttactaaa tccatgtgac aatgtactga    14400
atgttttaga atacagtctg gtttgataat aaaacgtgca taagtccag cttatgttaa    14460 ctcttaattc atggaaaatg atgatatgcg aattgaaaga aagaaaacca taatgtaagt   14520
gcagttttct ctctctttt taatattatt caatatcaga ttgcacatgg aagggtat     14580 tggctcatgt gggatattag ttttttgtccc ttacctaaaa agagagaaag agaaaaataa  14640
caatttaaaa agagtaccac cgctaccacc ttttcgcctt ttaaattttt gttctgtttt   14700
cactactctt tcatgcgttg tttgttggct tctgatagtg acgaatatga tataatgatt   14760
```

-continued

| | |
|---|---|
| ttatgttggg aaaaaagtgc catgtaaatt ctagagattg aaattttagc atcaaattat | 14820 |
| ttatttatc accttttaaa atttgttgca tgtgaaagaa tttgaagctc tccaacaagg | 14880 |
| aaataacact tcaatcctta gagtcatcct ctagatccca aaagaatgtg atgtttatac | 14940 |
| acattagtat atatatatat atatatatat atatatatat atatatatat atatatatat | 15000 |
| atatatatat agggtttata ttatattaat gagtgatgta cgaggacggt ggtgacacta | 15060 |
| tatggccaaa acaagtgtaa tataattatt ttttttctc aagtattact ctatccttga | 15120 |
| atattattag tcttaaatct tcaagcacct tgtgaacgaa gcaatcttgt cc | 15172 |

<210> SEQ ID NO 37
<211> LENGTH: 522
<212> TYPE: DNA
<213> ORGANISM: Figwort Mosaic Virus
<220> FEATURE:
<223> OTHER INFORMATION: Enhancer

<400> SEQUENCE: 37

| | |
|---|---|
| aagcttcccg ggccggccgc agctggcttg tggggaccag acaaaaaagg aatggtgcag | 60 |
| aattgttagg cgcacctacc aaaagcatct ttgcctttat tgcaaagata aagcagattc | 120 |
| ctctagtaca agtggggaac aaaataacgt ggaaaagagc tgtcctgaca gcccactcac | 180 |
| taatgcgtat gacgaacgca gtgacgacca caaaactcga gacttttcaa caaagggtaa | 240 |
| tatccggaaa cctcctcgga ttccattgcc cagctatctg tcactttatt gtgaagatag | 300 |
| tggaaaagga aggtggctcc tacaaatgcc atcattgcga taaaggaaag gccatcgttg | 360 |
| aagatgcctc tgccgacagt ggtcccaaag atggaccccc acccacgagg agcatcgtgg | 420 |
| aaaaagaaga cgttccaacc acgtcttcaa agcaagtgga ttgatgtgat atctccactg | 480 |
| acgtaaggga tgacgcacaa tcccactatc cttcttaatt aa | 522 |

<210> SEQ ID NO 38
<211> LENGTH: 552
<212> TYPE: DNA
<213> ORGANISM: Figwort Mosaic Virus
<220> FEATURE:
<223> OTHER INFORMATION: Enhancer

<400> SEQUENCE: 38

| | |
|---|---|
| aagcttcccg ggccggccgc agctggcttg tggggaccag acaaaaaagg aatggtgcag | 60 |
| aattgttagg cgcacctacc aaaagcatct ttgcctttat tgcaaagata aagcagattc | 120 |
| ctctagtaca agtggggaac aaaataacgt ggaaaagagc tgtcctgaca gcccactcac | 180 |
| taatgcgtat gacgaacgca gtgacgacca caaaactcga gaacatggtg gagcacgaca | 240 |
| cacttgtcta ctccaagaat atcaaagata cagtctcaga agaccagagg gctattgaga | 300 |
| cttttcaaca agggtaata tcgggaaacc tcctcggatt ccattgccca gctatctgtc | 360 |
| acttcatcga aaggacagta gaaaggaag atggcttcta caaatgccat cattgcgata | 420 |
| aaggaaaggc tatcgttcaa gatgcctcta ccgacagtgg tcccaaagat ggaccccac | 480 |
| ccacgaggaa catcgtggaa aaagaagacg ttccaaccac gtcttcaaag caagtggatt | 540 |
| gatgttaatt aa | 552 |

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
ctgcagggat cctggttgca ccaggaag                                28

<210> SEQ ID NO 40
<211> LENGTH: 29
<212> TYPE: DNA
<213> ORGANISM: Artificial Sequence
<220> FEATURE:
<223> OTHER INFORMATION: Primer

<400> SEQUENCE: 40
gaattcccgg gtatggtgaa tttcatgtg                               29

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gacttctcgg gtaccatcac attgc                                   25

<210> SEQ ID NO 42
<211> LENGTH: 55
<212> TYPE: DNA
<213> ORGANISM: Artificial Sequence
<220> FEATURE:
<223> OTHER INFORMATION: Primer

<400> SEQUENCE: 42
cacctgcagc aaccacagct gctgtcaaag aacgcattgc aataccagca tttcc   55

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
aatttaatta attcataaat atgttac                                 27

<210> SEQ ID NO 44
<211> LENGTH: 73
<212> TYPE: DNA
<213> ORGANISM: Artificial Sequence
<220> FEATURE:
<223> OTHER INFORMATION: Primer

<400> SEQUENCE: 44
ggtcttctcc ttcttagttc tcaactactt gttcttctgc tgccagattt caattttcct   60
taaagttgtg aac                                                73

<210> SEQ ID NO 45
<211> LENGTH: 72
<212> TYPE: DNA
<213> ORGANISM: Artificial Sequence
<220> FEATURE:
<223> OTHER INFORMATION: Primer

<400> SEQUENCE: 45
atctggcagc agaagaacaa gtagttgaga actaagaagg agaagaccat ggcccaagtg   60

-continued

```
agcagagtgc ac                                                      72

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
ggcaatgtga tggatcccga gaag                                         24

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
gcgccatggc ggcatcggtt tccaggg                                      27

<210> SEQ ID NO 48
<211> LENGTH: 33
<212> TYPE: DNA
<213> ORGANISM: Artificial Sequence
<220> FEATURE:
<223> OTHER INFORMATION: Primer

<400> SEQUENCE: 48
gcgggtacct cagacaagca cctgagctgc agc                               33

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49
gcggcatgcc caacaatggc tcgtc                                        25

<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50
gcggatcctt atttcttcag ttcagcca                                     28

<210> SEQ ID NO 51
<211> LENGTH: 9
<212> TYPE: PRT
<213> ORGANISM: Motif
<220> FEATURE:
<221> NAME/KEY: MISC_FEATURE
<222> LOCATION: (5)..(5)
<223> OTHER INFORMATION: Xaa is any amino acid but not S or T

<400> SEQUENCE: 51

Ala Leu Leu Met Xaa Ala Pro Leu Ala
1               5

<210> SEQ ID NO 52
```

```
<211> LENGTH: 8
<212> TYPE: PRT
<213> ORGANISM: Motif
<220> FEATURE:
<221> NAME/KEY: MISC_FEATURE
<222> LOCATION: (5)..(5)
<223> OTHER INFORMATION: Xaa is any amino acid but not V

<400> SEQUENCE: 52

Glu Ile Glu Ile Xaa Asp Lys Leu
1               5

<210> SEQ ID NO 53
<211> LENGTH: 7
<212> TYPE: PRT
<213> ORGANISM: Motif
<220> FEATURE:
<221> NAME/KEY: MISC_FEATURE
<222> LOCATION: (3)..(3)
<223> OTHER INFORMATION: Xaa is V or I
<220> FEATURE:
<221> NAME/KEY: MISC_FEATURE
<222> LOCATION: (4)..(4)
<223> OTHER INFORMATION: Xaa is K or S
<220> FEATURE:
<221> NAME/KEY: MISC_FEATURE
<222> LOCATION: (5)..(5)
<223> OTHER INFORMATION: Xaa is any amino acid but not V

<400> SEQUENCE: 53

Phe Gly Xaa Xaa Xaa Glu His
1               5

<210> SEQ ID NO 54
<211> LENGTH: 7
<212> TYPE: PRT
<213> ORGANISM: Motif
<220> FEATURE:
<221> NAME/KEY: MISC_FEATURE
<222> LOCATION: (3)..(3)
<223> OTHER INFORMATION: Xaa is K orR
<220> FEATURE:
<221> NAME/KEY: MISC_FEATURE
<222> LOCATION: (4)..(4)
<223> OTHER INFORMATION: Xaa is any amino acid but not R

<400> SEQUENCE: 54

Ala Leu Xaa Xaa Leu Gly Leu
1               5

<210> SEQ ID NO 55
<211> LENGTH: 15
<212> TYPE: PRT
<213> ORGANISM: Motif
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid but not T (and/or the
     amino acid at position 9 is not E)
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid but not E (and/or the
     aminoacidat position 6 is any amino acid but not T)
<220> FEATURE:
```

```
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is I or V

<400> SEQUENCE: 55

Gly Leu Xaa Val Glu Xaa Asp Xaa Xaa Xaa Xaa Xaa Ala Xaa Val
1               5                   10                  15

<210> SEQ ID NO 56
<211> LENGTH: 9
<212> TYPE: PRT
<213> ORGANISM: Motif
<220> FEATURE:
<221> NAME/KEY: MISC_FEATURE
<222> LOCATION: (5)..(5)
<223> OTHER INFORMATION: Xaa is any amino acid but not K (and/or the
      amino acid at position 9 is any amino acid but not T)
<220> FEATURE:
<221> NAME/KEY: MISC_FEATURE
<222> LOCATION: (7)..(7)
<223> OTHER INFORMATION: Xaa is L or V
<220> FEATURE:
<221> NAME/KEY: MISC_FEATURE
<222> LOCATION: (8)..(8)
<223> OTHER INFORMATION: Xaa is K or N
<220> FEATURE:
<221> NAME/KEY: MISC_FEATURE
<222> LOCATION: (9)..(9)
<223> OTHER INFORMATION: Xaa is any amino acid but not T (and/or the
      amino acid at position 5 is any amino acid but not K)

<400> SEQUENCE: 56

Ile Thr Pro Pro Xaa Lys Xaa Xaa Xaa
1               5

<210> SEQ ID NO 57
<211> LENGTH: 8
<212> TYPE: PRT
<213> ORGANISM: Motif
<220> FEATURE:
<221> NAME/KEY: MISC_FEATURE
<222> LOCATION: (3)..(3)
<223> OTHER INFORMATION: Xaa is any amino acid but not N or L
<220> FEATURE:
<221> NAME/KEY: MISC_FEATURE
<222> LOCATION: (4)..(4)
<223> OTHER INFORMATION: Xaa is D or N

<400> SEQUENCE: 57

Thr Ile Xaa Xaa Pro Gly Cys Thr
1               5

<210> SEQ ID NO 58
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is D or N
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
```

```
<221> NAME/KEY: MISC_FEATURE
<222> LOCATION: (8)..(8)
<223> OTHER INFORMATION: Xaa is any amino acid but not R
<220> FEATURE:
<221> NAME/KEY: MISC_FEATURE
<222> LOCATION: (9)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is K or R

<400> SEQUENCE: 58

Xaa Tyr Phe Xaa Val Leu Xaa Xaa Xaa Xaa Xaa His
1               5                   10

<210> SEQ ID NO 59
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (8)..(8)
<223> OTHER INFORMATION: Xaa is I or L or Q
<220> FEATURE:
<221> NAME/KEY: MISC_FEATURE
<222> LOCATION: (11)..(11)
<223> OTHER INFORMATION: Xaa is V or A or T
<220> FEATURE:
<221> NAME/KEY: MISC_FEATURE
<222> LOCATION: (12)..(12)
<223> OTHER INFORMATION: Xaa is S or G

<400> SEQUENCE: 59

Xaa Val Glu Gly Cys Gly Gly Xaa Phe Pro Xaa Xaa
1               5                   10

<210> SEQ ID NO 60
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (8)..(8)
<223> OTHER INFORMATION: Xaa is I or L or Q
<220> FEATURE:
<221> NAME/KEY: MISC_FEATURE
<222> LOCATION: (11)..(11)
<223> OTHER INFORMATION: Xaa is V or A or T

<400> SEQUENCE: 60

Xaa Val Val Gly Cys Gly Gly Xaa Phe Pro Xaa Glu
1               5                   10

<210> SEQ ID NO 61
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (8)..(8)
```

```
<223> OTHER INFORMATION: Xaa is I or L or Q
<220> FEATURE:
<221> NAME/KEY: MISC_FEATURE
<222> LOCATION: (11)..(11)
<223> OTHER INFORMATION: Xaa is V or A or T
<220> FEATURE:
<221> NAME/KEY: MISC_FEATURE
<222> LOCATION: (12)..(12)
<223> OTHER INFORMATION: Xaa is S or G

<400> SEQUENCE: 61

Xaa Val Val Gly Cys Gly Gly Xaa Phe Pro Xaa Xaa
1               5                   10

<210> SEQ ID NO 62
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (11)..(11)
<223> OTHER INFORMATION: Xaa is V or A or T
<220> FEATURE:
<221> NAME/KEY: MISC_FEATURE
<222> LOCATION: (12)..(12)
<223> OTHER INFORMATION: Xaa is S or G

<400> SEQUENCE: 62

Xaa Val Val Gly Cys Gly Gly Lys Phe Pro Xaa Xaa
1               5                   10

<210> SEQ ID NO 63
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (11)..(11)
<223> OTHER INFORMATION: Xaa is V or A or T

<400> SEQUENCE: 63

Xaa Val Glu Gly Cys Gly Gly Lys Phe Pro Xaa Glu
1               5                   10

<210> SEQ ID NO 64
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (8)..(8)
<223> OTHER INFORMATION: Xaa is I or L or Q
<220> FEATURE:
<221> NAME/KEY: MISC_FEATURE
<222> LOCATION: (11)..(11)
<223> OTHER INFORMATION: Xaa is V or A or T

<400> SEQUENCE: 64

Xaa Val Glu Gly Cys Gly Gly Xaa Phe Pro Xaa Glu
1               5                   10
```

```
<210> SEQ ID NO 65
<211> LENGTH: 12
<212> TYPE: PRT
<213> ORGANISM: Motif
<220> FEATURE:
<221> NAME/KEY: MISC_FEATURE
<222> LOCATION: (1)..(1)
<223> OTHER INFORMATION: Xaa is I or V
<220> FEATURE:
<221> NAME/KEY: MISC_FEATURE
<222> LOCATION: (11)..(11)
<223> OTHER INFORMATION: Xaa is V or A or T
<220> FEATURE:
<221> NAME/KEY: MISC_FEATURE
<222> LOCATION: (12)..(12)
<223> OTHER INFORMATION: Xaa is S or G

<400> SEQUENCE: 65

Xaa Val Glu Gly Cys Gly Gly Lys Phe Pro Xaa Xaa
1               5                   10

<210> SEQ ID NO 66
<211> LENGTH: 10
<212> TYPE: PRT
<213> ORGANISM: Motif

<400> SEQUENCE: 66

Gly Asn Ala Gly Thr Ala Met Arg Pro Leu
1               5                   10

<210> SEQ ID NO 67
<211> LENGTH: 10
<212> TYPE: PRT
<213> ORGANISM: Motif

<400> SEQUENCE: 67

Gly Asn Ala Gly Ile Ala Met Arg Ser Leu
1               5                   10

<210> SEQ ID NO 68
<211> LENGTH: 18
<212> TYPE: PRT
<213> ORGANISM: Motif
<220> FEATURE:
<221> NAME/KEY: MISC_FEATURE
<222> LOCATION: (2)..(2)
<223> OTHER INFORMATION: Xaa is A or V

<400> SEQUENCE: 68

Lys Xaa Ala Lys Arg Ala Val Val Gly Cys Gly Gly Lys Phe Pro
1               5                   10                  15
Val Glu

<210> SEQ ID NO 69
<211> LENGTH: 14
<212> TYPE: PRT
<213> ORGANISM: Motif

<400> SEQUENCE: 69

Gly Asn Ala Gly Thr Ala Met Arg Pro Leu Thr Ala Ala Val
1               5                   10

<210> SEQ ID NO 70
<211> LENGTH: 14
<212> TYPE: PRT
<213> ORGANISM: Motif
```

-continued

```
<400> SEQUENCE: 70

Gly Asn Ala Gly Ile Ala Met Arg Ser Leu Thr Ala Ala Val
1               5                   10
```